US011806331B2

(12) United States Patent
Davidson et al.

(10) Patent No.: US 11,806,331 B2
(45) Date of Patent: Nov. 7, 2023

(54) LOW DOSE THERAPEUTIC TREATMENT

(71) Applicant: Syqe Medical Ltd., Tel-Aviv (IL)

(72) Inventors: Perry Davidson, Tel-Aviv (IL); Seth Kindler, Tel-Aviv (IL); Shlomo Almog, Reut (IL); Binyamin Schwartz, Sde Eliezer (IL); Aaron Schorr, Doar-Na Misgav (IL); Daniella Atzmony, Modiin-Maccabim-Reut (IL)

(73) Assignee: Syqe Medical Ltd., Tel-Aviv (IL)

( * ) Notice: Subject to any disclaimer, the term of this patent is extended or adjusted under 35 U.S.C. 154(b) by 116 days.

(21) Appl. No.: 16/068,373

(22) PCT Filed: Jan. 5, 2017

(86) PCT No.: PCT/IL2017/050014
§ 371 (c)(1),
(2) Date: Jul. 6, 2018

(87) PCT Pub. No.: WO2017/118980
PCT Pub. Date: Jul. 13, 2017

(65) Prior Publication Data
US 2019/0015382 A1    Jan. 17, 2019

Related U.S. Application Data

(60) Provisional application No. 62/275,314, filed on Jan. 6, 2016.

(51) Int. Cl.
*A61M 11/00* (2006.01)
*A61K 31/352* (2006.01)
(Continued)

(52) U.S. Cl.
CPC ............ *A61K 31/352* (2013.01); *A61K 9/008* (2013.01); *A61M 11/042* (2014.02);
(Continued)

(58) Field of Classification Search
CPC .... A61M 15/00–0013; A61M 15/0028; A61M 15/0065–0078; A61M 15/0085;
(Continued)

(56) References Cited

U.S. PATENT DOCUMENTS 3,203,432 A    8/1965 Green et al.
3,894,544 A    7/1975 Egri
(Continued)

FOREIGN PATENT DOCUMENTS

AU    199641966    5/1996
AU    708269    7/1999
(Continued)

OTHER PUBLICATIONS

International Search Report and the Written Opinion dated Dec. 31, 2019 From the International Searching Authority Re. Application No. PCT/IL2019/051163. (16 Pages).
(Continued)

*Primary Examiner* — Samchuan C Yao
*Assistant Examiner* — Sarah B Lederer

(57) ABSTRACT

Some embodiments of the invention relate to a system for delivering to a subject at least one pre-determined amount of THC, the system comprising: a memory which stores a scheduled regimen for delivery of THC to the subject, the scheduled regimen defining: a maximal amount of THC to be delivered, the amount being 0.75 mg THC or less, and a time period within which that amount is delivered, the time period being 2 hours or longer; a decision module which decides, according to the scheduled regimen, if a delivery should take place; and an inhaler device for delivering THC to the subject, the inhaler device comprising a controller which carries out delivery of THC based on the decision made by the decision module.

26 Claims, 16 Drawing Sheets

(51) Int. Cl.
*A61K 9/00* (2006.01)
*A61M 15/00* (2006.01)
*A61M 11/04* (2006.01)
*G16H 20/13* (2018.01)
*A61P 29/02* (2006.01)
*G16H 40/63* (2018.01)

(52) U.S. Cl.
CPC ...... *A61M 15/0003* (2014.02); *A61M 15/009* (2013.01); *A61P 29/02* (2018.01); *G16H 20/13* (2018.01); *G16H 40/63* (2018.01); *A61M 2205/52* (2013.01)

(58) Field of Classification Search
CPC ...... A61M 15/009–0098; A61M 15/06; A61M 15/08; A61M 15/085; A24F 47/00; A24F 47/002; A24F 47/004; A24F 47/008; A24F 40/00; A24F 40/30; A61K 31/35; A61K 9/008; A61K 9/00; A61P 29/02; A61P 11/00
See application file for complete search history.

(56) References Cited

U.S. PATENT DOCUMENTS

| | | | |
|---|---|---|---|
| 4,603,030 A | 7/1986 | McCarthy | |
| 4,735,358 A | 4/1988 | Morita et al. | |
| 4,966,171 A | 10/1990 | Serrano et al. | |
| 4,969,477 A | 11/1990 | Yagisawa | |
| 5,023,020 A | 6/1991 | Machida et al. | |
| 5,086,978 A | 2/1992 | Fertig | |
| 5,105,838 A | 4/1992 | White et al. | |
| 5,301,666 A | 4/1994 | Lerk et al. | |
| 5,333,106 A | 7/1994 | Lanpher et al. | |
| 5,388,594 A | 2/1995 | Counts et al. | |
| 5,404,871 A | 4/1995 | Goodman et al. | |
| 5,443,606 A | 8/1995 | Hassenboehler, Jr. et al. | |
| 5,479,948 A | 1/1996 | Counts et al. | |
| 5,503,869 A | 4/1996 | Van Oort | |
| 5,546,965 A | 8/1996 | White | |
| 5,565,148 A | 10/1996 | Pendergrass, Jr. | |
| 5,649,554 A | 7/1997 | Sprinkel et al. | |
| 5,655,520 A | 8/1997 | Howe et al. | |
| 5,792,057 A | 8/1998 | Rubsamen et al. | |
| 5,805,768 A | 9/1998 | Schwartz et al. | |
| 5,819,756 A | 10/1998 | Mielordt | |
| 5,855,564 A | 1/1999 | Ruskowicz | |
| 6,547,229 B1 | 4/2003 | Hanson et al. | |
| 6,703,418 B2 | 3/2004 | Plasse | |
| 6,713,024 B1 | 3/2004 | Arnell et al. | |
| 6,761,164 B2 | 7/2004 | Amirpour et al. | |
| 6,871,647 B2 | 3/2005 | Allan et al. | |
| 7,088,914 B2 | 8/2006 | Whittle et al. | |
| 7,169,378 B2 | 1/2007 | Rabinowitz et al. | |
| 7,287,530 B1 | 10/2007 | Stuart | |
| 7,376,344 B2 | 5/2008 | Manne | |
| 7,389,943 B2 | 6/2008 | Jaworski | |
| 7,537,005 B2 | 5/2009 | Dave | |
| 7,690,076 B2 | 6/2010 | Tannous | |
| 7,987,846 B2 | 8/2011 | Hale et al. | |
| 8,235,037 B2 | 8/2012 | Hale et al. | |
| 8,408,200 B2 | 4/2013 | Clark et al. | |
| 8,490,627 B2 | 7/2013 | Levin et al. | |
| 8,615,407 B2 | 12/2013 | Hyde et al. | |
| 9,775,379 B2 | 10/2017 | Davidson et al. | |
| 9,802,011 B2 | 10/2017 | Davidson et al. | |
| 9,943,114 B2 | 4/2018 | Batista | |
| 9,993,602 B2 | 6/2018 | Davidson et al. | |
| 10,080,851 B2 | 9/2018 | Davidson et al. | |
| 10,179,215 B2 | 1/2019 | Raichman | |
| 10,299,515 B2 | 5/2019 | Krietzman | |
| 11,006,661 B2 | 5/2021 | Valadi | |
| 11,044,950 B2 | 6/2021 | Collett et al. | |
| 11,071,712 B2 | 7/2021 | Davidson et al. | |
| 2001/0027789 A1 | 10/2001 | Goede et al. | |
| 2002/0078951 A1 | 6/2002 | Nichols et al. | |
| 2002/0168322 A1 | 11/2002 | Clark et al. | |
| 2003/0037785 A1 | 2/2003 | Sonntag | |
| 2003/0041859 A1 | 3/2003 | Abrams et al. | |
| 2003/0049025 A1 | 3/2003 | Neumann et al. | |
| 2003/0062042 A1* | 4/2003 | Wensley ............... | A61K 31/519 128/203.12 |
| 2003/0136420 A1 | 7/2003 | Kraker | |
| 2003/0163099 A1 | 8/2003 | Wermeling et al. | |
| 2003/0168057 A1 | 9/2003 | Snyder et al. | |
| 2003/0200964 A1 | 10/2003 | Blakley et al. | |
| 2004/0045567 A1 | 3/2004 | Lewis et al. | |
| 2004/0069798 A1 | 4/2004 | Grey et al. | |
| 2004/0084044 A1 | 5/2004 | Childers et al. | |
| 2004/0099266 A1 | 5/2004 | Cross et al. | |
| 2004/0188546 A1 | 9/2004 | Tabata et al. | |
| 2004/0192760 A1 | 9/2004 | Whittle et al. | |
| 2004/0234699 A1 | 11/2004 | Hale et al. | |
| 2005/0063686 A1 | 3/2005 | Whittle et al. | |
| 2005/0126562 A1 | 6/2005 | Rabinowitz et al. | |
| 2005/0244521 A1 | 11/2005 | Strickland et al. | |
| 2005/0268909 A1 | 12/2005 | Bonney et al. | |
| 2005/0268911 A1 | 12/2005 | Cross et al. | |
| 2006/0102175 A1 | 5/2006 | Nelson | |
| 2006/0120962 A1 | 6/2006 | Rabinowitz et al. | |
| 2006/0157491 A1 | 7/2006 | Whittle et al. | |
| 2006/0167084 A1 | 7/2006 | Dudley | |
| 2006/0258738 A1 | 11/2006 | Dieterich | |
| 2007/0023060 A1 | 2/2007 | Ra | |
| 2007/0072938 A1 | 3/2007 | Rose | |
| 2007/0122353 A1 | 3/2007 | Hale et al. | |
| 2007/0074721 A1 | 4/2007 | Harmer et al. | |
| 2007/0102013 A1 | 5/2007 | Adams et al. | |
| 2007/0163580 A1 | 7/2007 | Braithwaite | |
| 2007/0209661 A1 | 9/2007 | Smyth et al. | |
| 2007/0240712 A1 | 10/2007 | Fleming et al. | |
| 2007/0286816 A1 | 12/2007 | Hale et al. | |
| 2008/0072898 A1 | 3/2008 | Quoniam | |
| 2008/0078382 A1 | 4/2008 | LeMahieu et al. | |
| 2008/0140250 A1 | 6/2008 | Dave | |
| 2008/0159961 A1 | 7/2008 | Woolfe et al. | |
| 2008/0176885 A1 | 7/2008 | Holtman et al. | |
| 2008/0181942 A1 | 7/2008 | Zajicek | |
| 2008/0199161 A1 | 8/2008 | Hickey et al. | |
| 2008/0202515 A1 | 8/2008 | Hodson et al. | |
| 2008/0299048 A1 | 12/2008 | Hale et al. | |
| 2008/0308101 A1 | 12/2008 | Spandorfer | |
| 2008/0311176 A1 | 12/2008 | Hale et al. | |
| 2009/0084865 A1 | 4/2009 | Maharajh | |
| 2009/0151722 A1 | 6/2009 | Eason et al. | |
| 2009/0194105 A1 | 8/2009 | Besseller et al. | |
| 2009/0197941 A1 | 8/2009 | Guy et al. | |
| 2009/0241949 A1 | 10/2009 | Smutney et al. | |
| 2009/0293888 A1 | 12/2009 | Williams et al. | |
| 2009/0293892 A1 | 12/2009 | Williams et al. | |
| 2009/0308390 A1 | 12/2009 | Smutney et al. | |
| 2009/0320836 A1 | 12/2009 | Baker, Jr. | |
| 2010/0012118 A1 | 1/2010 | Storz | |
| 2010/0035978 A1 | 2/2010 | Guy et al. | |
| 2010/0154795 A1 | 6/2010 | Pentafragas | |
| 2010/0168228 A1 | 7/2010 | Bose | |
| 2010/0181387 A1 | 7/2010 | Zaffaroni et al. | |
| 2010/0204602 A1 | 8/2010 | Addington et al. | |
| 2010/0250280 A1 | 9/2010 | Sutherland | |
| 2010/0294278 A1 | 11/2010 | Mosier et al. | |
| 2010/0300442 A1 | 12/2010 | Houzego et al. | |
| 2010/0326438 A1 | 12/2010 | Dunne | |
| 2011/0030706 A1 | 2/2011 | Gibson et al. | |
| 2011/0036346 A1 | 2/2011 | Cohen et al. | |
| 2011/0038958 A1 | 2/2011 | Kikuchi et al. | |
| 2011/0126831 A1 | 6/2011 | Pernia | |
| 2011/0240011 A1 | 10/2011 | Caldwell | |
| 2011/0244020 A1 | 10/2011 | Hale et al. | |
| 2011/0265806 A1 | 11/2011 | Alarcon et al. | |
| 2012/0003318 A1 | 1/2012 | Schuler et al. | |
| 2012/0006700 A1 | 1/2012 | Geboers et al. | |
| 2012/0116241 A1 | 5/2012 | Shie et al. | |
| 2012/0252885 A1 | 10/2012 | Barbato | |

(56) References Cited

U.S. PATENT DOCUMENTS

| | | |
|---|---|---|
| 2012/0255546 A1 | 10/2012 | Goetz et al. |
| 2012/0291791 A1 | 11/2012 | Pradeep |
| 2012/0304990 A1 | 12/2012 | Todd |
| 2012/0325227 A1 | 12/2012 | Robinson et al. |
| 2013/0032139 A1 | 2/2013 | Hale et al. |
| 2013/0053719 A1 | 2/2013 | Wekell |
| 2013/0081623 A1 | 4/2013 | Buchberger |
| 2013/0087144 A1 | 4/2013 | Todd |
| 2013/0112197 A1 | 5/2013 | Kruener et al. |
| 2013/0213397 A1 | 8/2013 | Curtis et al. |
| 2013/0269694 A1 | 10/2013 | Patton et al. |
| 2013/0276799 A1* | 10/2013 | Davidson ............ A61M 11/041 131/273 |
| 2013/0304990 A1 | 11/2013 | Bass et al. |
| 2013/0333700 A1 | 12/2013 | Buchberger |
| 2014/0037794 A1 | 2/2014 | Patera et al. |
| 2014/0060525 A1 | 3/2014 | Hale et al. |
| 2014/0088045 A1 | 3/2014 | Rigas et al. |
| 2014/0100249 A1 | 4/2014 | Sears et al. |
| 2014/0106324 A1 | 4/2014 | Adams et al. |
| 2014/0144429 A1 | 5/2014 | Wensley et al. |
| 2014/0190496 A1 | 7/2014 | Wensley et al. |
| 2014/0202454 A1 | 7/2014 | Buchberger |
| 2014/0209105 A1 | 7/2014 | Sears et al. |
| 2014/0238423 A1 | 8/2014 | Tucker et al. |
| 2014/0366898 A1 | 12/2014 | Monsees et al. |
| 2015/0064672 A1 | 3/2015 | Bars |
| 2015/0075521 A1 | 3/2015 | Lee et al. |
| 2015/0090253 A1 | 4/2015 | Farrow |
| 2015/0122252 A1 | 5/2015 | Frija |
| 2015/0136124 A1 | 5/2015 | Aronie et al. |
| 2015/0237913 A1 | 8/2015 | Suzuki et al. |
| 2016/0007653 A1 | 1/2016 | Tu |
| 2016/0044960 A1 | 2/2016 | O'Connor |
| 2016/0100624 A1 | 4/2016 | Yilmaz et al. |
| 2016/0121057 A1 | 5/2016 | Dyche et al. |
| 2016/0166564 A1 | 6/2016 | Myers et al. |
| 2016/0166786 A1 | 6/2016 | Kinzer |
| 2016/0171164 A1 | 6/2016 | Kinzer |
| 2016/0183589 A1 | 6/2016 | Born et al. |
| 2016/0219938 A1 | 8/2016 | Mamoun et al. |
| 2016/0271347 A1 | 9/2016 | Raichman |
| 2016/0286860 A1 | 10/2016 | Flayler |
| 2016/0295922 A1 | 10/2016 | John et al. |
| 2016/0309774 A1 | 10/2016 | Wand |
| 2016/0309784 A1 | 10/2016 | Silvestrini et al. |
| 2016/0331022 A1 | 11/2016 | Cameron |
| 2016/0331913 A1 | 11/2016 | Bourque |
| 2016/0345630 A1 | 12/2016 | Mironov et al. |
| 2016/0354573 A1 | 12/2016 | Buswell et al. |
| 2017/0095624 A1 | 4/2017 | Davidson et al. |
| 2017/0106153 A1 | 4/2017 | Davidson et al. |
| 2017/0119979 A1 | 5/2017 | Davidson et al. |
| 2017/0119981 A1 | 5/2017 | Davidson et al. |
| 2017/0127727 A1 | 5/2017 | Davidson et al. |
| 2017/0136196 A1 | 5/2017 | Davidson et al. |
| 2017/0150755 A1 | 6/2017 | Batista |
| 2017/0157341 A1 | 6/2017 | Pandya |
| 2017/0157343 A1 | 6/2017 | Davidson et al. |
| 2017/0164657 A1 | 6/2017 | Batista |
| 2017/0203058 A1 | 7/2017 | Davidson et al. |
| 2017/0295848 A1 | 10/2017 | LaMothe |
| 2017/0304567 A1 | 10/2017 | Adelson |
| 2017/0360089 A1 | 12/2017 | Davidson et al. |
| 2018/0043115 A1 | 2/2018 | Gould et al. |
| 2018/0110943 A1 | 4/2018 | Raichman |
| 2018/0263288 A1 | 9/2018 | Goldstein et al. |
| 2018/0318529 A1 | 11/2018 | Davidson et al. |
| 2018/0344954 A1 | 12/2018 | Davidson et al. |
| 2019/0001087 A1 | 1/2019 | Davidson et al. |
| 2019/0009039 A1 | 1/2019 | Davidson et al. |
| 2019/0124982 A1 | 5/2019 | Atkins et al. |
| 2019/0290862 A1 | 9/2019 | Davidson et al. |
| 2021/0023316 A1 | 1/2021 | Schorr et al. |
| 2021/0236414 A1 | 8/2021 | Davidson et al. |
| 2021/0402109 A1 | 12/2021 | Landa et al. |
| 2022/0031972 A1 | 2/2022 | Davidson et al. |
| 2022/0096760 A1 | 3/2022 | Schwartz et al. |
| 2022/0183962 A1 | 6/2022 | Davidson et al. |
| 2022/0211958 A1 | 7/2022 | Davidson et al. |
| 2022/0241523 A1 | 8/2022 | Davidson et al. |

FOREIGN PATENT DOCUMENTS

| | | |
|---|---|---|
| CA | 2599022 | 9/2005 |
| CA | 3025407 | 11/2017 |
| CN | 1323231 | 11/2001 |
| CN | 2816102 | 9/2006 |
| CN | 1925883 | 3/2007 |
| CN | 101053685 | 10/2007 |
| CN | 101130121 | 2/2008 |
| CN | 101132823 | 2/2008 |
| CN | 101360528 | 2/2009 |
| CN | 101415457 | 4/2009 |
| CN | 101980743 | 2/2011 |
| CN | 102355914 | 2/2012 |
| CN | 102438602 | 5/2012 |
| CN | 203166473 | 8/2013 |
| CN | 106659858 | 5/2017 |
| CN | 108260855 | 7/2018 |
| CN | 108712918 | 10/2018 |
| EA | 201100197 | 3/2012 |
| EP | 0 216 926 | 3/1991 |
| EP | 0539674 | 5/1993 |
| EP | 0547429 | 6/1993 |
| EP | 1358902 | 11/2003 |
| EP | 2145643 | 1/2010 |
| EP | 2292108 | 3/2011 |
| EP | 3160553 | 5/2017 |
| GB | 2108390 | 5/1983 |
| GB | 2340758 | 3/2000 |
| GB | 2456183 | 7/2009 |
| GB | 2495771 | 4/2013 |
| JP | 2002-527151 | 8/2002 |
| JP | 2003-503117 | 1/2003 |
| JP | 2003-079731 | 3/2003 |
| JP | 2003-275214 | 9/2003 |
| JP | 2004-283609 | 10/2004 |
| JP | 2004-298331 | 10/2004 |
| JP | 2005-503846 | 2/2005 |
| JP | 2005-516644 | 6/2005 |
| JP | 2005-516647 | 6/2005 |
| JP | 2006-507909 | 3/2006 |
| JP | 2007-0516015 | 6/2007 |
| JP | 2008-501406 | 1/2008 |
| JP | 2008-301847 | 12/2008 |
| JP | 2009-509523 | 3/2009 |
| JP | 2009-131686 | 6/2009 |
| JP | 2011-508765 | 3/2011 |
| JP | 2012-110499 | 6/2012 |
| JP | 2012-527329 | 11/2012 |
| JP | 2013-521075 | 6/2013 |
| JP | 2013-523395 | 6/2013 |
| JP | 2017-523828 | 8/2017 |
| JP | 2020-062479 | 4/2020 |
| KR | 10-1319228 | 10/2013 |
| RU | 2413544 | 3/2011 |
| RU | 107026 | 8/2011 |
| RU | 2460677 | 9/2012 |
| RU | 2017102234 | 7/2018 |
| WO | WO 91/11120 | 8/1991 |
| WO | WO 94/09842 | 5/1994 |
| WO | WO 96/32854 | 10/1996 |
| WO | WO 98/04308 | 2/1998 |
| WO | WO 00/21594 | 4/2000 |
| WO | WO 00/21598 | 4/2000 |
| WO | WO 00/24362 | 5/2000 |
| WO | WO 01/00263 | 1/2001 |
| WO | WO 01/17595 | 3/2001 |
| WO | WO 03/020057 | 3/2003 |
| WO | WO 03/030979 A1 | 4/2003 |
| WO | WO 03/037412 | 5/2003 |
| WO | WO 2005/061033 | 7/2005 |
| WO | WO 2005/072719 | 8/2005 |

(56) References Cited

FOREIGN PATENT DOCUMENTS

| | | |
|---|---|---|
| WO | WO 2005/072792 | 8/2005 |
| WO | WO 2005/120614 | 12/2005 |
| WO | WO 2007/018568 | 2/2007 |
| WO | WO 2007/042941 | 4/2007 |
| WO | WO 2008/024408 | 2/2008 |
| WO | WO 2008/024490 | 2/2008 |
| WO | WO 2008/116165 | 9/2008 |
| WO | WO 2009/102976 | 8/2009 |
| WO | WO 2009/124552 | 10/2009 |
| WO | WO 2010/015260 | 2/2010 |
| WO | WO 2011/073306 | 6/2011 |
| WO | WO2011/130183 | 10/2011 |
| WO | WO 2012/006125 | 1/2012 |
| WO | WO 2012/006126 | 1/2012 |
| WO | WO 2012/026963 | 3/2012 |
| WO | WO 2012/038903 | 3/2012 |
| WO | WO 2012/085919 | 6/2012 |
| WO | WO 2013/013808 | 1/2013 |
| WO | WO 2013/057185 | 4/2013 |
| WO | WO 2013/060781 | 5/2013 |
| WO | WO 2013/083636 | 6/2013 |
| WO | WO 2014/037794 | 3/2014 |
| WO | WO 2014/061477 | 4/2014 |
| WO | WO 2014/085719 | 6/2014 |
| WO | WO 2015/123064 | 8/2015 |
| WO | WO 2015/123317 | 8/2015 |
| WO | WO 2015/175979 | 11/2015 |
| WO | WO 2016/001921 | 1/2016 |
| WO | WO 2016/001922 | 1/2016 |
| WO | WO 2016/001923 | 1/2016 |
| WO | WO 2016/001924 | 1/2016 |
| WO | WO 2016/001925 | 1/2016 |
| WO | WO 2016/001926 | 1/2016 |
| WO | WO 2016/090303 | 6/2016 |
| WO | WO 2016/147188 | 9/2016 |
| WO | WO 2016/172802 | 11/2016 |
| WO | WO 2016/187696 | 12/2016 |
| WO | WO 2017/118980 | 7/2017 |
| WO | WO 2017/122196 | 7/2017 |
| WO | WO 2017/122201 | 7/2017 |
| WO | WO 2017/178958 | 10/2017 |
| WO | WO 2017/185051 | 10/2017 |
| WO | WO 2018/019855 | 2/2018 |
| WO | WO 2019/159170 | 8/2019 |
| WO | WO 2020/089890 | 5/2020 |
| WO | WO 2020/161721 | 8/2020 |
| WO | WO 2013/052586 | 3/2021 |

OTHER PUBLICATIONS

Wilsey et al. "A Randomized, Placebo-Controlled, Crossover Trial of Cannabis Cifarettes in Neuropathic Pain", The Journal of Pain, 9(6): 506-521, Published Online Apr. 10, 2008.
Notice of Reasons for Rejection dated Jan. 7, 2020 From the Japan Patent Office Re. Application No. 2016-576067 and Its Translation Into English. (10 Pages).
Notification of Office Action dated Jan. 3, 2020 From the China National Intellectual Property Administratin Re. Application No. 201580046016.9 and Its Translation Into English. (13 Pages).
Request for Examination and Search Report dated Nov. 22, 2018 From the Federal Government Institution, Federal Institute of Industrial Property of the Federal Service for Intellectual Property, Patents and Trademarks of the Russian Federation Re. Application No. 2017102236 and Its Translation of Office Action Into English. (7 Pages).
Request for Examination and Search Report dated Nov. 27, 2018 From the Federal Government Institution, Federal Institute of Industrial Property of the Federal Service of Intellectual Property, Patents and Trademarks of the Russian Federation Re. Application No. 2017102233 and Its Translation of Office Action Into English. (8 Pages).

Applicant-Initiated Interview Summary dated Dec. 30, 2019 From the U.S. Patent and Trademark Office Re. U.S. Appl. No. 15/690,323. (4 pages).
Notification of Office Action and Search Report dated Dec. 30, 2019 From the State Intellectual Property Office of the People's Republic of China Re. Application No. 201580045638.X. (11 Pages).
Notification of Office Action dated Dec. 27, 2019 From the State Intellectual Property Office of the People's Republic of China Re. Application No. 201580045136.7 and Its Translation Into English. (4 Pages).
Translation Dated Jan. 22, 2020 of Notification of Office Action dated Dec. 30, 2019 From the China National Intellectual Property Administration Re. Application No. 201580045638.X. (9 Pages).
McPartland et al. "Cannabis and Cannabis Extracts: Greater Than the Sum of Their Parts?", Journal of Cannabis Therapeutics, 1(3-4):103-132, Jun. 1, 2001.
Moreno-Sanz "Can You Pass the Acid Test? Critical Review and Novel Therapeutic Perspectives of Delta9-Tetrahydrocannabinolic Acid a", Cannabis and Cannabinoid Research. 1(1): 124-130, Published Online Jun. 1, 2016.
Decision of Rejection dated Aug. 27, 2019 From the Japan Patent Office Re. Application No. 2016-576071 and Its Translation Into English. (8 Pages).
Notice of Acceptance dated Aug. 28, 2019 From the Australian Government, IP Australia Re. Application No. 2015283589. (4 Pages).
Notification of Office Action and Search Report dated Sep. 3, 2019 From the State Intellectual Property Office of the People's Republic of China Re. Application No. 201580045136.7. (9 Pages).
Notification of Office Action and Search Report dated Sep. 3, 2019 From the State Intellectual Property Office of the People's Republic of China Re. Application No. 201580045638.X. (15 Pages).
Office Action dated Jan. 30, 2020 From the Israel Patent Office Re. Application No. 249836 and Its Translation Into English. (9 Pages).
Translation Dated Sep. 18, 2019 of Notification of Office Action dated Sep. 3, 2019 From the State Intellectual Property Office of the People's Republic of China Re. Application No. 201580045136.7. (5 Pages).
Examination Report dated Mar. 29, 2019 From the Australian Government, IP Australia Re. Application No. 2015283590. (5 Pages).
Notice of Reasons for Rejection dated May 7, 2019 From the Japan Patent Office Re. Application No. 2016-576068 and Its Translation Into English. (15 Pages).
European Search Report and the European Search Opinion dated Jul. 5, 2019 From the European Patent Office Re. Application No. PCT/19165448.2. (7 Pages).
Office Action dated Aug. 1, 2019 From the State Intellectual Property Office of China of the People's Republic of China Re. Application No. 201580045151.1 and Its Translation of the Notification of Office Action Into English. (8 Pages).
Search Report and Explanation dated Mar. 24, 2020 From the Servico Publico Federal, Ministerio da Economia, Instituto Nacional da Propriedade Industrial do Brasil Re. Application No. BR112016030944-8 and Its Summary in English. (5 Pages).
Search Report and Explanation dated Mar. 24, 2020 From the Servico Publico Federal, Ministerio da Economia, Instituto Nacional da Propriedade Industrial do Brasil Re. Application No. BR112016030952-9 and Its Summary in English. (5 Pages).
Search Report and Explanation dated Mar. 24, 2020 From the Sevico Publico Federal, Ministerio da Economia, Instituto Nacional da Propriedade Industrial do Brasil Re. Application No. BR112016030955-3 and Its Summary in English. (5 Pages).
Summons to Attend Oral Proceedings Pursuant to Rule 115(1) EPC Dated Sep. 24, 2020 From the European Patent Office Re. Application No. 15814472.5. (6 Pages).
Decision to Grant a Patent for Invention dated Mar. 25, 2019 From the Federal Government Institution, Federal Institute of Industrial Property of the Federal Service for Intellectual Property, Patents and Trademarks, ROSPATENT of the Russian Federation Re. Application No. 2017102236 and Its Translation Into English. (18 Pages).
Decision to Grant a Patent for Invention dated Mar. 25, 2019 From the Federal Government Institution, Federal Institute of Industrial

(56) References Cited

OTHER PUBLICATIONS

Property of the Federal Service for Intellectual Property, Patents and Trademarks, ROSPATENT of the Russian Federation Re. Application No. 2017102235 and Its Translation Into English. (16 Pages).
Decision to Grant a Patent for Invention dated Mar. 25, 2019 From the Federal Government Institution, Federal Institute of Industrial Property of the Federal Service of Intellectual Property, Patents and Trademarks, ROSPATENT of the Russian Federation Re. Application No. 2017102233 and Its Translation Into English. (17 Pages).
Examination Report dated Apr. 8, 2019 From the Australian Government, IP Australia Re. Application No. 2015283589. (5 Pages).
Notice of Reasons for Rejection dated May 7, 2019 From the Japan Patent Office Re. Application No. 2016-576067 and Its Translation Into English. (3 Pages).
Notice of Reasons for Rejection dated May 7, 2019 From the Japan Patent Office Re. Application No. 2016-576071 and Its Translation Into English. (8 Pages).
Office Action dated Apr. 15, 2019 From the Israel Patent Office Re. Application No. 249834 and Its Translation Into English. (5 Pages).
Office Action dated Apr. 15, 2019 From the Israel Patent Office Re. Application No. 249835 and Its Translation Into English. (5 Pages).
Applicant-Initiated Interview Summary dated Apr. 5, 2018 From the U.S. Patent and Trademark Office Re. U.S. Appl. No. 15/391,896. (3 pages).
Applicant-Initiated Interview Summary dated Jan. 5, 2018 From the U.S. Patent and Trademark Office Re. U.S. Appl. No. 15/382,819. (3 pages).
Applicant-Initiated Interview Summary dated Dec. 22, 2017 From the U.S. Patent and Trademark Office Re. U.S. Appl. No. 15/312,647. (3 pages).
Applicant-Initiated Interview Summary dated Dec. 22, 2017 From the U.S. Patent and Trademark Office Re. U.S. Appl. No. 15/362,883. (3 pages).
Applicant-Initiated Interview Summary dated Mar. 22, 2018 From the U.S. Patent and Trademark Office Re. U.S. Appl. No. 15/308,370. (5 pages).
Applicant-Initiated Interview Summary dated May 22, 2017 From the U.S. Patent and Trademark Office Re. U.S. Appl. No. 15/386,182. (3 pages).
Applicant-Initiated Interview Summary dated May 23, 2017 From the U.S. Patent and Trademark Office Re. U.S. Appl. No. 15/362,841. (3 pages).
Applicant-Initiated Interview Summary dated May 23, 2017 From the U.S. Patent and Trademark Office Re. U.S. Appl. No. 15/362,883. (3pages).
Applicant-Initiated Interview Summary dated May 23, 2017 From the U.S. Patent and Trademark Office Re. Application No. 15/375,098. (3 pages).
Applicant-Initiated Interview Summary dated May 23, 2017 From the U.S. Patent and Trademark Office Re. U.S. Appl. No. 15/382,819. (3 pages).
Communication Pursuant to Article 94(3) EPC dated Sep. 5, 2018 From the European Patent Office Re. Application No. 15744363.1. (4 Pages).
Communication Pursuant to Article 94(3) EPC dated Jan. 19, 2018 From the European Patent Office Re. Application No. 15744363.1. (4 Pages).
Communication Pursuant to Article 94(3) EPC dated Jan. 22, 2018 From the European Patent Office Re. Application No. 15756490.7. (4 Pages).
Communication Pursuant to Article 94(3) EPC dated Jun. 23, 2017 From the European Patent Office Re. Application No. 11815728.8. (5 Pages).
Communication Pursuant to Article 94(3) EPC dated Apr. 26, 2018 From the European Patent Office Re. Application No. 11815728.8. (4 Pages).
Communication Pursuant to Article 94(3) EPC dated Feb. 26, 2018 From the European Patent Office Re. Application No. 15753782.0. (6 Pages).

Communication Relating to the Results of the Partial International Search dated May 18, 2012 From the International Searching Authority Re. Application No. PCT/IL2011/050071.
Communication Relating to the Results of the Partial International Search dated Oct. 22, 2015 From the International Searching Authority Re. Application No. PCT/IL2015/050673.
Communication Relating to the Results of the Partial International Search dated Sep. 24, 2015 From the International Searching Authority Re. Application No. PCT/IL2015/050677.
Examiner-Initiated Interview Summary dated Nov. 2, 2017 From the U.S. Patent and Trademark Officer Re. U.S. Appl. No. 15/382,819. (2 pages).
International Preliminary Report on Patentability dated Jul. 2, 2013 From the International Preliminary Examining Authority Re. Application No. PCT/112011/050071.
International Preliminary Report on Patentability dated Jan. 12, 2017 From the International Bureau of WIPO Re. Application No. PCT/IL2015/050673. (15 Pages).
International Preliminary Report on Patentability dated Jan. 12, 2017 From the International Bureau of WIPO Re. Application No. PCT/IL2015/050674. (11 Pages).
International Preliminary Report on Patentability dated Jan. 12, 2017 From the International Bureau of WIPO Re. Application No. PCT/IL2015/050675. (8 Pages).
International Preliminary Report on Patentability dated Jan. 12, 2017 From the International Bureau of WIPO Re. Application No. PCT/IL2015/050677. (13 Pages).
International Preliminary Report on Patentability dated Jan. 12, 2017 From the International Bureau of WIPO Re. Application No. PCT/IL2015/050678. (12 Pages).
International Preliminary Report on Patentability dated Jan. 12, 2017 From the International Bureau of WIPO Re. Application No. PCT/IL2015/50676. (11 Pages).
International Preliminary Report on Patentability dated Jul. 19, 2018 From the International Bureau of WIPO Re. Application No. PCT/IL2017/050014. (10 Pages).
International Search Report and the Written Opinion dated Feb. 2, 2016 From the International Searching Authority Re. Application No. PCT/IL2015/050673.
International Search Report and the Written Opinion dated Dec. 3, 2015 From the International Searching Authority Re. Application No. PCT/IL2015/050677.
International Search Report and the Written Opinion dated Jan. 7, 2016 From the International Searching Authority Re. Application No. PCT/IL2015/050675.
International Search Report and the Written Opinion dated Dec. 10, 2015 From the International Searching Authority Re. Application No. PCT/IL2015/050674.
International Search Report and the Written Opinion dated Oct. 19, 2012 From the International Searching Authority Re. Application No. PCT/IL2011/050071.
International Search Report and the Written Opinion dated Jan. 20, 2016 From the International Searching Authority Re. Application No. PCT/IL2015/50676.
International Search Report and the Written Opinion dated Oct. 22, 2015 From the International Searching Authority Re. Application No. PCT/IL2015/050678.
International Search Report and the Written Opinion dated Mar. 27, 2017 From the International Searching Authority Re. Application No. PCT/IL2017/050014. (16 Pages).
Notice of Allowance dated Jun. 1, 2017 From the U.S. Patent and Trademark Office Re. U.S. Appl. No. 13/997,302. (24 Pages).
Notice of Allowance dated Mar. 1, 2018 From the U.S. Patent and Trademark Office Re. U.S. Appl. No. 15/312,647. (24 Pages).
Notice of Allowance dated Apr. 23, 2018 From the U.S. Patent and Trademark Office Re. U.S. Appl. No. 15/382,819. (17 pages).
Notice of Allowance dated Oct. 23, 2018 From the U.S. Patent and Trademark Office Re. U.S. Appl. No. 15/391,896. (16 pages).
Notification of Office Action dated Aug. 2, 2018 From the State Intellectual Property Office of the People's Republic of China Re. Application No. 201580045151.1 and Its Summary in English. (6 pages).

(56) References Cited

OTHER PUBLICATIONS

Office Action dated Jan. 19, 2017 From the Israel Patent Office Re. Application No. 227102 and Its Translation Into English. (5 Pages).
Office Action dated Dec. 21, 2017 From the Israel Patent Office Re. Application No. 227102 and Its Translation Into English. (4 Pages).
Office Action dated Jun. 22, 2016 From the Israel Patent Office Re. Application No. 227102 and Its Translation Into English.
Official Action dated Jun. 1, 2017 From the U.S. Patent and Trademark Office Re. U.S. Appl. No. 15/375,098. (42 pages).
Official Action dated Nov. 1, 2017 From the U.S. Patent and Trademark Office Re. U.S. Appl. No. 15/382,819. (45 pages).
Official Action dated Apr. 6, 2017 From the U.S. Patent and Trademark Office Re. U.S. Appl. No. 15/362,841. (35 pages).
Official Action dated Mar. 9, 2017 From the U.S. Patent and Trademark Office Re. U.S. Appl. No. 15/386,182. (24 pages).
Official Action dated Apr. 10, 2017 From the U.S. Patent and Trademark Office Re. U.S. Appl. No. 15/362,883. (33 pages).
Official Action dated Dec. 12, 2017 From the U.S. Patent and Trademark Office Re. U.S. Appl. No. 15/308,370. (27 pages).
Official Action dated Mar. 13, 2017 From the U.S. Patent and Trademark Office Re. U.S. Appl. No. 15/391,896. (22 pages).
Official Action dated Mar. 14, 2018 From the U.S. Patent and Trademark Office Re. U.S. Appl. No. 15/362,883. (21 pages).
Official Action dated Aug. 18, 2017 From the U.S. Patent and Trademark Office Re. U.S. Appl. No. 15/308,370. (56 pages).
Official Action dated Apr. 20, 2017 From the U.S. Patent and Trademark Office Re. U.S. Appl. No. 15/382,819. (30 pages).
Official Action dated Sep. 22, 2017 From the U.S. Patent and Trademark Office Re. U.S. Appl. No. 15/362,883. (43 pages).
Official Action dated Jan. 25, 2018 From the U.S. Patent and Trademark Office Re. U.S. Appl. No. 15/375,098. (37 pages).
Official Action dated Dec. 26, 2017 From the U.S. Patent and Trademark Office Re. U.S. Appl. No. 15/391,896. (53 pages).
Official Action dated Sep. 28, 2017 From the U.S. Patent and Trademark Office Re. U.S. Appl. No. 15/312,647. (57 pages).
Official Action dated Jan. 30, 2017 From the U.S. Patent and Trademark Office Re. U.S. Appl. No. 13/997,302. (23 pages).
Official Action dated Sep. 30, 2016 From the U.S. Patent and Trademark Office Re. U.S. Appl. No. 13/997,302.
Official Action dated May 31, 2018 From the U.S. Patent and Trademark Office Re. U.S. Appl. No. 15/391,896. (17 pages).
Requisition by the Examiner dated Nov. 16, 2017 From the Innovation, Science and Economic Development Canada, Canadian Intellectual Property Office Re. Application No. 2,822,738. (4 Pages).
Restriction Official Action dated Aug. 7, 2017 From the U.S. Patent and Trademark Office Re.U.S. Appl. No. 15/312,647. (8 pages).
Restriction Official Action dated Jul. 8, 2016 From the U.S. Patent and Trademark Office Re. U.S. Appl. No. 13/997,302.
Supplementary European Search Report and the European Search Opinion dated Mar. 19, 2018 From the European Patent Office Re. Application No. 15814472.5. (9 Pages).
Supplementary European Search Report and the European Search Opinion dated Mar. 19, 2018 From the European Patent Office Re. Application No. 15815982.2. (8 Pages).
Translation Dated Aug. 14, 2018 of Notification of Office Action dated Aug. 2, 2018 From the State Intellectual Property Office of the People's Republic of China Re. Application No. 201580045151.1. (3 Pages).
Written Opinion dated Apr. 22, 2013 From the International Preliminary Examining Authority Re. Application No. PCT/IL2011/050071.
AAAAI "Inhaled Asthma Medications: Tips to Remember", American Academy of Allergy Asthma & Immunology, AAAAI, 4 P., 2013.
Abrams et al. "Vaporization as a Smokeless Cannabis Delivery System: A Pilot Study", Clinical Pharmacology & Therapeutics, 82(5): 572-578, Advance Online Publication Apr. 11, 2007.
Assaf et al. "Pre- and Post-Conditioning Treatment With an Ultra-Low Dose of [Delta]-Tetrahydrocannabinol (THC) Protects Against Pentylenetetrazole (PTZ)-Induced Cognitive Damage", Behavioral Brain Research, 220(1): 194-201, Jun. 2011.
Bhattacharyya et al. "Opposite Effects of Delta-9-Tetrahydrocannabinol and Cannabidiol on Human Brain Function and Psychopathology", Neuropsychopharmacology, 35: 764-774, 2010.
Boden et al. "The Effects of Cannabis Use Expectancies on Self-Initiated Cannabis Cessation", Addiction, 108: 1649-1657, 2013.
Carter et al. "Medicinal Cannabis: Rational Guidelines for Dosing", IDrugs, 7(5): 464-470, May 2004.
Cohen et al. "Modelling of the Concentration—Effect Relationship of THC on Central Nervous System Parameters and Heart Rate—Insight Into Its Mechanisms of Action and a Tool for Clinical Research and Development of Cannabinoids", Journal of Pharmacology, 22(7): 717-726, Sep. 2008.
Das et al. "Effects of 9-Ene-Tetrahydrocannabinol on Expression of Beta-Type Transforming Growth Factors, Insulin-Like Growth Factor-I and C-Myc Genes in the Mouse Uterus", The Journal of Steroid Biochemistry and Molecular Biology, 45(6): 459-465, 1993.
Eisenberg et al. "The Pharmacokinetics, Efficacy, Safety, and Ease of Use of a Novel Portable Metered-Dose Cannabis Inhaler in Patients With Chronic Neuropathic Pain: A Phase 1a Study", Journal of Pain & Palliative Care Pharmacotherapy, 28(3): 216-225, Published Online Aug. 13, 2014.
Farrimond et al. "Cannabinol and Cannabidiol Exert Opposing Effects on Rat Feeding Patterns", Psychopharmacology, 223: 117-129, 2012.
FDA "Guidance for Industry. Population Phaymacokinetics", U.S. Department of Health and Human Services, Food and Drug Administration (FDA), Center for Drug Evaluation and Research (CDER), Center for Biological Evaluation and Research (CBER), CP 1: 1-31, Feb. 1999.
Fishbein et al. "Long-Term Behavioral and Biochemical Effects of an Ultra-Low Dose of [Delta]sup9-Tetrahydrocannabinol (THC): Neuroprotection and ERK Signaling", Experimental Brain research, 221(4): 437-448, Published Online Jul. 22, 2012.
Hazekamp et al. "Bedrocan®—Stimulating the Development of Herbal Cannabis-Based Products", Bedromedical Presentation, 2013.
Hazekamp et al. "Evaluation of a Vaporizing (Volcano®) for the Pulmonary Administration of Tetrahydrocannibinol", Journal of Pharmaceutical Sciences, 95(6): 1308-1317, Jun. 2006.
Hazekamp et al. "The Medical Use of Cannabis and Cannabinoids—An International Cross-Sectional Survey on Administration Forms", Journal of Psychoactive Drugs, 45(3): 199-210, 2013.
Herbalizer "Herbalizer, the New Vaporization Experience", 6 P., Jun. 7, 2013.
Ibrahim et al. "Inhilation Drug Delivery Devices: Technology Update", Medical Devices: Evidence and Research, 8: 131-139, Feb. 12, 2015.
Jamontt et al. "The Effects of Delta[9]-Tetrahydrocannabino and Cannabidiol Alone and in Combination on Damage, Inflammation and In Vitro Motility Disturbances in Rat Colitis", British Journal of Pharmacology, 160: 712-723, 2010.
Jang et al. "Thermophysical Properties of Porous SiC Ceramics Fabricated by Pressureless Sintering", Science and Technology of Advanced Materials, 8(7): 655-659, Nov. 30, 2007.
Lanz et al. "Medicinal Cannabis: In Vitro Validation of Vaporizers for the Smoke-Free Inhalation of Cannabis", PLOS One, 11(1): e01472386-1-e0147286-18, Jan. 19, 2016.
McPartland et al. "Are Cannabidiol and Delta9-Tetrahydrocannabivarin Negative Modulators of the Endocannabinoid System? A Systematic Review", British Journal of Pharmacolog, 172(3): 737-753, Published Online Jan. 8, 2015.
Mechoulam et al. "Cannabidiol—Recent Advances", Chemistry & Biodiversity, 4: 1678-1692, 2007.
Norwood et al. "Best Practices for Extractables and Leachables in Orally Inhaled and Nasal Drug Products: An Overview of the PQRI Recommendations", Pharmaceutical Research, 25(4): 727-739, Published Online Jan. 9, 2008.
Pertwee "The Diverse CB1 and CB2 Receptor Pharmacology of Three Plant Cannabinoids: Delta[9]-Tetrahydrocannabinol, Cannabidiol and Delta[9]—Tetrahydrocannabivarin", British Journal of Pharmacology, 153: 199-215, 2008.

(56) References Cited

OTHER PUBLICATIONS

Pomahacova et al. "Cannabis Smoke Condensate III: The Cannabinoid Content of Vaporised Cannabis Sativa", Inhalation Toxicology, 21(13): 1108-1112, Nov. 1, 2009.
Rabinowitz et al. "Fast Onset Medications Through Thermally Generated Aerosols", The Journal of Pharmacological and Experimental Therapeutics, 309(2): 769-775, Published Online Jan. 29, 2004.
Rau "The Inhalation of Drugs: Advantages and Problems", Respiratory Care, 50(3): 367-382, Mar. 2005.
Syge Medical "The World's First Metered Dose Pharmaceutical Grade Medical Cannabis Inhaler", Syge Medical™, Press Kit, p. 1-8, 2015.
Van Gerven "Biomarkers to Assess Adverse Drug Effects on the CNS", Centre for Human Drug Research, CHDR, Poster-Session, Slide-Show, 25 P., 2013.
Van Hell et al. "Evidence for Involvement of the Insula in the Psychotropic Effects of THC in Humans: A Double-Blind, Randomized Pharamcological MRI Study", International Journal of Neuropharmacology, 14: 1377-1388, 2011.
Vann et al. "Divergent Effects of Cannabidiol on the Discriminative Stimulus and Place Conditioning Effects of Delta 9-Tetrahydrocannabiol", Drug and Alcohol Dependence, 94(1-3): 191-198, Apr. 1, 2008.
Vemuri et al. "Pharmacotherapeutic Targeting of the Endocannabinoid Signaling System: Drugs for Obesity and the Metabolic Syndrome", Physiology & Behavior, 93: 671-686, 2008.
Wallace et al. "Efficacy of Inhaled Cannabis on Painful Diabetic Neuropathy", The Journal of Pain, 169(7): 616-627, Published Online Apr. 3, 2015.
Ware et al. "Smoked Cannabis for Chronic Neuropathic Pain: A Randomized Controlled Trial", Canadian Medical Association Journal, CMAJ, 182(14): E694- E701, Published Online Aug. 30, 2010.
Wilsey et al. "Low-Dose Vaporized Cannabis Significantly Improves Neuropathic Pain", The Journal of Pain, 14(2): 136-148, Published Online Dec. 13, 2012. 'Discussion', Last Para.
Zuurman et al. "Biomarkers for the Effects of Cannabis and THC in Healthy Volunteers", British Journal of Clinical Pharmacology, 67(1): 5-21, 2008.
Zuurman et al. "Effect of Intrapulmonary Tetrahydrocannabinol Administration in Humans", Journal of Psychopharmacology, 22(7): 707-716, 2008.
European Search Report and the European Search Opinion dated Nov. 20, 2020 From the European Patent Office Re. Application No. 20192870.2. (7 Pages).
Official Action dated Jul. 28, 2020 from the U.S. Patent and Trademark Office Re. U.S. Appl. No. 16/131,079. (102 pages).
Communication Pursuant to Article 94(3) EPC dated Sep. 2, 2020 From the European Patent Office Re. Application No. 15756490.7. (5 Pages).
Search Report and Explanations dated Apr. 15, 2020 From the Servico Publico Federal, Ministerio da Economia, Instituto Nacional da Propriedade Industrial do Brasil Re. Application No. BR112016030829-8 and Its Summary in English. (5 Pages).
European Search Report and the European Search Opinion dated Mar. 26, 2020 From the European Patent Office Re. Application No. 20150198.8. (9 Pages).
Final Official Action dated May 4, 2020 from the U.S. Patent and Trademark Office Re. U.S. Appl. No. 15/690,323. (55 pages).
International Search Report and the Written Opinion dated May 3, 2020 From the International Searching Authority Re. Application No. PCT/IL2020/050151. (18 Pages).
Requisition by the Examiner dated Aug. 6, 2019 From the Innovation, Science and Economic Development Canada, Canadian Intellectual Property Office Re. Application No. 2,822,738.(4 Pages).
International Preliminary Report on Patentability dated Aug. 27, 2020 From the International Bureau of WIPO Re. Application No. PCT/IL2019/050178. (8 Pages).
Official Action dated Sep. 1, 2020 from the U.S. Patent and Trademark Office Re. U.S. Appl. No. 15/690,323. (14 pages).
Requisition by the Examiner dated Aug. 13, 2020 From the Innovation, Science and Economic Development Canada, Canadian Intellectual Property Office Re. Application No. 2,822,738. (3 Pages).
Notification of Office Action and Search Report dated Aug. 13, 2020 From the State Intellectual Property Office of the People's Republic of China Re. Application No. 201580045151.1 and Its Translation of Office Action Into English. (9 Pages).
Notification of Office Action dated Feb. 3, 2019 From the State Intellectual Property Office of the People's Republic of China Re. Application No. 201580045136.7 and Its Translation Into English. (4 Pages).
Notification of Office Action dated Feb. 11, 2019 From the State Intellectual Property Office of the People's Republic of China Re. Application No. 201580045638.X and Its Translation Into English. (4 Pages).
Notification of Office Action dated Feb. 11, 2019 From the State Intellectual Property Office of the People's Republic of China Re. Application No. 201580046016.9 and Its Translation Into English. (4 Pages).
Communication Pursuant to Article 94(3) EPC dated Nov. 12, 2018 From the European Patent Office Re. Application No. 15814472.5. (5 Pages).
Communication Pursuant to Article 94(3) EPC dated Nov. 12, 2018 From the European Patent Office Re. Application No. 15815982.2. (4 Pages).
Communication Pursuant to Article 94(3) EPC dated Nov. 19, 2018 From the European Patent Office Re. Application No. 15756490.7. (4 Pages).
Request for Examination and Search Report dated Nov. 23, 2018 From the Federal Government Institution, Federal Institute of Industrial Property of the Federal Service for Intellectual Property, Patents and Trademarks of the Russian Federation Re. Application No. 2017102235 and Its Translation Into English. (9 Pages).
Requisition by the Examiner dated Nov. 2, 2018 From the Innovation, Science and Economic Development Canada, Canadian Intellectual Property Office Re. Application No. 2,822,738. (4 Pages).
Communication Pursuant to Article 94(3) EPC dated Aug. 4, 2020 From the European Patent Office Re. Application No. 15815982.2. (5 Pages).
Decision to Grant a Patent for Invention and Search Report dated Oct. 29, 2019 From the (ROSPATENT), Federal Government Institution of Industrial Property of the Federal Service of Intellectual Property, Patents and Trademark of the Russian Federation Re. Application No. 2019115942.and Its Translation Into English. (16 Pages).
Communication Pursuant to Article 94(3) EPC dated Feb. 6, 2019 From the European Patent Office Re. Application No. 15753782.0. (6 Pages).
Official Action dated Feb. 4, 2019 From the U.S. Patent and Trademark Office Re. U.S. Appl. No. 15/362,883. (53 pages).
Request for Examination and Search Report dated Feb. 26, 2020 From the Federal Government Institution, Federal Institute of Industrial Property of the Federal Service of Intellectual Property, Patents and Trademarks of the Russian Federation, FIPS Re. Application No. 2019115949 and Its Translation Into English. (11 Pages).
Notice of Reason(s) for Rejection dated Jan. 26, 2021 From the Japan Patent Office Re. Application No. 2020-003761 and Its Translation Into English. (7 Pages).
Request for Examination dated Feb. 4, 2021 From the (ROSPATENT), Federal Government Institution of Industrial Property of the Federal Service of Intellectual Property, Patents and Trademark of the Russian Federation Re. Application No. 2020130235 and Its Translation Into English. (5 Pages).
Examination Report dated Apr. 20, 2021 From the Instituto Mexicano de la Propiedad Industrial, Direccion Divisional de Patentes Re. Application No. MX/a/2017/000057 together with an English Summary. (5 Pages).
European Search Report and the European Search Opinion dated Apr. 8, 2021 From the European Patent Office Re. Application No. 21159548.3. (7 Pages).

(56) References Cited

OTHER PUBLICATIONS

International Preliminary Report on Patentability dated May 6, 2021, From the International Bureasu of WIPO Re. Application No. PCT/IL2019/051163. (16 Pages).
Notice of Reason(s) for Rejection dated Jun. 1, 2021 From the Japan Patent Office Re. Application No. 2020-1101083 and Its Translation Into English (112 Pages).
Final Official Action dated Feb. 22, 2021 From the U.S. Patent and Trademark Office Re. U.S. Appl. No. 16/131,079. (60 Pages).
Notification of Office Action and Search Report dated Mar. 1, 2021 From the State Intellectual Property Office of the People's Republic of China Re. Application No. 201580045151.1 and Its Translation of Office Action Into English. (8 Pages).
Notice of Reason(s) for Rejection dated Jan. 26, 2021 From the Japan Patent Office Re. Application No. 2019-231996 and Its Translation Into English.(10 Pages).
Examination Report dated Jan. 13, 2021 From the Instituto Mexicano de la Propiedad Industrial, Secretario de Economia, Dioreccion Divisional de Patentes Re. Application No. MX/a/2017/000057. (6 Pages).
Request for Examination and Search Report dated Feb. 4, 2021 From the Federal Government Institution, Federal Institute of Industrial Property of the Federal Service of Intellectual Property, Patents and Trademarks of the Russian Federation, FIPS Re. Application No. 2020130235 and Its Translation of Office Action Into English. (9 Pages).
Patent Examination Report dated Nov. 23, 2020 From the Australian Government, IP Australia Re. Application No. 2019229370. (4 Pages).
European Search Report and the European Search Opinion dated Apr. 22, 2021 (Replacing European Searchh Report dated Nov. 20, 2020) From the European Patent Office Re. Application No. 20192870.2. (14 Pages).
Notice of Reasons for Rejection dated Mar. 9, 2021 From the Japan Patent Office Re. Application No. 2016-576068 and Its Translation Into English. (17 Pages).
Examination Report dated Jan. 29, 2022 from the Australian Patent Office Re. Application No. 2021202185. (5 pages).
Ground(s) of Reason of Rejection dated Jan. 21, 2022 From the Korean Intellectual Property Office Re. Application No. 10-2017-70023243 and its Translation into English. (13 Pages).
Notification of Office Action and Search Report dated Jan. 20, 2022From the State Intellectual Property Office of the People's Republic of China Re. Application No. 202011200160.2. (6 Pages).
Notice of Reasons for Rejection dated Feb. 22, 2022 From the Korean Intellectual Property Office Re. Application No. 10-2017-7002721 and Its Translation Into English. (5 Pages).
Examination Report dated Aug. 6, 2021 From the Instituto Mexicano de la Propiedad Industrial, Direccion Divisional de Patentes Re. Application No. MX/a/2017/000057 and Its Translation Into English. (10 Pages).
International Preliminary Report on Patentability dated Aug. 19, 2021 From the International Bureau of WIPO Re. Application No. PCT/IL2020/050151. (7 Pages).
Official Action dated Aug. 5, 2021 from the U.S. Patent and Trademark Office Re. U.S. Appl. No. 16/030,967. (163 pages).
Patent Examination Report dated Aug. 13, 2021 From the Australian Government, IP Australia Re. Application No. 2020205271. (7 Pages).
Requisition by the Examiner dated Aug. 19, 2021 From the Innovation, Science and Economic Development Canada, Canadian Intellectual Property Office Re. Application No. 2,953,074. (16 Pages).
Requisition by the Examiner dated Aug. 26, 2021 From the Innovation, Science and Economic Development Canada, Canadian Intellectual Property Office Re. Application No. 2,953,082. (28 Pages).
Requisition by the Examiner dated Sep. 28, 2021 From the Innovation, Science and Economic Development Canada, Canadian Intellectual Property Office Re. Application No. 2,953,069. (4 Pages).
Requisition by the Examiner dated Sep. 28, 2021 From the Innovation, Science and Economic Development Canada, Canadian Intellectual Property Office Re. Application No. 2,953,073. (4 Pages).
European Search Report and the European Search Opinion dated Oct. 11, 2021 From the European Patent Office Re. Application No. 21194394.9 (8 Pages).
European Search Report and the European Search Opinion dated Nov. 9, 2021 From the European Patent Office Re. Application No. 21199976.8. (8 Pages).
Notice of Allowance dated Dec. 20, 2021 from U.S. Patent and Trademark Office Re. U.S. Appl. No. 16/055,269. (158 pages).
Notice of Allowance dated Dec. 1, 2021 from the U.S. Patent and Trademark Office Re. U.S. Appl. No. 16/030,967. (21 pages).
Notice of Allowance dated Nov. 24, 2021 from the U.S. Patent and Trademark Office Re. U.S. Appl. No. 16/436,984. (124 pages).
Notice of Reason(s) for Rejection dated Oct. 12, 2021 From the Japan Patent Office Re. Application No. 2020-101083 and Its Translation Into English. (17 Pages).
Notice of Reason(s) for Rejection dated Oct. 12, 2021 From the Japan Patent Office Re. Application No. 2020-134166 and Its Translation Into English. (10 Pages).
Notification of Office Action and Search Report dated Nov. 3, 2021 From the State Intellectual Property Office of the People's Republic of China Re. Application No. 202010701980.3. (10 Pages).
Office Action dated Nov. 2, 2021 From the Israel Patent Office Re. Application No. 262376 and Its Translation Into English. (7 Pages).
Patent Examination Report dated Oct. 26, 2021 From the Australian Government, IP Australia Re. Application No. 2017204945. (3 Pages).
Supplementary European Search Report and the European Search Opinion dated Dec. 16, 2021From the European Patent Office Re. Application No. 19754583.3. (6 Pages).
Almog et al. "The Pharmacokinetics, Efficacy, and Safety of a Novel Selective-Dose Cannabis Inhaler in Patients With Chronic Pain: A Randomized, Double-Blineed, Placebo-Controlled Trial", European Journal of Pain, 24(8): 1505-1516, Published Online Jun. 12, 2020.
Requisition by the Examiner dated Mar. 11, 2022 From the Innovation, Science and Economic Development Canada, Canadian Intellectual Property Office Re. Application No. 2,953,082. (6 Pages).
European Search Report and the European Search Opinion dated Dec. 17, 2021 From the European Patent Office Re. Application No. 21196651.0. (7 Pages).
English Translation Dated Feb. 21, 2022 of Notification of Office Action and Search Report dated Jan. 20, 2022 From the State Intellectual Property Office of the People's Republic of China Re. Application No. 202011200160.2.1 Pages).
Grounds of Reason of Rejection dated Mar. 24, 2022 From the Korean Intellectual Property Office Re. Application No. 10-2017-7002682 and Its Translation Into English. (14 Pages).
Notice of Reasons for Rejection dated Mar. 22, 2022 From the Japan Patent Office Re. Application No. 2020-101083 and Its Translation Into English. (7 Pages).
Patent Examination Report dated Mar. 18, 2022 From the Australian Government, IP Australia Re. Application No. 2021204703 with claims (7 Pages).
Patent Examination Report dated Mar. 22, 2022 From the Australian Government, IP Australia Re. Application No. 2020205271 with amended Claims (8 Pages).
Requisition by the Examiner dated Mar. 29, 2022 From the Innovation, and Economic Development Canada, Canadian Intellectual Property Office Science Re. Application No. 2,953,069 with Claims (15 Pages).
Requisition by the Examiner dated Mar. 30, 2022 From the Innovation, Science and Economic Development Canada, Canadian Intellectual Property Office Re. Application No. 2,953,073 with Claims (18 Pages).

(56) References Cited

OTHER PUBLICATIONS

Requisition by the Examiner dated Apr. 4, 2022 From the Innovation, Science and Economic Development Canada, Canadian Intellectual Property Office Re. Application No. 2,953,074 with Claims. (11 Pages).
Notification of Office Action and Search Report dated Oct. 25, 2022 From the State Intellectual Property Office of the People's Republic of China Re. Application No. 202110926270.5 and Its Translation of Office Action Into English. (7 Pages).
Official Action dated Oct. 26, 2022 from the U.S. Patent and Trademark Office Re. U.S. Appl. No. 17/238,278. (156 pages).
Grasscity "How to Make Hush?, Discussion in 'Apprentice Marijuana Consuption' started by Juggalobud", Grasscity Forums, Retrieved from the Internet, Nov. 1, 2002 (17 pages).
UNODC "Recommended Methods for the Identification and Analysis of Cannabis and Cannabis Products", United Nations Office on Drugs, Crime, United Nations Publications, 1-50, Sep. 2009.
Verilife "Cannabis Trichomes: What Are They & What They Do?", Retrieved from the Internet, Nov. 29, 2021 (4 pages).
English Summary dated Jul. 20, 2022 of Notification of Office Action and Search Report dated Jun. 27, 2022 From the State Intellectual Property Office of the People's Republic of China Re. Application No. 201980081175.0. (1 Page).
Requisition by the Examiner dated May 25, 2022 From the Innovation, Science and Economic Development Canada, Canadian Intellectual Property Office Re. Application No. 3,114,582. (3 Pages).
Supplementary European Search Report and the European Search Opinion dated Jul. 12, 2022 From the European Patent Office Re. Application No. 19880500.4. (11 Pages).
Grounds of Reason of Rejection dated May 22, 2023 From the Korean Intellectual Property Office Re. Application No. 10-2022-7036865 and Its Translation Into English. (6 Pages).
Examination Report dated Jan. 11, 2023 From the Australian Goverment, IP Australia Re. Application No. 2021204365. (4 Pages).
Grounds of Reason of Rejection dated Nov. 21, 2022 From the Korean Intellectual Property Office Re. Application No. 10-2022-7038127 and Its Translation Into English. (5 Pages).
Requisition by the Examiner dated Dec. 13, 2022 From the Innovation, Science and Economic Development Canada, Canadian Intellectual Property Office Re. Application No. 2,953,074 with claims. (11 pages).
Requisition by the Examiner dated Dec. 22, 2022 From the Innovation, Science and Economic Development Canada, Canadian Intellectual Property Office Re. Application No. 3,009,599.(10 pages).
Requisition by the Examiner dated Nov. 28, 2022 From the Innovation, Science and Economic Development Canada, Canadian Intellectual Property Office Re. Application No. 2,953,069 with Claims. (17 Pages).
Requisition by the Examiner dated Nov. 28, 2022 From the Innovation, Science and Economic Development Canada, Canadian Intellectual Property Office Re. Application No. 2,953,073. (3 Pages).
Supplementary European Search Report and the European Search Opinion dated Nov. 14, 2022 From the European Patent Office Re. Application No. 20751958.8 (8 pages).
Notice of Reason(s) for Rejection dated May 16, 2023 From the Japan Patent Office Re. Application No. 2021-522537 and Its Translation Into English. (9 Pages).
Examination Report dated May 29, 2022 From the Servico Publico Federal, Ministerio da Economia, Instituto Nacional da Propriedade Industrial do Brasil RE Application No. BR12 2020 018207 5 with Pending Claims and its English Summary. (8 Pages).
English Summary dated May 4, 2023 of Decision on Rejection dated Apr. 23, 2023 From the State Intellectual Property Office of the People's Republic of China 2023 Re. Application No. 201980081175.0 (1 page).

Grounds of Reason of Rejection dated Apr. 20, 2023 From the Korean intellectual Property Office Re. Application No. 10-2022-7045372 and Its Translation Into English. (9 Pages).
Notice of Allowance dated May 2, 2023 From the U.S. Patent and Trademark Office Re. U.S. Appl. No. 17/238,278. (33 Pages).
Decision on Rejection dated Apr. 23, 2023 From the State Intellectual Property Office of the People's Republic of China Re. Application No. 201980081175.0. (8 pages).
English Summary dated Apr. 26, 2023 of Notification of Office Action dated Apr. 19, 2023 From the State Intellectual Property Office of the People's Republic of China Re. Application No. 202080027182.5. (2 pages).
Notification of Office Action and Search Report dated Apr. 13, 2023 From the State Intellectual Property Office of the People's Republic of China Re. Application No. 202080027182.5 (11 pages).
Notice of Reasons for Rejection dated Aug. 30, 2022 From the Japan Patent Office Re. Application No. 2021-175408 and Its Translation Into English. (12 Pages).
Notification of Office Action dated Jun. 23, 2022 From the State Intellectual Property Office of the People's Republic of China Re. Application No. 20200101980.3. (8 Pages).
Notice of Reasons for Rejection dated May 24, 2022 From the Japan Patent Office Re. Application No. 2020-134166 and Its Translation Into English. (10 Pages).
Decision of Rejection dated Sep. 17, 2019 From the Japan Patent Office Re. Application No. 2016-576068 and Its Translation Into English. (12 Pages).
Notification of Office Action and Search Report dated Sep. 4, 2019 From the State Intellectual Property Office of the People's Republic of China Re. Application No. 201580046016.9 and Its Translation Into English. (16 Pages).
Official Action dated Sep. 30, 2019 From the U.S. Patent and Trademark Office Re. U.S. Appl. No. 15/690,323. (123 pages).
Translation Dated Oct. 1, 2019 of Notification of Office Action dated Sep. 3, 2019 From the State Intellectual Property Office of the People's Republic of China Re. Application No. 201580045638.X. (13 Pages).
Green Machine "Structure of a leaf—Internal & External", Retrieved from google.com, 6 Pages, Sep. 2019.
Ormrod et al. "A Survey of Weed Leaf Stomata and Trichomes", Canadian Journal of Plant Science, 48(2): 197-209, 1968.
Science "Nettle Leaf Trichromes", Retrieved fromsciencesource.com, 1 Page, Sep. 2019.
Examination Report dated Jan. 21, 2019 From the Australian Government, IP Australia Re. Application No. 2015283593. (4 Pages).
Office Action dated Jan. 17, 2019 From the Israel Patent Office Re. Application No. 260852 and Its Translation Into English. (6 Pages).
Notification of Office Action and Search Report dated Jun. 27, 2022 From the State Intellectual Property Office of the People's Republic of China Re. Application No. 201980081175.0. (13 Pages).
Perry et al.
Notice of Reason(s) for Rejection dated Jun. 13, 2023 From the Japan Patent Office Re. Application No. 2022-115378. (4 pages).
Communication Pursuant to Article 94(3) EPC dated Feb. 6, 2013 From teh European Office Re. Application No. 20150198.8 (7 Pages).
Notice of Reason(s) for Rejection dated Mar. 7, 2023 From the Japan Patent Office Re. Application No. 2021-175408 and Its Translation Into English. (5 Pages).
Official Action dated Mar. 30, 2023 From the U.S. Patent and Trademark Office Re. U.S. Appl. No. 17/679,190. (287 Pages).
Request for Examination and Search Report dated Mar. 10, 2023 From the (ROSPATENT), Federal Government Institution of Industrial Property of the Federal Service of Intellectual Property, Patents and Trademark of the Russian Federation Re. Application No. 2021125574. (9 Pages).
Request for Examination and Search Report dated Feb. 16, 2023 From the (ROSPATENT), Federal Government Institution of Industrial Property of the Federal Service of Intellectual Property, Patents and Trademark of the Russian Federation Re. Application No. 202111628 and its Summary in English.(12 Pages).

(56) References Cited

OTHER PUBLICATIONS

Translation Dated Apr. 10, 2023 of Request for Examination and Search Report dated Mar. 10, 2023 From the (ROSPATENT), Federal Government Institution of Industrial Property of the Federal Service of Intellectual Property, Patents and Trademark of the Russian Federation Re. Application No. 2021125574. (5 Pages).
Translation Dated Mar. 30, 2023 of Request for Examination and Search Report dated Feb. 16, 2023 From the (ROSPATENT), Federal Government Institution of Industrial Property of the Federal Service of Intellectual Property, Patents and Trademark of the Russian Federation Re. Application No. 202111628 and its Summary in English.(7 Pages).
Supplementary European Search Report and the European Search Opinion dated Aug. 19, 2019 From the European Patent Office Re. Application No. 17735927.0. (8 Pages).
Examination Report dated Jan. 15, 2019 From the Australian Government, IP Australia Re. Application No. 2015283594. (4 Pages).
Examination Report dated Feb. 20, 2020 From the Australian Government, IP Australia Re. Application No. 2015283590. (6 Pages), Jul. 7, 2023.
Notification of Office Action and Search Report dated Feb. 3, 2020 From the State Intellectual Property Office of the People's Republic of China Re. Application No. 201580045151.1. (4 Pages).
Pre-Appeal Examination Report dated Feb. 6, 2020 From the Japan Patent Office Re. Application No. 2016-576068 and Its Translation Into English.
Translation of Notification Dated Feb. 20, 2020 From OA dated Feb. 3, 2020 From the State Intellectual Property Office of the People's Republic of China Re. Application No. 201580045. (4 Pages).
Examination Report dated Sep. 14, 2020 From the Australian Government, IP Australia Re. Application No. 2019229369. (4 Pages).
Patent Examination Report dated Sep. 14, 2020 From the Australian Government, IP Australia Re. Application No. 2019275594. (4 Pages).
Examination Report dated Feb. 5, 2020 From the Instituti Mexicano de la Propiedad Industrial, IMPI, Direccion Divisional de Patentes Re. Application No. MX/a/2017/000056 and Its Translation Into English. (4 Pages).
Examination Report dated Jan. 30, 2020 From the Instituto Mexicano de la Propiedade Industrial, IMPI, Direccion Divisional de Patentes Re. Application No. MX/a/2017/000055 and Its Translation Into English. (5 Pages).

Notice of Reasons for Rejection dated Feb. 4, 2020 From the Japan Patent Office Re. Application No. 2016-576066 and Its Translation Into English. (6 Pages).
Request for Examination dated Jan. 28, 2020 From the Federal Government Institution, Federal Institute of Industrial Property of the Federal Service or Intellectual Property. Patents and Trademark of the Russian Federation Re. Application No. 2017102234 and Its Translation Into English. (14 Pages).
Notification of Office Action dated Feb. 27, 2019 From the State Intellectual Property Office of the People's Republic of China Re. Application No. 201580045151.1 and Its Translation into English. (6 Pages).
Translation for the Rejection of Claim 1 Dated May 11, 2023 of Notification of Office Action Dated Apr. 13, 2023 From the State Intellectual Property Office of the People's Republic of China Re. Application No. 202080027182.5. (1 Page).
Request for Examination dated Dec. 12, 2018 From the Federal Government Institution, Federal Institute of Industrial Property of the Federal Service or Intellectual Property, Patents and Trademark of the Russian Federation Re. Application No. 2017102234 and its Translation Into English. (9 Pages).
International Search Report and the Written Opinion dated May 23, 2019 From the International Searching Authority Re. Application No. PCT/IL2019/050178. (15 Pages).
Notice of Reasons for Rejection dated May 21, 2019 From the Japan Patent Office Re. Application No. 2016-576066 and Its Translation Into English. (12 Pages).
McPartland et al. "Affinity and Efficacy Studies of Tetrahydrocannabinolic Acid A at Cannabinoid Receptor Types One and Two", Cannabis and Cannabinoid Research, 2(1): 87-95, May 2017.
Official Action dated Aug. 3, 2023 from the US Patent and Trademark Office Re. U.S. Appl. No. 16/969,612. (271 pages).
Requisition by the Examiner dated Jul. 5, 2023 From the Innovation, Science and Economic Development Canada, Canadian Intellectual Property Office Re. Application No. 2,953,073. (3 pages).
Requisition by the Examiner dated Jun. 27, 2023 From the Innovation, Science and Economic Development Canada, Canadian Intellectual Property Office Re. Application No. 3,114,582. (3 pages).
Translation dated Jun. 23, 2023 of Notice of Reason(s) for Rejection dated Jun. 13, 2023 From the Japan Patent Office Re. Application No. 2022-115378. (4 pages).

\* cited by examiner

```
        ┌─────────────────────────────────────┐
        │ Obtaining, in real time, a personal │
        │ pharmacodynamic parameter from the  │
 1201   │ patient, (optionally using a sensor and/or │
        │ input received on a patient interface) │
        └─────────────────────────────────────┘
                         │
                         ▼
        ┌─────────────────────────────────────┐
        │ Optionally modifying the dose and/or│
 1203   │ regimen according to the parameter, to │
        │      achieve a preselected          │
        │       pharmacodynamic effect        │
        └─────────────────────────────────────┘
```

FIG. 3

LOW DOSE THERAPEUTIC TREATMENT

RELATED APPLICATIONS

This application is a National Phase of PCT Patent Application No. PCT/IL2017/050014 having International filing date of Jan. 5, 2017, which claims the benefit of priority under 35 USC 119(e) of U.S. Provisional Patent Applications No. 62/275,314 filed on Jan. 6, 2016. The contents of the above applications are all incorporated by reference as if fully set forth herein in their entirety.

FIELD AND BACKGROUND OF THE INVENTION

The present invention, in some embodiments thereof, relates to delivery of a low dose of THC through inhalation, and, more particularly, but not exclusively, to methods, devices and systems for delivering a dose of between 0.2-2 mg THC through inhalation.

Publication titled "The Pharmacokinetics, Efficacy, Safety, and Ease of Use of a Novel Portable Metered-Dose Cannabis Inhaler in Patients With Chronic Neuropathic Pain: A Phase 1a Study" (J Pain Palliat Care Pharmacother. 2014 Sep.; 28(3):216-25. doi: 10.3109/15360288.2014.941130. Epub 2014 Aug. 13.) discloses: "Chronic neuropathic pain is often refractory to standard pharmacological treatments. Although growing evidence supports the use of inhaled cannabis for neuropathic pain, the lack of standard inhaled dosing plays a major obstacle in cannabis becoming a "main stream" pharmacological treatment for neuropathic pain. The objective of this study was to explore the pharmacokinetics, safety, tolerability, efficacy, and ease of use of a novel portable thermal-metered-dose inhaler (tMDI) for cannabis in a cohort of eight patients suffering from chronic neuropathic pain and on a stable analgesic regimen including medicinal cannabis. In a single-dose, open-label study, patients inhaled a single 15.1±0.1 mg dose of cannabis using the Syqe Inhaler device. Blood samples for Δ(9)-tetrahydrocannabinol (THC) and 11-hydroxy-Δ(9)-THC were taken at baseline and up to 120 minutes. Pain intensity (0-10 VAS), adverse events, and satisfaction score were monitored following the inhalation. A uniform pharmacokinetic profile was exhibited across all participants (Δ(9)-THC plasma Cmax±SD was 38±10 ng/mL, Tmax±SD was 3±1 minutes, $AUC_0 \rightarrow infinity \pm SD$ was 607±200 ng·min/mL). Higher plasma Cmax increase per mg Δ(9)-THC administered (12.3 ng/mL/mg THC) and lower interindividual variability of Cmax (25.3%), compared with reported alternative modes of THC delivery, were measured. A significant 45% reduction in pain intensity was noted 20 minutes post inhalation (P=0.001), turning back to baseline within 90 minutes.

Tolerable, lightheadedness, lasting 15-30 minutes and requiring no intervention, was the only reported adverse event. This trial suggests the potential use of the Syqe Inhaler device as a smokeless delivery system of medicinal cannabis, producing a Δ(9)-THC pharmacokinetic profile with low interindividual variation of Cmax, achieving pharmaceutical standards for inhaled drugs."(Abstract)

Publication titled "Efficacy of Inhaled Cannabis on Painful Diabetic Neuropathy" (J Pain. 2015 July; 16(7):616-27. doi: 10.1016/j.jpain.2015.03.008. Epub 2015 Apr. 3.) discloses "A randomized, double-blinded, placebo controlled crossover study was conducted in 16 patients with painful diabetic peripheral neuropathy to assess the short-term efficacy and tolerability of inhaled cannabis. In a crossover design, each participant was exposed to 4 single dosing sessions of placebo or to low (1% tetrahydrocannabinol [THC]), medium (4% THC), or high (7% THC) doses of cannabis. Baseline spontaneous pain, evoked pain, and cognitive testing were performed. Subjects were then administered aerosolized cannabis or placebo and the pain intensity and subjective "highness" score was measured at 5, 15, 30, 45, and 60 minutes and then every 30 minutes for an additional 3 hours. Cognitive testing was performed at 5 and 30 minutes and then every 30 minutes for an additional 3 hours. The primary analysis compared differences in spontaneous pain over time between doses using linear mixed effects models. There was a significant difference in spontaneous pain scores between doses (P<0.001). Specific significant comparisons were placebo versus low, medium, and high doses (P=0.031, 0.04, and <0.001, respectively) and high versus low and medium doses (both P<0.001). There was a significant effect of the high dose on foam brush and von Frey evoked pain (both P<0.001). There was a significant negative effect (impaired performance) of the high dose on 2 of the 3 neuropsychological tests (Paced Auditory Serial Addition Test, Trail Making Test Part B." (Abstract)

Publication titled "Low-dose vaporized cannabis significantly improves neuropathic pain." (J Pain. 2013 February; 14(2):136-48. doi: 10.1016/j.jpain.2012.10.009. Epub 2012 Dec. 11.) discloses "We conducted a double-blind, placebo-controlled, crossover study evaluating the analgesic efficacy of vaporized cannabis in subjects, the majority of whom were experiencing neuropathic pain despite traditional treatment. Thirty-nine patients with central and peripheral neuropathic pain underwent a standardized procedure for inhaling medium-dose (3.53%), low-dose (1.29%), or placebo cannabis with the primary outcome being visual analog scale pain intensity. Psychoactive side effects and neuropsychological performance were also evaluated. Mixed-effects regression models demonstrated an analgesic response to vaporized cannabis. There was no significant difference between the 2 active dose groups' results (P>0.7). The number needed to treat (NNT) to achieve 30% pain reduction was 3.2 for placebo versus low-dose, 2.9 for placebo versus medium-dose, and 25 for medium-versus low-dose. As these NNTs are comparable to those of traditional neuropathic pain medications, cannabis has analgesic efficacy with the low dose being as effective a pain reliever as the medium dose. Psychoactive effects were minimal and well tolerated, and neuropsychological effects were of limited duration and readily reversible within 1 to 2 hours. Vaporized cannabis, even at low doses, may present an effective option for patients with treatment-resistant neuropathic pain." (Abstract)

Publication titled "Smoked cannabis for chronic neuropathic pain: a randomized controlled trial." (CMAJ. 2010 Oct. 5; 182(14):E694-701. doi: 10.1503/cmaj.091414. Epub 2010 Aug. 30.) discloses: "BACKGROUND: Chronic neuropathic pain affects 1%-2% of the adult population and is often refractory to standard pharmacologic treatment. Patients with chronic pain have reported using smoked cannabis to relieve pain, improve sleep and improve mood. METHODS: Adults with post-traumatic or postsurgical neuropathic pain were randomly assigned to receive cannabis at four potencies (0%, 2.5%, 6% and 9.4% tetrahydrocannabinol) over four 14-day periods in a crossover trial. Participants inhaled a single 25-mg dose through a pipe three times daily for the first five days in each cycle, followed by a nine-day washout period. Daily average pain intensity was measured using an 11-point numeric rating scale. We recorded effects on mood, sleep and quality of life, as well as adverse events. RESULTS: We recruited 23 participants (mean age 45.4 [standard deviation 12.3] years, 12 women [52%]), of whom 21 completed the trial. The average daily pain intensity, measured on the 11-point numeric rating scale, was lower on the prespecified primary contrast of 9.4% v. 0% tetrahydrocannabinol (5.4 v. 6.1, respectively; difference=0.7, 95% confidence interval [CI] 0.02-1.4). Preparations with intermediate potency yielded intermediate but nonsignificant degrees of relief. Participants receiving 9.4% tetrahydrocannabinol reported improved ability to fall asleep (easier, p=0.001; faster, p<0.001; more drowsy, p=0.003) and improved quality of sleep (less wakefulness, p=0.01) relative to 0% tetrahydrocannabinol. We found no differences in mood or quality of life. The most common drug-related adverse events during the period when participants received 9.4% tetrahydrocannabinol were headache, dry eyes, burning sensation in areas of neuropathic pain, dizziness, numbness and cough. CONCLUSION: A single inhalation of 25 mg of 9.4% tetrahydrocannabinol herbal *cannabis* three times daily for five days reduced the intensity of pain, improved sleep and was well tolerated. Further long-term safety and efficacy studies are indicated. (International Standard Randomised Controlled Trial Register no. ISRCTN68314063)." (Abstract)

SUMMARY OF THE INVENTION

According to an aspect of some embodiments of the invention, there is provided a system for delivering to a subject at least one pre-determined amount of THC, the system comprising: a memory which stores a scheduled regimen for delivery of THC to the subject, the scheduled regimen defining: (a) a maximal amount of THC to be delivered, the amount being 0.75 mg or less, and (b) a time period within which the amount is delivered, the time period being 2 hours or longer; a decision module which decides, according to the scheduled regimen, if a delivery should take place; and an inhaler device for delivering the THC to the subject, the inhaler device comprising a controller which carries out delivery of the THC based on the decision made by the decision module. In some embodiments, the system is configured to deliver a total of no more than 10 mg THC over a 24 hour time period. In some embodiments, one or both of the memory and the decision module are included within the inhaler device. In some embodiments, one or both of the memory and the decision module are included within the controller. In some embodiments, one or both of the memory and the decision module are associated with or included in a smartphone. In some embodiments, the inhaler comprises a heating mechanism for heating a quantity of THC-comprising material to deliver THC from the quantity of THC-comprising material to the user. In some embodiments, the controller carries out delivery by controlling one or more of: heating parameters, an amount of THC-comprising material being heated, and regulation of airflow. In some embodiments, the controller carries out delivery of less than the maximal amount by controlling heating of a quantity of THC-comprising material having a THC content of between twofold and fivefold the amount of THC being extracted. In some embodiments, the inhaler includes the quantity of THC-comprising material. In some embodiments, the controller carries out delivery of less than the maximal amount by controlling heating of a quantity of THC-comprising material having a THC content of between 2 times to 35 times the amount of THC being extracted. In some embodiments, the inhaler includes the quantity of THC-comprising material. In some embodiments, the inhaler is configured to heat the quantity of THC-comprising material only once. In some embodiments, the inhaler is configured to heat the quantity of THC-comprising material more than once. In some embodiments, the system comprises a cartridge containing the quantity of THC-comprising material, the cartridge received within the inhaler. In some embodiments, the cartridge further comprises one or more active substances other than THC. In some embodiments, the THC-comprising material comprises one or more additional active substances. In some embodiments, the decision module is configured to prevent delivery for a time period long enough for at least one effect induced by the THC on the subject to take place. In some embodiments, the decision module is configured to limit the maximal amount of THC to an amount small enough so as not to induce a significant psychoactive effect on the subject. In some embodiments, the decision module is configured to allow a time window set from initial delivery of an amount smaller than 0.5 mg THC, wherein during the time period additional delivery of up to a total of 0.5 mg THC including the initial delivery is enabled. In some embodiments, the decision module is configured to receive input regarding a THC-comprising material from which the THC is delivered, and, according to the input, to adjust the time period. In some embodiments, the decision module is configured to adjust the time period according to one or more of: an amount or concentration of THC in the THC-comprising material; a strain of the THC-comprising material and additional active substances included in the THC-comprising material. In some embodiments, the system comprises at least two quantities of THC-comprising material differing from each other in at least one property selected from a group consisting of: a concentration of THC in the quantity, a strain of the THC-comprising material, additional active substances included in the THC-comprising material, the mass of the quantity of THC-comprising material and the total amount of THC in the quantity of THC-comprising material, and wherein the decision module is configured to select which cartridge to use according to a time period defined for each of the cartridges according to the at least one property. In some embodiments, in predefined exceptions the decision module is configured to allow delivery exceeding at least one of the (a) and (b). In some embodiments, delivery under the predefined exceptions is limited according to one or more of: no more than two exceptional deliveries allowed within a 24 hour period; no more than two exceptional deliveries allowed within a 12 hour period; any exceptional delivery allowing no more than two folds the maximal amount of THC; and the total amount of THC delivered over a 24 hour period amounts to no more than 10 mg. In some embodiments, following an exceptional delivery the decision module returns to operate according to the scheduled regimen for a time period of at least 2 hours. In some embodiments, the decision module is configured to analyze previous amounts delivered within any defined time period to determine whether an additional amount can be provided at a current or future time point.

According to an aspect of some embodiments of the invention, there is provided a method of controlling a THC dispensing device, comprising: dispensing an initial dose of THC; within a first time window, allowing dispensing of a further dose of THC such that a total amount of the initial dose and the further dose is no more than 0.5 mg THC; and within a second time window, preventing dispensing of any additional dose of THC until the second time window has ended. In some embodiments, the initial dose and the further dose of THC are each dispensed over a single delivery event.

In some embodiments, each of the delivery events takes place during a single inhalation of a user of the THC dispensing device. In some embodiments, a total number of delivery events over a 24 hour time period is 12 or less. In some embodiments, a total of no more than 10 mg THC are dispensed over a 24 hour time period. In some embodiments, at least one of the initial dose of THC, the further dose of THC and the additional dose of THC is dispensed concomitantly or sequentially with one or more other active substances. In some embodiments, no more than 0.75 mg THC are delivered at any given dose. In some embodiments, a total of the initial dose and the further dose is selected to be sufficient to reduce a treated symptom without return of the symptom to a pre-inhalation degree for at least as long as the second time window. In some embodiments, the second time window is 2 hours or longer. In some embodiments, the first time window is selected to be long enough to allow a user to sense the effect of the dose of THC. In some embodiments, the first time window is between 15 minutes to 2 hours from dispensing of the initial dose. In some embodiments, the initial dose and the further dose together are lower than a maximal dose allowed within the first time window. In some embodiments, the method comprises dispensing an additional dose of THC after the second time window has ended. In some embodiments, dispensing comprises extracting the THC from THC-comprising material.

According to an aspect of some embodiments of the invention, there is provided a method of pulmonary delivery of a combination of at least two cannabinoids to a subject, comprising: delivering a first dose comprising at least two cannabinoids at a predetermined ratio; waiting at least two hours; delivering a second dose comprising a combination of the at least two cannabinoids at a second ratio different than the ratio of the first dose. In some embodiments, the first and second doses comprise THC. In some embodiments, the first and second doses comprise CBD. In some embodiments, the ratio comprises a THC to CBD ratio. In some embodiments, the first and second doses comprise CBN. In some embodiments, the ratio includes a THC to CBD ratio. In some embodiments, the ratio includes a cannabinoid that is undetectable in at least one of the first and second doses. In some embodiments, the second dose is extracted from a *cannabis* strain different from a *cannabis* strain from which the first dose was extracted.

According to an aspect of some embodiments of the invention, there is provided a method of pulmonary delivery of THC to a patient undergoing chemotherapy, comprising delivering a first dose of 1 mg THC or less at least 30 minutes before chemotherapy begins; delivering no more than 10 doses of no more than 1 mg THC each over a 24 hour period, the doses delivered at time intervals of at least two hours.

According to an aspect of some embodiments of the invention, there is provided a method for delivering at least one active substance to a subject through inhalation, comprising delivering a first dose of the active substance to the subject; waiting at least a time period sufficient for an effect of the at least one active substance to take place, and during the time period allowing delivery of a placebo; after the time period has ended, allowing delivery of a second dose of the active substance.

According to an aspect of some embodiments of the invention there is provided an inhaler for delivering to a subject at least one pre-determined vaporized amount of THC, the inhaler comprising a controller configured to limit the amount of THC to no more than 2 mg THC delivered in a 2 hour time period. In some embodiments, the inhaler is configured to deliver a total of no more than 7.5 mg THC over a 24 hour time period. In some embodiments, the inhaler comprises a heating mechanism for heating a THC-comprising material to deliver no more than 2 mg THC from the THC-comprising material. In some embodiments, the controller is configured to limit the amount of THC by controlling one or more of: heating parameters, an amount of THC-comprising material being heated, and regulation of airflow. In some embodiments, the controller is configured to adjust extraction efficiency. In some embodiments, the inhaler comprises a cartridge including a THC-comprising material having a THC content of between twofold and fivefold the amount of THC being extracted. In some embodiments, the THC-comprising material comprises no more than 3.5 mg THC. In some embodiments, the inhaler is configured to heat the cartridge more than once. In some embodiments, the cartridge comprises one or more additional active substances. In some embodiments, the inhaler comprises a total of 8 cartridges, sufficient for use over a 24 hour period. In some embodiments, the controller is configured to prevent delivery for a time period of at least 1.5 hours after 30 minutes lapsed from the last delivery event.

According to an aspect of some embodiments of the invention there is provided a method of pulmonary delivery of THC to a subject, comprising: delivering THC to the subject such that within any time period of two hours or more, a total of no more than 0.2-2 mg THC are delivered. In some embodiments, the amount of THC is delivered over a single delivery event including one or more inhalations of the subject. In some embodiments, the method further comprises, prior to the delivering, heating plant material to extract the THC. In some embodiments, the method further comprises, prior to the delivering, extracting the THC from a material carrying one or more of extracted, purified and/or synthetic THC. In some embodiments, the material comprises THC at an amount which is between twofold and fivefold the amount of THC being extracted. In some embodiments, a total number of delivery events over a 24 hour time period is 8 or less, wherein in each delivery event between 0.2-2 mg THC are delivered to the patient. In some embodiments, a total of no more than 7.5 mg THC are delivered over a 24 hour time period. In some embodiments, THC is delivered concomitantly or sequentially with one or more other active substances. In some embodiments, an actual amount of THC from the range of 0.2-2 mg THC is selected to be sufficient to reduce a treated symptom without return of the symptom to a pre-inhalation degree for a time period of two hours or more.

According to an aspect of some embodiments of the invention there is provided an inhaler for delivering to a subject at least one pre-determined vaporized amount of THC from a THC-comprising material by controllably heating the material so as to deliver the at least one pre-determined vaporized amount of THC; the device comprising at least one cartridge in which the THC-comprising material is contained, the cartridge sufficient for a single delivery event over which the pre-determined vaporized amount of THC is delivered to the subject through inhalation; and the cartridge comprising, when fully loaded, THC-comprising material having no more than about 3.5 mg of THC.

According to an aspect of some embodiments of the invention there is provided an inhaler for delivering to a subject at least one pre-determined vaporized amount of THC from a THC-comprising material by controllably heating the material so as to deliver the at least one pre-determined vaporized amount of THC; the device comprising at least one cartridge in which the THC comprising material is contained, the cartridge sufficient for a single delivery event over which the pre-determined vaporized amount of THC is delivered to the subject through inhalation; and the cartridge comprising, when fully loaded, no more than 20 mg of THC-comprising material. In some embodiments, the THC-comprising material is plant material. In some embodiments, the plant material is augmented with an extract and/or a synthetic drug.

According to an aspect of some embodiments of the invention there is provided an inhaler for delivering to a subject at least one pre-determined vaporized amount of THC, the inhaler comprising a controller configured to limit the amount of THC to no more than 2 mg THC delivered during any time period sufficient for one or more effects of the THC to become significant.

According to an aspect of some embodiments of the invention there is provided a magazine comprising a plurality of cartridges, each cartridge comprising a THC-comprising material at amount which comprises no more than 4 mg THC. In some embodiments, an amount of THC is equal for all of the plurality of cartridges. In some embodiments, the plurality of cartridges comprise different amounts of THC.

According to an aspect of some embodiments of the invention there is provided a method of pulmonary delivery of a combination of a low dose of THC and at least one other cannabinoid to a subject, comprising: delivering a first dose comprising a combination of THC and the at least one other cannabinoid at a predetermined ratio; waiting at least two hours; delivering a second dose comprising a combination of THC and the at least one other cannabinoid at a ratio which is at least 10% larger or at least 10% smaller than the ratio of the first dose. In some embodiments, the at least one other cannabinoid is CBD. In some embodiments, the second dose is extracted from a *cannabis* strain different from a *cannabis* strain from which the first dose was extracted.

According to an aspect of some embodiments of the invention there is provided a method of pulmonary delivery of THC to a patient undergoing chemotherapy, comprising delivering a first dose of 0.5 mg THC at least 30 minutes before chemotherapy begins; delivering no more than 7 doses of 0.5 mg THC each over a 24 hour period, the doses delivered at time intervals of at least two hours.

According to an aspect of some embodiments of the invention there is provided a method for delivering a plurality of low doses of at least one active substance through inhalation, comprising delivering, within a first time interval, a first low dose of the active substance, the first low dose lower than a maximal dose allowed within the first time interval; waiting at least a time period sufficient for an effect of the at least one active substance to take place; delivering, within the first time interval, a second dose of the active substance, the second low dose lower than a maximal dose allowed within the first time interval; delivering a third dose of the active substance after at least two hours have passed from the delivering of the first dose.

According to an aspect of some embodiments of the invention there is provided an inhaler configured for delivering a plurality of low doses of at least one active substance through inhalation, comprising a controller programmed to limit delivery of the active substance according to one or more of: a maximal dose allowed within a predetermined time interval, a time period that passed from the last delivery; an effect of the active substance as indicated by a user.

Unless otherwise defined, all technical and/or scientific terms used herein have the same meaning as commonly understood by one of ordinary skill in the art to which the disclosure pertains. Although methods and materials similar or equivalent to those described herein can be used in the practice or testing of embodiments of the disclosure, some methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3 is a flowchart of a method for obtaining a personal pharmacodynamic (PD) parameter from a patient and modifying a regimen accordingly, according to some embodiments of the present disclosure;

DETAILED DESCRIPTION OF THE INVENTION

Figure 1:
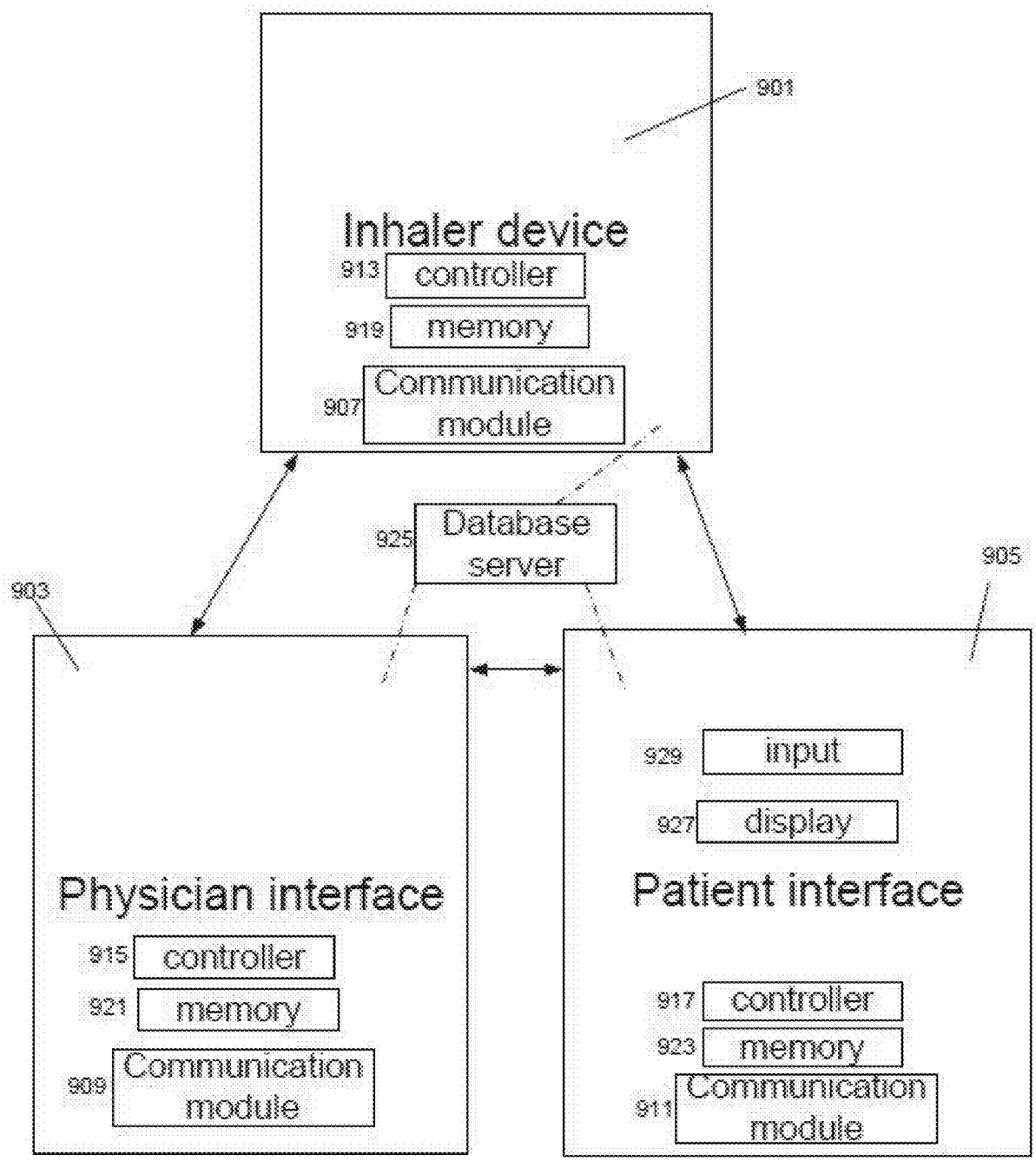
FIG. 1 is a schematic diagram of a system comprising an inhaler device, a physician interface and/or a patient interface, according to some embodiments of the present disclosure.

The present invention, in some embodiments thereof, relates to pharmacology and, more particularly, but not exclusively, to methods, devices and systems for controlled pulmonary delivery of active agents.

Before explaining at least one embodiment of the invention in detail, it is to be understood that the invention is not necessarily limited in its application to the details set forth in the following description or exemplified by the Examples.

As used herein, the terms "pharmacokinetic/pharmacodynamic" and "PK/PD" mean pharmacokinetic and/or pharmacodynamic. PCT publication WO2016/001923, which is incorporated herein by reference, includes for example the terms pharmacokinetic profile, level, effect and/or parameter and pharmacodynamic profile, level, effect and/or parameter which are contemplated in this application as well.

As used herein, the terms "therapeutic window" and "pharmaceutical window" are interchangeable and refer to the range of pharmacodynamic effects induced by a range of doses of one or more pharmaceutically active agents, providing a balance between one or more desired (positive) effect(s) and one or more adverse (negative) effect(s). According to some embodiments, the pharmaceutical/therapeutic window is referred to as a pharmacodynamic profile. The window may relate to a given point in time or may span a period of time of any length, including for example minutes, hours, days or longer, shorter or to any intermediate period of time. The desirability and undesirability of an effect can be defined based on a variety of criteria, and include without limitation, medical practices, rules and regulations, cultural and demographic norms, genetic factors and personal preferences and tolerances. For example, the desirability and undesirability of an effect can be defined based on the purpose of treatment and based on generally acceptable values and optionally may take into account other parameters such as patient preference, capacity and activity. It is noted that a given effect may be regarded as desired in some cases, but be regarded as undesired in other cases, and vice versa.

According to some embodiments of the present invention, the methods, devices and systems provided herein are capable of vaporizing a pre-determined vaporized amount of an active agent that induced one or more pre-determined pharmacodynamic effects in a given subject or a population of subjects, wherein the pre-determined pharmacodynamic effect pertains to a pre-determined pharmacodynamic profile that may range between a minimal level of a desired effect and any level of an undesired effect.

In some embodiments this a pharmaceutical window spans pharmacodynamic effects ranging from the lowest level of an effective treatment of a medical condition (therapeutic effect; e.g., pain relief) to a highest level of tolerable adverse effects (e.g., tolerable psychotropic effect as described herein). Optionally, the therapeutic window may be correlated to a selected balance between therapeutic and adverse effects. For example, the undesired effects are sufficiently tolerable or even minimized, while the desired effects reach at least a minimal acceptable level or a minimal mandatory level (e.g. life preserving or preserving the function of an organ or system of the user). Optionally, an adverse effect may be limited according to a probability of serious or irreparable damage to the subject's like or well-being. However, several alternative balances may be obtainable and one may choose between the optional therapeutic windows them based on user preferences.

Herein throughout, the term "patient" is used interchangeably with the terms "subject", "user" and "a person in need thereof" to refer to the entity that uses any of the devices and systems provided herein and being the subject of any of the methods provided herein.

A therapeutic window can be correlated, via a pharmacokinetic profile, to a range of amounts of one or more pharmaceutically active agents. For example, a therapeutic window may be defined as a range of amounts of one or more pharmaceutically active agent spanning from an amount that confers a desired effect (a therapeutic effect, in which case the amount is a therapeutically effective amount or therapeutic dose) and an amount that causes more than an acceptable or tolerable level of undesired effects (e.g., adverse effects). Hence, for example, a pharmaceutically active agent having a narrow therapeutic window should be administered with great care and control so as to stay between the therapeutically effective amount and the amount that causes an adverse effect.

According to an aspect of some embodiments of the present disclosure, there is provided a method of pulmonary delivering at least one pharmacologically active agent to a patient, which is carried out by pulmonary delivering the agent to the patient using a metered dose inhaler device, wherein the device is configured to release at least one pre-determined vaporized amount of the agent upon controllably heating a substance that contains the agent, wherein the amount is set so as to achieve at least one pre-determined effect in a subject, such as a pre-determined pharmacodynamic effect.

It is to be understood that the pharmaceutically active agent can be in a solid or a liquid form, and further noted that the agent is contained in a solid form of a substance described herein. According to some embodiments of the present disclosure, the pharmaceutically active agent is vaporizable by heat, thereby can be released from the substance by being heat-induced vaporization.

According to some embodiments, the substance that contains at least one vaporizable active agent is, for example, a plant material. In some embodiments, the active agent is a naturally occurring agent, namely the agent occurs (produced) naturally in the plant. Alternatively, the substance is an organic material which contains, or consists of, for example, one or more natural plant materials, or a synthetic material which may comprise at least one vaporizable active agent. In some embodiments, the solid form of a substance comprises a plurality of vaporizable active agents derived or extracted from natural or organic sources, such as plants, fungi, bacteria and the likes.

In some embodiments, the substance is a natural plant matter. In an embodiment of the present disclosure, the plant matter is processed without damaging the vaporizable active agent in the plant matter. Optionally, the plant matter retains a macroscopic plant structure.

The amount of the substance used in the MDI device may be determined based on the contents of the vaporizable agent contained therein, and on the pre-determined vaporized amount required to be released therefrom. The amount of the substance used in the MDI device may range from 20 to 500 mg, 10 to 200 mg, 9 to 150 mg, 8 to 100 mg, 7 to 50 mg, 5 to 20 mg, 1 to 10 mg, 10 to 70 mg, 10 to 60 mg, 12 to 50 mg, 12 to 40 mg, 15 to 40 mg, 12 to 30 mg or 12 to 25 mg.

The terms "pharmaceutically active agent", "biologically active agent", "active agent" and "agent" are used herein interchangeably and refer to a compound, a polymer, a conjugate or a complex, or any combination thereof, which exerts a physiological or psychological effect when administered to a subject. Typically, the pharmaceutically active agent or biologically active substance exerts a desired physiological or psychological effect upon pulmonary delivering thereof via a systemic pathway (e.g., blood, lymph) to a target organ. The agent may be of natural origin or synthetic. Non-limiting examples of active agents include CNS active agents, chemotherapeutic agents, sedative or analgesic agents and a psychotropic agent. In the context of embodiments of the present disclosure, the pharmaceutically active agent is a naturally occurring agent found in a naturally occurring substance (e.g., a natural plant substance, as described herein), or a metabolite thereof. These terms also encompass, unless otherwise indicated, two or more agents.

According to some embodiments of the present disclosure, the method is carried out using an MDI which is capable of delivering reproducibly and accurately an amount of at least one vaporizable agent by heating a solid form of a substance. Such requirements of an MDI are met by, for a non-limiting example, an MDI as disclosed in U.S. patent application Ser. No. 13/997,302 or WO 2012/085919, both of which is incorporated herein by reference in its entirety as if fully set forth herein.

According to some embodiments of the present disclosure, the MDI device is a device as described in WO 2012/085919, including any one of the embodiments described therein, and any combination thereof.

The term "vaporized amount", as used herein, refers to the amount of an agent that is in vapor form, whereas the vapor form/amount is obtained by means of a heating elements in the MDI device. It is noted herein that in some embodiments the amount of vaporized agent in the context of the present disclosure is not an estimated amount but rather represents the actual amount vaporized upon said heating.

The term "pre-determined vaporized amount" refers to an amount that is purposely or knowingly released from the MDI device, the magnitude of which is determined by choice or by design of a dose and/or regimen protocol, as described herein. In the context of some embodiments, the term "dose" represents a pre-determined vaporized amount. It is noted that a pre-determined vaporized amount is cor-related to an available amount present in the device, and that one can pre-measure the available amount present in the device, or measure the available amount present in the device in conjunction to the administration event, and thereby preset, reset, adjust and/or readjust the pre-determined vaporized amount accordingly.

Initial Dose Determination and Device Calibration:

According to some embodiments, the method is performed such that the pre-determined vaporized amount is selected/controlled so as to exhibit a pre-selected (also referred to herein as pre-determined) pharmacokinetic profile and/or a pre-selected or pre-determined pharmacodynamic profile of the agent in the patient.

In some embodiments, the pre-determined vaporized amount is selected/determined arbitrarily, while the MDI device is configured to vaporize and deliver this amount consistently and accurately throughout any number of uses and inhalations, using any source of the active agent (substance; plant material, combination of plant material with another material etc.). According to some embodiments, a pre-determined vaporized amount of an agent can be determined based on a measurement of the amount of the agent per unit mass of the substance from which the agent is to be vaporized. Such measurement can be carried out by standard procedures; thereby various batches and sources of the substance can be standardized according to the relative amount of the agent per unit mass of the substance.

It is noted herein that according to some embodiments of the present disclosure, by exhibiting a pre-selected pharmacokinetic and/or pharmacodynamic profile, it is meant that the vaporized amount of the agent has been pre-determined based on pharmacokinetic/pharmacodynamic (PK/PD) studies conducted in at least one subject by pulmonary delivering the agent using an MDI device which is configured to release a consistent and accurate vaporized amount of the agent upon heating a solid substance comprising the same. It is also noted herein that according to some embodiments of the present disclosure, by exhibiting a pre-selected pharmacokinetic profile, it is meant that at least one desired pharmacokinetic profile has been identified and that at least one pre-determined vaporized amount of the agent has been shown to effect that desired pharmacokinetic profile in a subject. It is also noted herein that according to some embodiments of the present disclosure, by exhibiting a pre-selected pharmacodynamic profile, it is meant that at least one desired pharmacodynamic profile has been identified and that at least one pre-determined vaporized amount of the agent has been shown to effect that desired pharmacodynamic profile in a subject.

In some embodiments of the present disclosure, the terms "pre-selected" and "pre-determined" refers to, or used interchangeably with, the terms "intended", "desired" or "desirable", or with the terms "effective", "needed" and "therapeutic".

In some embodiments, the term "pre-determined vaporized amount" is also used herein to describe the amount of the agent that is determined based on pharmacokinetic/pharmacodynamic (PK/PD) data, namely a vaporized amount that has been determined by determining PK/PD effects (parameters) for the agent in one or more patients.

In some embodiments, configuring the MDI device to release a pre-determined amount as defined herein means, in some embodiments, calibrating the device to exhibit a pre-selected PK and/or a pre-selected PD profile.

According to some of any of the embodiments of the present disclosure, the method is carried out by adjusting the pre-determined vaporized amount so as to achieve a pre-determined pharmacokinetic effect and/or a pre-determined pharmacodynamic effect based on data indicative of at least one pharmacokinetic effect and/or at least one pharmacodynamic effect induced by the agent in the subject.

In some embodiments, the method further includes generating the indicative data by monitoring at least one pharmacokinetic effect and/or at least one pharmacodynamic effect induced by the agent in the subject.

According to some of any of the embodiments of the present disclosure, the method is carried out by monitoring and/or determining at least one pharmacokinetic effect and/or or at least one pharmacokinetic variable and/or at least one pharmacodynamic effect, as these terms are defined herein, which are induced by pulmonary delivering the pharmaceutically active agent to a patient using the MDI device;

based on the pharmacokinetic effect and/or the pharmacokinetic variable and/or the pharmacodynamic effect, determining the pre-determined vaporized amount which exhibits the pre-selected pharmacokinetic profile and/or the pre-selected pharmacodynamic profile of the agent in the patient; and adjusting the MDI device to deliver the pre-determined vaporized amount of the agent.

As used herein, the phrase "pharmacokinetic profile" refers to a bodily concentration of a pharmaceutically active agent, or a metabolite thereof (e.g., an active metabolite), namely, a concentration of the agent or a metabolite thereof in a physiological system of an organism (whole body, blood, plasma, lymph, tissue, organ and the likes) to which the compound has been administered, as a function of time. Typically, a pharmacokinetic (PK) profile is considered from a time point of administration of the compound to a time point at which the compound is no longer detectable in the organism or to any intermediate period of time between administration of the compound and a time at which it is no longer detectable in the organism (e.g. due to excretion); hence, a PK profile describes the bodily concentration in a specific physiological system of a specific compound between administration and dissipation, as affected by the mechanisms of liberation, absorption, distribution, metabolism and excretion/secretion of the compound. Since each organism, and each individual organism within a genus of an organism, reacts differently to the administration of the agent, a PK profile may be different, and in some cases highly variable from subject to subject, and may be different within an individual subject based on a current physiological state, medical condition, environmental conditions and even the time of day.

According to some embodiments of the present disclosure, a pharmacokinetic profile is achieved by providing a subject with one or more of:

A dose—a single amount of a compound or an agent that is being administered thereto; and/or A regimen—a plurality of pre-determined doses that can be different in amounts or similar, given at various time intervals, which can be different or similar in terms of duration. In some embodiments, a regimen also encompasses a time of a delivery period (e.g., agent administration period, or treatment period).

Alternatively, a regimen is a plurality of predetermined plurality pre-determined vaporized amounts given at pre-determined time intervals.

It is noted that the PK profile can be determined according to a change of a PK effect (parameter) as a function of time, or of a combination of PK effects a function of time.

A PK profile is typically assessed on a concentration on a time scale, using directly and/or indirectly measured PK effects. For example, a PK profile may be a plasma concentration of a given pharmaceutically active agent in a subject as a function of time.

The term "pre-selected pharmacokinetic profile", as used herein, refers to a PK profile, which has been selected as desirable. A pre-selected PK profile may be selected since it has been found effective in accomplishing a desired pharmacodynamic effect in a subject, as described in any one of the respective embodiments (e.g., to maintain a subject within a therapeutic window, as described herein).

The terms "pharmacokinetic parameter", "pharmacokinetic effect", as used herein interchangeably, refer to a measurable and quantifiable physiological effect in a subject, which pertains to the presence of a pharmaceutically active agent in a subject. PK effects are direct or indirect expressions of a group of physiological processes that include absorption, distribution, metabolism, and excretion (ADME) of a pharmaceutically active agent in a subject.

PK effects typically include, without limitation:

$C_t$, which is the concentration of an agent, as determined, measured or assessed in a specific physiologic system (e.g., in the plasma), after its administration (delivery, e.g., pulmonary delivery) of a dose or a regimen to a subject;

$C_{max}$, which is the peak concentration of an agent, as determined, measured or assessed in a specific physiologic system (typically in the plasma), after its administration to the subject;

$T_{max}$, which is the time passed between administration and arriving at $C_{max}$;

Area under the curve ($AUC_{0\to\infty}$; zero to infinity), which is the integral of the concentration curve as a function of time, typically after a single dose or in steady state;

$C_{min}$, which is the lowest concentration of the agent in the organism before the next dose is administered;

$T_{min}$, which is the time passed until $C_{min}$ is detected, or until the next dose is administered;

$C_{last}$, which is the last observed quantifiable concentration;

$\lambda_z$, which is the terminal phase rate constant;

Elimination half-life ($t_{1/2}$), which is the time required for the concentration of the agent to reach half of any selected value;

Elimination rate constant ($k_E$), which is the rate at which an agent is removed from the organism;

Administration rate ($k_{in}$), which is the rate of administration required to balance elimination;

Clearance, which is the volume of plasma cleared of the agent per unit time;

Bioavailability, which is the systemically available fraction of an agent; and

Fluctuation, which is the peak trough fluctuation within one dose, or one regimen interval, at steady state.

As a tool for assessing the PK profile in a member of a population (a subject) of similar individual subjects (similar in the biological sense, as in a group of humans), PK variables, which have been found to be correlated to a PK profile in a sub-set of the population, may be used to generalize (extrapolate) the PK profile for each of the individuals comprising the entire population.

The term "pharmacokinetic variable", as used herein, refers to a property of a subject that is not necessarily dependent on a pharmaceutically active agent or a method of delivery a pharmaceutically active agent to a subject, and provide information pertaining to factors that affect the pharmacokinetic and pharmacodynamic profiles of an active agent in the subject.

Pharmacokinetic variables typically include, without limitation, body weight, body height, body mass index (BMI), waist-to-hip ratio, lean body mass (LBM), age and gender, race, background illnesses, patient history (e.g. previous exposure to the agent or other agents) and concurrent medication. It is to be understood that PK variables depend on genetic and epigenetic composition of each individual subject, and therefore can be used to predict PK/PD profiles in an individual subject to a certain degree of accuracy. However, personalization/individualization of a treatment based on administration of a pharmaceutically active agent is typically based on personal PK/PD effects/parameters data acquisition that is used to determine the dose and regimen for an individual subject. In general, deviation of individual parameters from average parameters set for a wide population are notably small.

In the context of some embodiments of the present disclosure, the term "treatment" refers to any one of: a single pulmonary administration of an agent at a given dose; a fixed and limited series of pulmonary administrations of an agent, given at the same or different doses at the same or different dose intervals (regimen); a chronic treatment which is administered as the limited series, but without a planned termination of the treatment (continuous treatment); and/or any combination thereof. Typically, a series of pre-determined doses given at pre-determined intervals, is referred to herein as a treatment regimen, or a regimen.

According to some embodiments of the method presented herein, pulmonary delivering the agent comprises a single dose delivered as one pre-determined vaporized amount released by the MDI device in a single inhalation session or the dose can be administered to a patient as several concomitant inhalations. Alternatively, a series of doses, each administered in one or more pre-determined vaporized amount, and given at a pre-determined time intervals, is referred to herein as a regimen. A regimen is therefore defined by one or more doses, administered in one or more pre-determined vaporized amounts, at pre-determined time intervals, wherein each of the pre-determined vaporized amounts, the doses and the time intervals can be the same or different.

In the context of embodiments of the present disclosure, a PK profile of a given pharmaceutically active agent is a result of the dose and/or regimen by which an agent is administered to a patient, or, alternatively, according to some embodiments, the PK profile is a mean to afford a particular, a pre-selected or otherwise desired pharmacodynamic profile of the agent in the patient.

As used herein, the term "pharmacodynamic profile" refers to the effect of a pharmaceutically active agent in a subject as a function of time. Accordingly, the term "pharmacodynamic profile" refers to a sum of all biological expressions and responses of an organism as a function of time, upon administration of a pharmaceutically active agent. A pharmacodynamic profile is typically a direct or indirect result of pharmacokinetic effect(s) at any given time point, or a pharmacokinetic profile of the agent in the patient, over any given time period.

A pharmacodynamic profile represents a change/variation of directly and/or indirectly determined pharmacodynamic effect(s) as a function of time.

The terms "pharmacodynamic parameter", "pharmacodynamic effect", as used herein interchangeably, refer to a group of effects pertaining to a subject and a pharmaceutical active agent, which are manifested in the subject upon administering the agent to the subject. Typically, pharmacodynamic parameters depend on the subject's PK variables and on the subject's PK effects.

Pharmacodynamic parameters can typically be determined by, without limitation, a therapeutic (desirable) effect (e.g., personally perceived therapeutic effect), an adverse (undesirable) effect (e.g., a personally perceived adverse effect), and by means of determining a level of a biomarker (which is indicative of a therapeutic and/or an adverse effect), as these terms are described hereinbelow. A pharmacodynamic profile which can be a pre-selected (desired) pharmacodynamic profile, according to some embodiments of the present disclosure, is defined by the therapeutic window of a given agent in a given subject, as this term is defined herein.

A pharmacodynamic (PD) profile is typically a time-dependent assessment and/or measurement on a scale going from no response, through the onset of a desired therapeutic effect (below a therapeutic effect threshold), via the therapeutic window, through the onset of an adverse effect (above an adverse effect threshold), and up to a toxic effect.

According to some embodiments of the present disclosure, the pulmonary delivering and/or the PK/PD study (measurement of any pharmacokinetic and/or pharmacodynamic parameters) may optionally be conducted while monitoring at least one additional physiological parameter selected from the group consisting of:

a vital sign selected from the group consisting of a heart rate, an oxygenation level (SpO2), a blood pressure, a respiratory rate and a body temperature;

a pulmonary function selected from the group consisting of forced expiratory volume (FEV1), maximum mid-expiratory flow (MMEF), diffusing capacity of the lung for carbon monoxide (DLCO), forced vital capacity (FVC), total lung capacity (TLC) and residual volume (RV);

a hematological marker selected from the group consisting of a hemoglobin level, a hematocrit ratio, a red blood cell count, a white blood cell count, a white blood cell differential and a platelet count;

a coagulation parameter selected from the group consisting of a prothrombin time (PT), a prothrombin ratio (PR) and an international normalized ratio (INR);

a kidney function marker selected from the group consisting of a creatinine clearance (CCr), a blood urea nitrogen level (BUN) and a glomerular filtration rate (GFR); and a liver function marker selected from the group consisting of an aspartate aminotransferase (AST) level, a serum glutamic oxaloacetic transaminase (SGOT) level, an alkaline phosphatase level, and a gamma-glutamyl transferase (GGT) level.

Accordingly, there is provided a method of recording at least one pharmacokinetic effect and/or at least one pharmacodynamic effect, induced by pulmonary delivering to a subject at least one pharmacologically active agent being in a plant material; the method is effected by:

pulmonary delivering a pre-determined vaporized amount of the agent to the subject from a metered dose inhaler device configured to vaporize the pre-determined vaporized amount of the agent upon controllably heating the plant material;

optionally, determining at least one pharmacokinetic effect in the subject at pre-determined time intervals before during and/or after the pulmonary delivering;

determining at least one pharmacodynamic effect in the subject at pre-determined time intervals before during and/or after the pulmonary delivering;

wherein the pharmacodynamic effect is selected from the group consisting of a desired effect, an undesired effect, a therapeutic effect, an adverse effect and a level of a biomarker.

Personalization:

As discussed hereinabove, some PK/PD studies or some parts thereof are based on population parameters and on cohorts, yielding average or standardized dose and/or regimen data, while in reality a PK/PD profile may vary from patient to patient, and even within an individual patient, depending on a current physiological condition, mental state, medical condition and environmental conditions. Therefore, a pre-determined vaporized amount of an agent (preset dose and/or regime) may be found inadequate for a particular individual at any given time and for any individual reason. Hence, in order to provide an optimized treatment for a given individual, in any of the methods presented herein, each of the pharmacokinetic and/or pharmacodynamic parameter and/or variables may further be determined for an individual patient, such that the pre-determined vaporized amount is derived individually for the patient.

It is noted that according to some embodiments of the present disclosure, while a patient may start the pulmonary delivering using an initial pre-determined vaporized amount which has not been determined based on the patient's personal/individual parameters and variables, the method includes an optional step at which the patient's personal parameters and variables are considered in the determination of the pre-determined vaporized amount. Thus, according to some of any of the embodiments of the present disclosure, the method may include personalization of the pre-determined vaporized amount that affords the pre-selected PK/PD profile. The personalization step presented below can replace a pre-calibration of the MDI device; or as a complementary step after calibration of the MDI device.

Accordingly, the pharmacokinetic effect(s) and/or the pharmacokinetic variable(s) and/or the pharmacodynamic effect(s) are independently determined for an individual patient, such that the pre-determined vaporized amount is determined personally for that patient. It is noted herein that a personal pharmacokinetic parameter can be obtained directly by conducting a PK study in the patient by monitoring the concentration of the agent in the patient (e.g., using blood samples and/or other means), or by applying a calculation based on personal PK variables and other personal variables that may have an effect on the PK/PD profiles in that patient.

Alternatively, according to some of any of the embodiments of the present disclosure, the method may include collecting, observing or otherwise monitoring and determining at least one personal pharmacodynamic effect and/or pharmacokinetic effect in an individual subject so as to determine if pulmonary delivering the initial pre-determined vaporized amount of the agent exhibits the pre-selected (desirable) pharmacodynamic and/or pharmacokinetic profile;

if pulmonary delivering the pre-determined vaporized amount of the agent does not exhibit the pre-selected/determined pharmacodynamic and/or pharmacokinetic profile, determining an adjusted vaporized amount of the agent that exhibits the pre-selected pharmacodynamic and/or pharmacokinetic profile; and adjusting, resetting, re-calibrating or otherwise re-configuring the device to deliver an adjusted vaporized amount, whereby, upon re-configuring the MDI device, the adjusted vaporized amount being now the pre-determined vaporized amount.

According to some embodiments of the present disclosure, the personalization of the pulmonary delivering and/or the PK/PD study may optionally be conducted while monitoring at least one additional physiological parameter, as described herein. Optionally, monitoring at least one pharmacokinetic effect and/or at least one pharmacodynamic effect induced by the agent in the subject is carried out at pre-determined time intervals before, during and/or after the pulmonary delivering.

According to some embodiments, monitoring of a pharmacokinetic effect and/or a pharmacodynamic effect is carried out by receiving data indicative of these effects in the subject from at least one sensor being in communication with a controller, as these terms are discussed hereinbelow, associated with the inhaler device presented herein.

It is noted that a personal pharmacodynamic parameter can be a personally perceived therapeutic effect, a personally perceived adverse effect and a (level or presence of a) biomarker obtained and/or measured in the individual patient. According to some embodiments, the acquisition/determination of the personally perceived therapeutic effect, the personally perceived adverse effect and/or the biomarker may be conducted voluntarily by the patient, or involuntarily by automatic means. The method, according to some embodiments thereof, is then effected by determining an adjusted vaporized amount of the agent based on the personal pharmacodynamic parameter, and configuring the device to deliver the adjusted vaporized amount; whereby the adjusted vaporized amount is the pre-determined vaporized amount. In other words, the adjusted vaporized amount is the personalized pre-determined vaporized amount, which is based on personal pharmacodynamic parameters obtained for an individual patient, after being administered a pre-determined vaporized amount determined for a general population and using population PK variables. Alternatively, an expected response can be used as a parameter for confirming the identity of a user. For example, a user is instructed to perform a task at a given time before and/or after administration, and the measured value is compared with a comparable expected value recorded for the same user, optionally under similar circumstances.

Personally Perceived Effect:

A "personally perceived effect" is a subjective assessment of a patient pertaining to an effect of a given' agent or treatment in the patient's body. The personally perceived effect may include one or more of a personally perceived therapeutic effect or a personally perceived adverse effect.

A psychotropic effect optionally corresponds to a symptom that can be perceived by the patient. It is noted that in some cases a psychotropic effect may not be accurately perceived by the patient. Examples of psychotropic symptoms include, without limitation, paranoia, anxiety, panic attack, euphoria, pseudo-hallucinatory, sedation, conscious perception variation, joviality, metacognition and introspection, an enhanced recollection (episodic memory), amnesia, a sensuality variation, a variation in awareness of sensation and a variation in libido, dizziness, ataxia, euphoria, perceptual alterations, temporal distortion, intensification of ordinary sensory experiences, short term memory, and attention, impaired reaction, skilled activity, verbal fluency, dependence, melancholy and depression.

A somatic effect sometimes corresponds to a symptom which can be perceived by the patient or measured thereby. Examples for somatic symptoms include, without limitation, pain, migraine, nausea, dry mouth and a sensation of cold or hot hands and feet, increased heart rate, increased cerebral blood flow (e.g., migraine symptoms, "head pressure"), dilation of bronchial passages (e.g., coughing and difficulty breathing), dilation of blood vessels (e.g., shivers, skin redness, blushing), eye redness and pupil dilation, dry mouth, thirst, hunger or food craving.

Desired Effects—Therapeutic Effects:

A "personally perceived therapeutic effect" is a subjective assessment of a patient pertaining to a beneficial (desired) effect of a given agent in the patient's body. In some embodiments, a desired effect includes a relief of a symptom and/or an alleviation of cause of a medical condition. For example, if the desired therapeutic effect is defined as an alleviation of pain, the patient may report a level of pain by means of a pain scale evaluation protocol. A pain scale protocol measures a patient's pain intensity and/or other features. In the context of embodiments of the present disclosure, a pain scale protocol is based on self-report (subjective), observational and/or behavioral data provided by the patient, while physiological data falls under the definition of biomarkers, namely objective data. In general, all personally perceived (subjective) assessments by a patient can be used as feedback for self-titration and personalization of a treatment.

A personally perceived therapeutic effect may be associated with or corresponds to, directly or indirectly, a symptom of the medical condition which the patient is being treated for. In some cases a patient may perceive a change in the perceived level of the symptom, and when the symptom of the medical condition is alleviated (a diminution in the level of the symptom), the person perceives this change as a therapeutic effect of agent delivered during the treatment. Hence, according to embodiments, a personally perceived therapeutic effect corresponds to a reduction in a level of a symptom such as, but not limited to, pain, migraine, depression, cognitive function deficit, attention deficit, hyperactivity, anxiety disorders, diarrhea, nausea, vomiting, insomnia, delirium, appetite variations, sexual dysfunction, spasticity, increased intra ocular pressure, bladder dysfunction, tics, Tourette symptoms, posttraumatic stress disorder (PTSD) symptoms, inflammatory bowel disease (IBD) symptoms, irritable bowel syndrome (IBS) symptoms, hyper tension, hemorrhagic symptoms, septic and cardiogenic shock, drug addiction and craving, withdrawal symptoms, tremors and other movement disorders symptoms.

In some embodiments, a personally perceived therapeutic effect may include an effect that is not associated with or corresponds to, directly or indirectly, a symptom of the medical condition which the patient is being treated for, but is nonetheless beneficial to the patient's experiencing such symptom. For example, when a symptom includes a form of discomfort (for example pain or nausea), a patient may benefit from a psychoactive state in which the discomfort may be less prominent or more tolerable. One example of such a desired effect is causing temporary moderate stupor during pain. In some embodiments, the same effect may be therapeutic or adverse, depending on a degree thereof and/or timing thereof and/or other circumstances.

Undesired Effects—Adverse Effects:

A "personally perceived adverse effect" is associated with an emergence and/or an increase in the level of an undesired symptom that is not necessarily associated with the medical condition being treated, since it is caused, directly or indirectly, by a pharmacokinetic parameter of the pharmaceutically active agent being delivered to the patient.

According to some embodiments, a personally perceived undesired effect can be a mental effect, a psychotropic effect and/or a somatic effect, wherein the mental and/or psychotropic effect is mostly related to CNS activity which encompasses perception, consciousness, cognition and behavioral effects, and the somatic effect relates to all other bodily systems, and include, without limitation, gastro-intestinal, neuromuscular, cardiovascular, convulsive, endocrine effects and the like.

A personally perceived adverse effect is a subjective assessment of the patient pertaining to the adverse effect of a given agent in the patient's body. In general, all personally perceived (subjective) adverse effect assessments by the patient can be used as feedback for personalization of the treatment and self-titration.

Biomarkers:

While perception of an effect is a subjective assessment of the effect, and typically complicated to quantify, a biomarker is a more objective and typically measurable quantitative assessment of an effect. Thus, the term "biomarker", as used herein, is a measurable indicator of the PD profile at a given time point, and typically consists of a direct and/or indirect somatic, biologic and/or chemical manifestation of the therapeutic effect and/or an adverse effect. In other words, a biomarker is any objectively measurable quantity that can be used as an indicator of the state of a medical condition, the effect of a particular agent on the state of a medical condition, or another physiological state of an organism. It is note that some of the therapeutic/adverse effects can only be assessed qualitatively, and some can be assessed indirectly by, for example, measuring an impaired reaction by applying a performance test.

In the context of embodiments of the present disclosure, biomarkers are divided into the group of invasively-detected biomarkers and the group of non-invasively-detected biomarkers. In general, all biomarker data (objective) collected in the patient by any mean, observation measurement, sensor measurement and the likes, can be used as feedback for personalization of the treatment and self-titration. It is noted that some invasively-detected biomarkers can be detected and measured non-invasively and vice versa.

Examples for non-invasively-detected biomarkers include, without limitation, heart rate, oxygenation level (SpO2), blood pressure, respiratory rate, body temperature, inhalation volume, facial expressions, involuntary skeleto-muscular responses (ataxia, tremors, muscle twitches, cramps, spasms etc.), voluntary motor skills, sweating, hand-eye coordination, eye vascular expansion, reddening of the conjunctiva and/or sclera, variations in intra-ocular pressure, sinus tachycardia, cardiac arrhythmias, skin conductance/impedance levels, seizures, electromyography (EMG), electrocardiogram (ECG), photo-plethysmogram (PPG), galvanic skin response (GSR), Blue-Brown visual inhibition, H-mask visual inhibition, Auditory Latent inhibition, Visual Latent inhibition, Stroop colour word, Simple reaction (conflict task), Cognitive Set switching, Logical reasoning, Decision making time, Rapid info processing, Perceptual maze, Simulated driving, Visual search, Time estimation, Time perception, Visual search, Attentional search, Symbol copying, Letter cancellation, Alphabetic cross-out, D2 cancellation, Brickenkamp D2, digit copying test (DDCT), symbol-digit substitution (SDST), digit-symbol substitution test (DSST), Digit Vigilance, Vigilance, Auditory vigilance test, Wesnes/Warburton Vigilance task, Rapid info processing, CRT+Tracking Divided attention, Selective attention, Focused attention Task, Emotional attention Task, Auditory Flutter fusion, Flash fusion, critical flicker fusion (CFF), Continuous attention, Paired associate learning, Wordlist learning, 15 word test, Introductory conditioning, Delayed word recall, Delayed word recognition, Delayed picture recognition, Word presentation, Word recognition, Numeric working memory, Numerical memory, Memory scanning, Auditory Brown/Peterson, Visual Brown/Peterson, Visual spatial memory, Fragmented picture test, Pauli test, Block Span, Digit span, Digit Span (forward), Digit Span (backward), WAIS vocabulair, WAIS similarity, Word fluency, Verbal fluency, Performance time (Delayed word recogn.), Performance time (Numeric working memory), Performance time (Digit vigilance), Performance time (Rapid info processing), Performance time (Delayed picture recognition), Performance time (Visual information processing), Simple Reaction Time CRT, Complex RTvisual, Visual choice RT, VRT, Visual response speed, ART, Acoustic RT, Wire Maze Tracing, Archimedian spiral, Critical tracking task, Trail making, Tracking Complex, Tracking Wiener Geraet, Flexibility of closure, WAIS block design, WAIS picture comparison, Digit copying, Manipulative motor, Feinmotorik, Graphological analysis, tapping, Hand arm lateral reach coordination, Visual arm random reach, Motor control & coordination, Motor behavior and EEG.

Comprehensive descriptions of non-invasively-detected biomarkers, in the context of pharmaceutically active agents derived from *cannabis*, include, without limitation, a study by Zuurman, L. et al. [*British Journal of Clinical Pharmacology*, 2009, 67(1), pp. 5-21], which is incorporated herein by reference as if full set forth herewith.

In the context of some embodiments of the present disclosure, assessment, observation or recordation of a personally perceived desired/therapeutic effect and/or a personally perceived undesired/adverse effect can be used at any time, including when a non-invasive biomarker is not available to the patient or the practitioner in order to conduct monitoring of PD effects for a defining a pre-determined vaporized amount during initial calibration, and/or for adjusting the amount during self-titration or personalization of the device used in treatment. Alternatively, a user or a practitioner may choose not to use a non-invasive biomarker for any reason. Optionally, an invasive biomarker measuring device may be used for monitoring amount at least one pharmacokinetic effect and/or at least one pharmacodynamic effect induced by the agent in the patient, especially if already installed in or on the patient, which can be accessed and provide the required information. In some embodiments at least two of a perceived effect, a non-invasive biomarker and an invasive biomarker are used to measure and/or estimate the same or different PD effects induced in a user by the one or more pharmaceutically active agents. It is noted that sensors for monitoring PD effects may be used as part of a manual and/or automatic feedback process for determining and/or adjusting a pre-determined vaporized amount of an agent off-line or in real-time.

As used herein, the term "real-time" refers to a reference (recordation, detection, measurement, reporting, depiction, reaction etc.) to an event or a series of events, wherein the reference occurs essentially at the same time and/or at the same rate, as the event(s). By "essentially at the same time and/or at the same rate" it is meant that a single event and its corresponding reference are temporally separated by a response time that ranges between zero to 30 minutes (0-30 minutes), 0-20 minutes, 0-10 minutes, 0-5 minutes, 0-1 minute, 0-45 seconds, 0-30 seconds, 0-20 seconds, 0-10 seconds, 0-5 seconds, 0-1 second, 0-750 milliseconds, 0-500 milliseconds, 0-250 milliseconds, 0-100 milliseconds, 0-50 milliseconds, 0-10 milliseconds or 0-1 millisecond.

Optionally, "real-time" refers to a reference (recordation, detection, measurement, reporting, depiction, reaction etc.) to an event or a series of events, wherein the reference occurs essentially between administration of an active agent to the dissipation of at least one pharmacodynamic effect induced in the subject by the administered agent. In some embodiments, "real-time" refers to a reference to an event or a series of events, occurring between two drug delivery inhalation events scheduled to occur between administration of an active agent to the dissipation of at least one pharmacodynamic effect induced in the subject by the administered agent. Optionally, the "real-time" event or series of events includes adjusting the timing and/or amount of the later drug delivery inhalation event according to data indicative of one or more effect(s) of the earlier drug delivery inhalation event. In some embodiments, such dissipation means that the effect reaches a degree that is below detection for a given sensor and/or for being perceived by the user, as the case may be.

In the context of embodiments of the present invention, the term "real-time measurement" refers to a reference made by a sensor in response to an event that takes place in a subject in communication with the sensor. In some embodiments, a real-time measurement is a continuous, sporadic, regular or systematic monitoring, reporting, recordation, analysis, processing, presenting, displaying and transmitting of a pharmacodynamic effect by a designated sensor that is in communication with a subject.

While some PD effects are essentially subjective, such as the self-reported level of a symptom, the determination of some PD effects have been standardized so as to confer objectivity or at least afford a comparative scale that can be generalized across a population of subjects, as in the case of pain scales, wherein a change in the pain level is considered as a PD effect.

Invasively-detected biomarkers include any indicator that requires a sensor to be placed inside the body of the patient, including skin penetration, or requires a sample taken from within the body of the patient in order to quantify the indicator. For example, blood extraction from a vein of the patient using a needle, or via skin pricking, in order to measure the concentration of any indicator or factor (biomarker), is regarded as an invasive measurement, and thus these biomarkers are regarded as invasively-detected biomarkers.

Self-Titration:

In cases where a patient experiences for any reason inadequacy of a preset dose and/or regimen, regardless if the pre-determined vaporized amount of the agent (the preset dose and/or regimen) have been derived individually for that patient or not, this patient may wish to readjust the pre-determined vaporized amount of the agent (dose and/or regimen) according to a current physiological condition, a mental condition, or for any other reason. This option is regarded as self-titration of the agent, and be part of a manual feedback process for determining a pre-determined vaporized amount of an agent.

Hence, when the PD profile requires re-selection, the pulmonary delivery of the active agent from the MDI device further includes steps that allow the patient to self-titrate the pre-determined vaporized amount, or a practitioner to alter and readjust the pre-determined vaporized amount of the agent as needed.

According to some of any embodiments of the present disclosure, the pulmonary delivering of the pharmaceutically active agent further includes configuring the device to deliver an adjusted vaporized amount of the agent, whereas the adjusted vaporized amount is selected so as to exhibit a re-selected pharmacodynamic profile of the agent in the patient, whereby, upon the configuring, the adjusted vaporized amount becomes the pre-determined vaporized amount and the re-selected pharmacodynamic profile is regarded as a pre-selected pharmacodynamic profile.

In some embodiments, the readjustment is effected without re-determining a PK and/or a PD effect in the patient.

Automatic Feedback:

According to some embodiments, the adjustment or re-adjustment of the pre-determined vaporized amount of an agent (dose and regimen thereof) includes an automatic feedback process based on personal pharmacodynamic parameter data.

Personal pharmacodynamic parameter data optionally include at least one personally perceived therapeutic effect and at least one personally perceived adverse effect; and may further include at least one biomarker level datum.

As discussed hereinabove, the automatically obtained level of a biomarker may be an invasively-detected biomarker and a non-invasively-detected biomarker. According to embodiments of the present disclosure, the automatically obtained level of a biomarker is that of a non-invasively-detected biomarker.

Thus in some of any of the embodiments of the present disclosure, the method further includes:
automatically measuring, acquiring or otherwise determining at least one personal pharmacodynamic parameter in the patient in the form of a perceived therapeutic and/or perceived adverse effect and/or a level of at least one biomarker, collectively referred to herein as personal pharmacodynamic feedback data or information;
automatically re-determining an adjusted vaporized amount of the agent based on the automatically acquired personal pharmacodynamic feedback data, or in general adjust the dose and regimen according to the acquired personal pharmacodynamic feedback data;
automatically configuring the device to deliver the adjusted vaporized amount, to thereby exhibit a pre-selected or a re-selected PK and/or PD profile in the patient;
whereby for that particular person, the adjusted vaporized amount becomes the pre-determined vaporized amount of the pharmaceutically active agent and the re-selected PK and/or PD profile becomes the pre-selected PK and/or PD profile.

It is noted herein that automatic determination of any PD effect, or the automatic determination of the vaporized amount of the pharmaceutically active agent, can be fully or partially applied in any of the embodiments of the present disclosure, including the initial calibration of the MDI device, the re-configuration of the device during the personalization process, and/or the self-titration process.

Co-Administration:

It is noted herein that the method and/or device, according to some of any embodiments of the present disclosure, is suitable for pulmonary delivering of more than one pharmacologically active agent to a patient, wherein the device is configured to deliver independently a pre-determined vaporized amount of each the agents controllably, accurately and reproducibly.

According to some embodiments, co-administration of more than one active agent is carried out so as to achieve a desired balance between therapeutic (desired; positive; wanted) effects and adverse (undesired; negative; unwanted) effects. Such balance may be achieved for example when one active agent, while having some or no direct therapeutic effect, has the capacity to lower an adverse effect caused by the other co-administered active agent. In another example, different active agents induce similar and cumulative desired effects and different non-cumulative undesired effects; in which case such two such agents can be co-administered to induce a cumulative (e.g., double) desired effect while inducing substantially lower (e.g., single) undesired effect, compared to a 2-fold dose of each given individually. Optionally, the second agent has an effect that reduces and/or changes the nature of an adverse effect of the first agent. In such cases, the amount of the first agent (and the desired effect itself) may be increased, without increasing, and optionally while decreasing, the undesired effects thereof. This approach allows a higher dose for achieving a desired effect in treatment while maintaining low levels of adverse effects.

According to some embodiments, these two or more agents can be contained in the same substance or in more than one substance. In some embodiments, at least one of the agents is in at least one plant material. Hence, according to some embodiments, the device and method presented herein are configured for delivering each of at least two pharmacologically active agents independently at a pre-determined vaporized amount, wherein the substance being heated in the device comprises both or all these pharmacologically active agents. Alternatively, the device comprises more than one substance, which comprises the pharmacologically active agents.

In some embodiments, a method of pulmonary delivering to a subject at least a first pharmacologically active agent and a second pharmacologically active agent is provided, wherein at least one of the agents being in at least one plant material; the method is carried out by independently delivering the agents to the subject using a metered dose inhaler device configured to vaporize at least a first pre-determined vaporized amount of the first agent and at least a second pre-determined vaporized amount of the second agent upon controllably heating the plant material, wherein heating is effected such that the first pre-determined vaporized amount is delivered to the subject successively, concomitantly and/or at least partially overlapping with the second pre-determined vaporized amount, and wherein each of the pre-determined vaporized amounts of each of the agents induces in the subject independently at least one pharmacokinetic effect and/or at least one pharmacodynamic effect.

According to an aspect of some embodiments of the present disclosure, there is provided a method of pulmonary delivering to a subject at least a first pharmacologically active agent and a second pharmacologically active agent, at least one of which being in at least one plant material; the method is carried out by:
independently delivering the agents to the subject using a metered dose inhaler device configured to vaporize at least a first pre-determined vaporized amount of the first agent and at least a second pre-determined vaporized amount of the second agent upon controllably heating the at least one plant material,
wherein heating is effected such that the first pre-determined vaporized amount is delivered to the subject successively, concomitantly and/or at least partially overlapping with the second pre-determined vaporized amount, and wherein each of the pre-determined vaporized amounts of each of the agents induces in the subject independently at least one pharmacokinetic effect and/or at least one pharmacodynamic effect.

A pulmonary delivery of more than one active agent to a subject (a patient) is generally known in the art as co-administration. The term "co-administration" as used herein, refers to a concomitant administration of more than one active agent to a subject, whereas in the context of embodiments presented herein, the term "concomitant" means that the co-administered active agents are present in the subject (PK), or otherwise induce an effect (PD), at similar, identical or partially overlapping periods of time. In some embodiments, the time interval between delivering at least one agent (first) and delivering at least one other agent (second) ranges between zero minutes to 30 minutes.

In the context of co-administration of more than one active agent, the terms "substantially simultaneous" and "rapid succession" correspond to the term "concomitant"

and "partially overlapping", as used herein, namely meaning that the period of time between an inhalation of a first agent and an inhalation of a second agent is sufficiently short to be regarded as a single inhalation. Optionally, a number of inhalations takes place within 5-30 minutes. Optionally, each inhalation in such "rapid succession" delivers to the user a different amount or a composition of one or more pharmaceutically active agents. Optionally, two or more of the inhalations provide the same composition and amount of the one or more pharmaceutically active agents. In some embodiments, an inhalation of a second agent is performed at such timing that a first active agent inhaled previously still induces at least one PD effect in the subject. In some embodiments, co-administration of more than one active agent by delivery thereof in rapid succession means that the inhaled agents have essentially the same effect as they would have had if inhaled in a single inhalation.

According to some embodiments, a time interval between delivering the first agent and delivering the second agent ranges between zero minutes to 30 minutes.

According to some embodiments, each of these agents can be delivered at a pre-determined vaporized amount. Hence, the device and the method presented herein are capable of and designed for delivering the plurality of pre-determined vaporized amounts, wherein these vaporized amounts may be the same or different.

According to some embodiments, each of these agents can be delivered at a pre-determined time interval. Hence, the device and the method presented herein are capable of and designed for delivering the plurality of pre-determined vaporized amounts at pre-determined time intervals, wherein these time intervals may be the same or different.

According to some embodiments, the device and method presented herein are capable of and designed for delivering a plurality of pre-determined vaporized amounts of each of the pharmacologically active agents, wherein the pre-determined vaporized amounts and the pre-determined time intervals may each be the same or different from one another.

In some embodiments, the co-administration is based on interdependencies between one or more PD effects induced by individual agents, namely a PD effect of one agent influences the level of a PD effect induced by the other agent. For example, in some embodiments, the pre-determined vaporized amounts of the first agent affects a level of the pharmacodynamic effect induced by the second agent. Optionally, the pre-determined vaporized amount of the first agent increases a level of a desired effect induced by the second agent (potentiation). Optionally, the pre-determined vaporized amount of the first agent reduces a level of the undesired effect induced by the second agent. Optionally, the first agent and the second agent induce a desired effect synergistically.

In some embodiments, the method of pulmonary delivering more than one active agent, a presented hereinabove, further includes:
  adjusting at least one of the first pre-determined vaporized amount and the second pre-determined vaporized amount so as to achieve the pre-determined pharmacokinetic effect and/or the pre-determined pharmacodynamic effect based on data indicative of at least one pharmacokinetic effect and/or at least one pharmacodynamic effect induced by the agent in the subject.

In some embodiments, the method further includes generating indicative data by monitoring at least one pharmacokinetic effect and/or at least one pharmacodynamic effect induced in the subject by at least one of the first agent and the second agent.

According to an aspect of some embodiments of the present disclosure, there is provided a method of vaporizing at least a first pharmacologically active agent and a second pharmacologically active agent, at least one of which being in at least one plant material and being suitable for pulmonary delivery to a patient, which is carried out by using a metered dose inhaler device configured to vaporize at least a first pre-determined vaporized amount of the first agent and at least a second pre-determined vaporized amount of the second agent upon controllably heating the plant material, wherein upon pulmonary delivering the agents to the subject, the heating is effected such that the first pre-determined vaporized amount is delivered to the subject successively, concomitantly and/or at least partially overlapping with the second pre-determined vaporized amount, and wherein upon pulmonary delivering the agents to the subject, each of the pre-determined vaporized amounts of each of the agents induces in the subject independently at least one pharmacokinetic effect and/or at least one pharmacodynamic effect.

According to an aspect of some embodiments of the present disclosure, there is provided a use of a metered dose inhaler device for vaporizing at least a first pharmacologically active agent and a second pharmacologically active agent, at least one of which being in at least one plant material and being suitable for pulmonary delivery to a patient, wherein the device is configured to vaporize at least a first pre-determined vaporized amount of the first agent and at least a second pre-determined vaporized amount of the second agent upon controllably heating the plant material, and wherein upon pulmonary delivering the agents to the subject, the heating is effected such that the first pre-determined vaporized amount is delivered to the subject successively, concomitantly and/or at least partially overlapping with the second pre-determined vaporized amount, and wherein upon pulmonary delivering the agents to the subject, each of the pre-determined vaporized amounts of each of the agents induces in the subject independently at least one pharmacokinetic effect and/or at least one pharmacodynamic effect.

Method of Treatment

According to an aspect of some embodiments of the present disclosure, there is provided a method of treating a patient suffering from a medical condition that is treatable by pulmonary delivering a vaporizable pharmaceutically active agent. The method, according to some of any of the embodiments of the present disclosure, is carried out by pulmonary delivering the agent to the patient from a metered dose inhaler device configured to release at least one pre-determined vaporized amount of the agent upon controllably heating a solid form of a substance comprising the agent. According to some embodiments, the pre-determined vaporized amount of the agent is selected to exhibit at least one pre-selected pharmacokinetic profile and/or at least one pre-selected pharmacodynamic profile of the agent in the patient.

Non-limiting representative medical conditions, treatable by pulmonary delivering a vaporizable pharmaceutically active agent, include neuropathic pain, phantom pain, nociceptive pain, psychogenic pain (psychalgia or somatoform pain), asthma, chronic obstructive pulmonary disease (COPD), Crohn's disease, multiple sclerosis (MS), generalized epilepsy with febrile seizures plus (GEFS+), spasticity, Dravet's Syndrome, seizures, epilepsy, psychiatric disorders, anxiety disorders, posttraumatic stress disorder (PTSD), insomnia, delirium, increased intra ocular pressure, bladder dysfunction, tics, Tourette symptoms, appetite variations, sexual dysfunction, inflammatory bowel disease (IBD), irritable bowel syndrome (IBS), hyper tension, septic and cardiogenic shock, drug addiction and craving, tremors and other movement disorders.

According to some of any of the embodiments of the present disclosure, the method is carried out by use of an MDI device which is configured to release a pre-determined vaporized amount such that a deviation of an actual vaporized amount of the agent, from the pre-determined vaporized amount of the agent, is 20% or less, 15% or less, 10% or less, or 5% or less of the pre-determined vaporized amount.

According to some of any of the embodiments of the present disclosure, the method is carried out such that a deviation of an actual pharmacokinetic profile from the pre-selected pharmacokinetic profile is 40% or less than of the pre-selected pharmacokinetic profile. Alternatively, the deviation is 35% or less, 30% or less, 25% or less, or 20% or less. It is noted that the deviation can be in the pharmacokinetic profile or in one or more pharmacokinetic parameters composting the profile, e.g., $C_t$ or $C_{max}$. Such deviations are expected to be low due to the low inter-variability of PK effects obtained when using an accurate, consistent and precise MDI device.

According to some of any of the embodiments of the present disclosure, the method is carried out such that a deviation between the perceived PD profile from the pre-selected PD profile at any given time point is 25% or less, 20% or less, 15% or less, 10% or less, or 5% or less. The deviation between the perceived PD profile from the pre-selected PD profile at any given time point can be assessed by determining a PD effect, as discussed hereinabove. The deviation is expected to be low also due to the low inter-variability of PK effects discussed hereinabove.

Since the device can be configured to deliver any accurate amount consistently so as to exhibit a pre-selected or pre-determined PD effect in the patient, the device and the method presented herein can effect a pre-selected or pre-determined PD profile which can be finely controlled so as to be:

within a level lower than a minimal level of a desired effect (for example below the therapeutic window);
ranging within a minimal level of said desired effect to a maximal level of said desired effect in which an undesired effect is tolerable and/or acceptable, namely substantially low or not exhibited or not perceived (for example within the therapeutic window;); and
within a level higher than a minimal level an undesired effect (for example above the therapeutic window).

In some embodiments, a minimal level of an adverse effect correlates to a maximal level of a therapeutic effect in which an adverse effect is not detected or perceived.

In some embodiments, the level of the pharmacodynamic profile that is higher than the minimal level of an adverse effect, is one wherein the higher level of the adverse effect is an acceptable level of the adverse effect. Any one of personal, medicinal and legal factors may determine the acceptability of the level of the adverse effect, such as, for example, personal preference, habits and endurance, pharmaceutical and professional safety considerations, as well as legal and social consideration.

In some embodiments, a "minimal level of a therapeutic effect" means a minimal detectable therapeutic effect. Optionally, such a minimal level is at least sufficient to justify treating a person with a given dose and/or regimen with one or more substances. Such justification may be based on, for example, the type and severity of adverse effects and on the effect that the treatment may have at the minimal level on the wellbeing of the patient. Optionally, the minimal therapeutic effect means a minimal effect that is perceived by the individual being treated. Optionally, justification for administering a dose and/or regimen aiming to achieve PK/PD effects below the therapeutic window may be to achieve a prophylactic treatment or reduce the consequences of an acute pain (breakthrough pain) and/or to prevent emergence of tolerance to the treatment.

As discussed hereinabove, according to some of any of the embodiments of the present disclosure, the pre-selected PD profile corresponds to the therapeutic window of the agent in the patient, namely ranges within a minimal level of the therapeutic effect to a maximal level of the therapeutic effect in which an adverse effect is acceptable.

At any pre-selected PD profile, the method and device provide high accuracy and reproducibility; hence, according to some of any of the embodiments of the present disclosure, the deviation of the perceived pharmacodynamic profile from the pre-selected pharmacodynamic profile at any given time point is 25% or less, 20% or less, 10% or less or 5% or less below the pre-selected PD profile, and/or 25% or less, 20% or less, 10% or less or 5% or less above said pre-selected PD profile.

A non-limiting examples of a medical condition treatable by pulmonary delivering a vaporizable pharmaceutically active agent, is pain, which is treatable by THC vaporized from *cannabis*.

A Metered Dose Inhaler (MDI) Device:

According to another aspect of some embodiments of the present disclosure, there is provided a metered dose inhaler (MDI) device configured for pulmonary delivery of a pre-determined vaporized amount of at least one pharmacologically active agent to a patient, wherein:

the device is configured to deliver said pre-determined vaporized amount of said agent upon controllably heating a solid form of a substance comprising said agent;
the pre-determined vaporized amount is selected such that it affords a pre-selected pharmacokinetic profile and/or a pre-selected pharmacodynamic profile of the agent in the patient; and
the pre-determined vaporized amount is derived by measuring at least one pharmacokinetic parameter and/or at least one pharmacodynamic parameter induced by the pulmonary delivering of the agent in the patient from the MDI device (PK/PD studies).

According to an aspect of some embodiments of the disclosure, there is provided a method for controlling a metered dose inhaler; the method is effected by:

heating plant material so as to vaporize at least one pre-determined vaporized amount of at least one pharmacologically active agent being in the plant material; and
controlling the pre-determined vaporized amount based on data indicative of at least one pharmacodynamic effect induced by the agent in the subject.

According to an aspect of some embodiments of the disclosure, there is provided a method of operating an MDI for pulmonary delivering to a subject of at least one pharmacologically active agent being in a plant material; the method is effected by:

selecting at least one pre-determined vaporized amount of the agent so as to achieve at least one pre-determined pharmacokinetic effect and/or at least one pre-determined pharmacodynamic effect induced by the agent in the subject; and vaporizing, the at least one pre-determined vaporized amount of the agent using the metered dose inhaler device for controllably heating the plant material.

According to some embodiments of the invention, the MDI device is further configured for communication with a patient interface circuitry and be integrated in a system designed to allow PK/PD data acquisition and input, patient records' storage, automatic or manual calibration, adjustment, resetting and re-determination of the initial presetting of the device by the patient and/or by a practitioner, as will be described in details hereinbelow.

According to some of any of the embodiments of the present disclosure, the method and device presented herein are also characterized by a high accuracy, consistency, precision and reproducibility, which are expressed by a minimal deviation between the actual vaporized amount of the agent being inhaled by the patient, and the pre-determined vaporized amount of the agent.

According to some of any of the embodiments of the present disclosure, the MDI device for controlled vaporization of at least one active pharmaceutically active agent from at least one type of substance by application of heat, comprises:

At least one cartridge (also referred to herein as a "dose unit") containing a substance that comprises at least one active pharmaceutically active agent;
a heating element adapted to apply heat to the substance to vaporize the pharmaceutically active agent; and
a mechanism adapted for moving the cartridge relative to a controller for powering the heating element.

In an embodiment of the invention, the device further comprises substance organized as plurality of cartridges arranged in a tape, a daisy or a magazine, the substance comprising the active pharmaceutically active agent. Optionally, the active pharmaceutically active agent is a restricted pharmaceutically active agent. Optionally or additionally, the active pharmaceutically active agent is selected from the group comprising: tetrahydrocannabinol (THC), salvinorin A, benzoylmethylecgonine, dimethyltryptamine, psilocybin. Optionally or additionally, the substance is organized with a pre-determined amount of the active pharmaceutically active agent per unit area of the each cartridge in the tape, the daisy or the magazine. Optionally or additionally, a thickness of the cartridge ranges from about 0.2 mm to about 2.0 mm. Optionally or additionally, the tape, the daisy or the magazine comprises about 5 grams to about 100 grams of the substance. Optionally or additionally, the tape, the daisy or the magazine comprises a sufficient amount of the active pharmaceutically active agent for at least two treatments. Optionally or additionally, the cartridge comprises a first material layer coupled to the substance, the first layer comprising apertures large enough to let gas escape but small enough to contain residue of the heated substance. Optionally or additionally, a diameter of the apertures ranges from 25 μm-500 μm. Optionally or additionally, the cartridge comprises a second material layer coupled to the substance, the second layer adapted to transmit heat to the substance without substantially distributing the heat across the second layer. Optionally or additionally, the heating element and the substance are held between the first and the second layers.

In an embodiment of the invention, the device further comprises an inhaler unit, the inhaler unit comprising a mouthpiece for inhalation of the pharmaceutically active agent, the mouthpiece forming fluid communication with a vapor chamber of the device, the vapor chamber comprising the vaporized active pharmaceutically active agent.

Optionally, the mouthpiece comprises a one-way valve to control fluid flow away from the vapor chamber. Optionally or additionally, the device further comprising a sensor in fluid communication with the mouthpiece, the sensor adapted to estimate an air flow rate and send a signal to a controller, the controller adapted for vaporizing the pharmaceutically active agent according to the airflow rate.

In an embodiment of the invention, the device further comprises a controller configured to synchronize the application of heat with the movement of a cartridge and/or with airflow rate effected by inhalation.

In an embodiment of the invention, the device further comprises circuitry for controlling (controller) activation of the heating element.

In an embodiment of the invention, the device further comprises a communication interface for communicating to one or more external computers and/or systems and/or patient/physician interfaces.

In an embodiment of the invention, the device further comprises a dose display meter for providing visual output of the vaporization of the pharmaceutically active agent. In an embodiment of the invention, the device is portable and weights no more than 300 grams.

In an embodiment of the invention, the device further comprises a memory adapted to hold at least one of prescription data and usage data, the memory coupled to the controller, the controller adapted to control at least one of the heating element and the mechanism according to the dose and/or regimen data.

In an embodiment of the invention, the device further comprises a unique ID adapted for tracking the device use by an associated patient.

In an embodiment of the invention, the device further comprises a sensor adapted to detect a physical breach of the device.

There is provided in accordance with an embodiment of the invention, a method for controlled vaporization of an active pharmaceutically active agent from a substance, the substance is organized as a cartridge, the method comprising;
applying heat to an area of the cartridge to vaporize a predetermined amount of the active pharmaceutically active agent and; moving the cartridge relative to a heat source.

Alternatively, the heating element is comprised within the cartridge, and the cartridge is moved relative to electrical contacts for powering the heating element.

In an embodiment of the invention, the method further comprises adjusting at least one of timing and speed of the moving to vaporize the active pharmaceutically active agent according to a delivery profile. Optionally, the substance comprises a macroscopic plant structure.

In an embodiment of the invention, the vaporizing comprises vaporizing during pulmonary delivery.

In an embodiment of the invention, the applying heat comprises applying heat to reach a target temperature in less than 500 milliseconds after a start signal.

There is provided in accordance with an embodiment of the invention, a method for controlled vaporization of at least one active pharmaceutically active agent from at least one type of substance by application of heat, the method comprising:
heating up multiple areas of substance organized as one or more cartridges with one user trigger, to release the at least one active pharmaceutically active agent.

Optionally, the areas comprise different active pharmaceutically active agents.

There is provided in accordance with an embodiment of the invention, a cartridge for therapeutic drug delivery comprising substance comprising an active pharmaceutically active agent, said substance organized with a predetermined amount of the active pharmaceutically active agent per unit area of said tape (cartridge), and a heating element comprised therein.

In an embodiment of the invention, a plurality of cartridges is organized as a roll of tape, a daisy or a magazine.

Illustrative Application:

According to some embodiments and aspects of the present disclosure, each and any method, device, interface, system or sub-system presented herein can be used for treating a medical condition treatable by a pharmacologically active agent, which is vaporizable from a solid substance. In some embodiments of the present disclosure, the substance is a plant material.

Some plants which can be used in the context of the present disclosure, include, without limitation, *Cannabis sativa, Cannabis indica, Cannabis ruderalis, Acacia* spp., *Amanita muscaria,* Yage, *Atropa belladonna, Areca catechu, Brugmansia* spp., *Brunfelsia latifolia, Desmanthus illinoensis, Banisteriopsis caapi, Trichocereus* spp., *Theobroma cacao, Capsicum* spp., *Cestrum* spp., *Erythroxylum coca, Solenostemon scutellarioides, Arundo donax, Coffea arabica, Datura* spp., *Desfontainia* spp., *Diplopterys cabrerana, Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper methysticum, Catha edulis, Mitragyna speciosa, Leonotis leonurus, Nymphaea* spp., *Nelumbo* spp., *Sophora secundiflora, Mucuna pruriens, Mandragora officinarum, Mimosa tenuiflora, Ipomoea violacea, Psilocybe* spp., *Panaeolus* spp., *Myristica fragrans, Turbina corymbosa, Passiflora incarnata, Lophophora williamsii, Phalaris* spp., *Duboisia hopwoodii, Papaver somniferum, Psychotria viridis,* spp., *Salvia divinorum, Combretum quadrangulare, Trichocereus pachanoi, Heimia salicifolia, Stipa robusta, Solandra* spp., *Hypericum perforatum, Peganum harmala, Tabernaemontana* spp., *Camellia sinensis, Nicotiana tabacum, rusticum, Virola theidora, Voacanga africana, Lactuca virosa, Artemisia absinthium, Ilex paraguariensis, Anadenanthera* spp., *Corynanthe yohimbe, Calea zacatechichi, Coffea* spp. (Rubiaceae), a Sapindaceae, *Camellia* spp., *Malvaceae* spp., *Aquifoliaceae* spp., *Hoodia,* spp. *Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis,* any part and any combination thereof.

Other plants and plant materials, which can be used beneficially to vaporize at least one pharmaceutically active agent in the context of embodiments of the present disclosure include, without limitation, Aloe Vera, *Angelica*, Anise, Ayahuasca (*Banisteriopsis caapi*), Barberry, Black Horehound, Blue Lotus, Burdock, Camomille/Chamomile, Caraway, Cat's Claw, Clove, Comfrey, Corn Silk, Couch Grass, Damiana, Damiana, Dandelion, *Ephedra, Eucalyptus*, Evening Primrose, Fennel, Feverfew, Fringe Tree, Garlic, Ginger, Ginkgo, *Ginseng*, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, *Sida Cordifolia*, Sinicuichi (Mayan Sun Opener), Spearmint, Sweet Flag, Syrian Rue (*Peganum harmala*), Thyme, Turmeric, Valerian, Wild Yam, Wormwood, Yarrow, Yerba Mate, Yohimbe, and any part and any combination thereof.

In some embodiments, the active agent is a terpenoid, alkaloid or cannabinoid. For example, in some embodiments, the active agent is a diterpenoid such as, but not limited to salvinorin A from *salvia*. In other embodiments, the active agent is an alkaloid such as, but not limited to, benzoylmethylecgonine from the coca plant, or the active agent is a tryptamine such as psilocybin from mushrooms. In alternative embodiments the active substance is dimethyltryptamine (DMT) from a variety of plants. In further embodiments, the active substance is nicotine from tobacco. In further embodiments, the active substance is a terpenoid, e.g., limonene, α-pinene, β-myrcene, linalool, β-caryophyllene, caryophyllene, nerolidol or phytol, present in various plant forms.

According to some embodiments, the plant material is selected from the group consisting of *Cannabis sativa, Cannabis indica,* and *Cannabis ruderalis,* and according to some embodiments, the plant is *Cannabis sativa*.

*Cannabis* is a natural source for vaporizable cannabinoids, which constitute a class of diverse chemical compounds that act on cannabinoid receptors found in cells of humans and other animals. Cannabinoids, which include endocannabinoids (produced in animals), phytocannabinoids (found in *cannabis* and some other plants) and synthetic cannabinoids (manufactured chemically), are known to bind to naturally receptor proteins, and repress neurotransmitter release in the brain. The primary psychoactive compound of *cannabis*, is the phytocannabinoid Δ9-tetrahydrocannabinol (THC).

Cannabidiol (CBD) is another major constituent of the plant, representing up to 40% in extracts of the plant resin. There are at least 85 different cannabinoids isolated from *cannabis*, exhibiting varied effects, which include cannabigerols (CBG), cannabichromenes (CBC), cannabinol (CBN), cannabinodiol (CBDL), cannabicyclol (CBL), cannabielsoin (CBE), cannabitriol (CBT), Cannabidivarin (CBDV), Tetrahydrocannabivarin (THCV) and other miscellaneous types.

Tetrahydrocannabinol (Delta-9-tetrahydrocannabinol; Δ9-THC; THC) is the primary psychoactive component of the *Cannabis* plant. Δ9-THC and Δ8-THC mimic the action of anandamide, a neurotransmitter produced naturally in mammals. These two THC's produce the psychoactive effects associated with *cannabis* by binding to the CB1 and CB2 cannabinoid receptors in the brain; it has been reported to exhibit approximately equal affinity for the CB1 and CB2 receptors. THC appears to ease moderate pain (analgesic) and to be neuroprotective, while studies also show that THC reduces neuroinflammation and stimulates neurogenesis.

Cannabidiol (CBD) is not considered to be psychoactive, and was thought not to affect the psychoactivity of THC. However, recent evidence shows that smokers of *cannabis* with a higher CBD/THC ratio were less likely to experience schizophrenia-like symptoms. This is supported by psychological tests, in which participants experience less intense psychotic-like effects when intravenous THC was co-administered with CBD.

Cannabidiol has a different affinity for CB1 and CB2 receptors compared to THC (CBD has a greater affinity for the CB2 receptor than for the CB1 receptor), but acts as an indirect antagonist of cannabinoid agonists. Recently it was found to be an antagonist at the putative new cannabinoid receptor, GPR55, a GPCR expressed in the caudate nucleus and putamen. Cannabidiol has also been shown to act as a 5-HT1A receptor agonist, an action that is involved in its antidepressant, anxiolytic, and neuroprotective effects. CBD is also reported to relieve convulsion, inflammation, anxiety, and nausea.

CBD is known to play a role in preventing the short-term memory loss associated with THC in mammals. CBD has been suggested as a therapeutic agent in the treatment of schizophrenia. Researchers discovered CBD's ability to "turn off" the activity of ID1, the gene responsible for metastasis in breast and other types of cancers, including the particularly aggressive triple negative breast cancer.

Hence, accordion to some embodiments of the present disclosure, the pharmacologically active agent is a cannabinoid selected from the group consisting of Δ9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), Cannabidivarin (CBDV), Tetrahydrocannabivarin (THCV) and cannabitriol (CBT), and according to some embodiments, the pharmacologically active agent is selected from the group consisting of Δ9-tetrahydrocannabinol (THC) and cannabidiol (CBD).

In some embodiments, the pulmonary delivery method described herein utilizes THC or, more specifically, $\Delta^9$-THC as the pharmaceutically active agent. In some embodiments, the THC dose (pre-determined vaporized amount) is about 0.1-2 mg, 0.2-2 mg, 0.1-4 mg, 0.1-5 mg, 0.1-8 mg, 0.1-10 mg which has been shown to be salutary analgesics for a heterogeneous variety of neuropathic pain conditions. Such low THC dose can be vaporized accurately and consistently from natural *cannabis* in an amount that ranges from 5 to 50 mg, 7 to 35 mg, 10 to 30 mg, 12 to 20 mg, depending on the total amount of $\Delta^9$-THC available in the *cannabis*. In some preferred embodiments, the *cannabis* contains about 20% $\Delta^9$-THC, and the amount of *cannabis* used in the inhaler for each dose ranges from 10.0 to 20.0 mg.

Thus, in some embodiments, a high resolution in determining and controlling the amount of a pharmaceutically active agent is provided by the pulmonary delivering method described herein. In some embodiments, individual pre-selected vaporized amounts (doses) of, e.g., THC, are released electronically (by heating a pre-weighed portion of *cannabis*), in amount increments of 0.1 mg, ranging from 0.1 to 6.0 mg, 0.3 to 1.7 mg, 0.1 to 2.0 mg, from 0.2 to 1.8 mg, from 0.5 to 2.0 mg, from 0.5 1.5 mg, including any subranges and any intermediate values therebetween.

In accordance with embodiments of the method provided herein, predictive PK/PD protocols are developed for vaporized cannabinoids, based on clinical data, accumulated individually for each patient as well on a cohort of patients, which account for the dose and regimen administered, based on individual and population parameters, as described hereinabove. These protocols accurately simulate the PK profile of a patient after delivering a pre-determined dose, or pre-determined regimen, and in parallel predict the PD profile which is composed of symptom relief (therapeutic effect) and psychoactive levels (adverse effect). Once a sub therapeutic level, and the adverse psychoactive level are correlated with PK and patient parameters, a relatively narrow therapeutic window is derived, in which the MDI device can precisely maintain in the patient, by automating specific pre-selected vaporized amounts (doses and/or regimen).

By inputting patient data, the protocol calculates the recommended dose and regimen for that specific patient in order to stay within the therapeutic window for a specific duration.

According to these embodiments, the device selectively administers different doses at different time intervals so as to prevent adverse effects while still alleviating symptoms.

A System for Pulmonary Delivery:

As discussed hereinabove, the method and device presented herein are highly suitable for personalization, self-titration, mechanization and automatization of an otherwise complex and challenging mode of administration and treatment of a variety of medical conditions; while any personalized treatment protocol presents challenges, a treatment based on pulmonary delivery of active agents vaporized by heat from natural substances is a task which has not been achieved hitherto.

Once the problem of accuracy, consistency and reproducibility is solved by using a the MDI device disclosed herein; and once the need for calibrating and presetting the device to stay within a desired therapeutic window, based on widely accepted PK/PD experimental parameters has been served, as disclosed herein, the present inventors have conceived an integrated system that can control the device using input collected from a variety of sources so as to provide a highly personalized and effective treatment for any given patient, also in real-time.

According to an aspect of some embodiments of the disclosure, there is provided a system that includes:
  a metered dose inhaler device for pulmonary delivering to a subject at least one pre-determined vaporized amount of at least one pharmacologically active agent being in a plant material by controllably heating the plant material so as to vaporize a pre-determined vaporized amount of the agent from the plant; and
  a controller associated with the inhaler device, and configured to control the pre-determined vaporized amount.

According to an aspect of some embodiments of the disclosure, there is provided a system of pulmonary delivering to a subject at least one pharmacologically active agent being in a plant material; the system includes:
  a metered dose inhaler device configured to vaporize at least one pre-determined vaporized amount of the agent upon controllably heating the plant material; and
  a controller configured to select the at least one pre-determined vaporized amount of the agent so as to achieve at least one pre-determined pharmacokinetic effect and/or at least one pre-determined pharmacodynamic effect induced by the agent in the subject.

According to an aspect of some embodiments of the disclosure, there is provided a system for pulmonary delivering to a subject at least a first pharmacologically active agent and a second pharmacologically active agent, at least one of which being in at least one plant material; the system includes:
  a metered dose inhaler device configured independently deliver the agents to the subject by heating the at least one plant material to vaporize at least a first pre-determined vaporized amount of the first agent and at least a second pre-determined vaporized amount of the second agent; and
  a controller configured to effect the heating of the first pre-determined vaporized successively, concomitantly and/or at least partially overlapping with the second pre-determined vaporized amount,
  wherein each of the pre-determined vaporized amounts of each of the agents is selected to induce in the subject independently at least one pharmacokinetic effect and/or at least one pharmacodynamic effect.

According to an aspect of some embodiments of the disclosure, there is provided a system that includes:

a metered dose inhaler device for pulmonary delivering to a subject at least one pre-determined vaporized amount of at least one pharmacologically active agent being in a plant material by controllably heating the plant material so as to vaporize a pre-determined vaporized amount of the agent from the plant; and a controller associated with the inhaler device, and configured to control the pre-determined vaporized amount, wherein the controller is configured to receive operation setting data pertaining to the pre-determined vaporized amount from a remote control device. In some embodiments, the remote control device is configured to receive data indicative of at least one pharmacodynamic effect induced by the agent in the subject, and further configured to determine and transmit operation setting data pertaining to the pre-determined vaporized amount.

According to an aspect of some embodiments of the disclosure, there is provided a system that includes:

a metered dose inhaler device for pulmonary delivering to a subject at least one pre-determined vaporized amount of at least one pharmacologically active agent being in a plant material by controllably heating the plant material so as to vaporize a pre-determined vaporized amount of the agent from the plant; and a controller associated with the inhaler device, and configured to control the pre-determined vaporized amount based on data indicative of at least one pharmacodynamic effect induced by the agent in the subject.

According to an aspect of some embodiments of the invention, there is provided a system that includes a metered dose inhaler device for pulmonary delivering at least one pre-determined amount of at least one pharmacologically active agent to a subject. The system further includes at least one sensor for monitoring at least one pharmacodynamic effect in the subject induced by the agent, e.g. a psychoactive effect; and a processing unit associated with the inhaler device and with said at least one sensor. In some embodiments, the processing unit is configured to determine the pre-determined amount based on the data received from the sensor. The amount, which is being determined and controlled, may be a single dose or a regimen.

The indicative data is obtainable from a variety of sources, such as statistical data of a pharmacodynamic effect induced by the agent in a population, a user history, preferences and habits, a physician prescription and the like. In some embodiments, the indicative data is obtainable via at least one sensor configured for monitoring pharmacodynamic effects in a subject and/or via a user interface device configured for inputting data obtainable from such as sensors. In some embodiments, the controller is configured to receive indicative data pertaining to a pharmacodynamic effect from a sensor and/or a user interface device.

According to some embodiments, the controller is in direct and/or indirect communication with a sensor and/or an interface device, namely the controller can be associated via direct communication with the source of the indicative data (sensor and/or interface device), or be associated therewith via a remote control device.

According to some embodiments, the system includes an inhaler device as described hereinabove, a controller as described hereinabove, and at least one sensor and/or a user interface as described hereinabove, each configured independently to provide to the controller data indicative of at least one PD effect induced by the active agent in the subject.

According to an aspect of some embodiments of the disclosure, there is provided a system that includes, without limitation:

a metered dose inhaler device for pulmonary delivering to a subject at least one pre-determined vaporized amount of at least one pharmacologically active agent being in a plant material by controllably heating the plant material so as to vaporize a pre-determined vaporized amount of the agent from the plant;

at least one sensor for monitoring at least one pharmacodynamic effect in the subject induced by the agent and/or a user interface device for inputting data obtained from at least one sensor for monitoring at least one pharmacodynamic effect in the subject induced by the agent; and a controller associated with the inhaler device and with the at least one sensor.

In some embodiments, the controller used in the system described herein is configured to control the pre-determined vaporized amount by controlling the heating of the substance (e.g., plant material). Controllably heating the plant material is effected, for example, by controlling at least one of a heating temperature, a heating pattern (which part of the plant material to heat), a heating rate (how many times the plant material is exposed to heat), a heating duration (how long the plant material is exposed to heat in any given heating event), and any combination thereof.

In some embodiments, the controller is configured to control the pre-determined vaporized amount by controlling the airflow in the inhaler device, for example by controlling duct opening, valves and shutters in the inhaler device.

In some embodiments, the controller is configured to control the pre-determined vaporized amount by controlling the timing of one or more inhalation events. For example, the pre-determined vaporized amount is delivered in more than one inhalation event, and the controller is configured to generate at least one alert signal to the subject to use the inhaler device at indicated time points, at indicated time intervals and any other schedule so as to complete the pulmonary delivery of the pre-determined vaporized amount to the subject.

In some embodiments, by controlling the abovementioned heating and airflow parameters in the inhaler device, the controller is used to adjust the pre-determined vaporized amount so as to achieve a pre-determined pharmacokinetic effect and/or a pre-determined pharmacodynamic effect based on the pharmacodynamic effect. In some embodiments, the controller is configured for effecting the adjustment of the pre-determined vaporized amount in real-time.

In general, the controller is used to carry out more complex treatment plans, such as a regimen, a delivery of more than one active agent, each having a different dose and/or regimen, and/or other dose and timing related adjustments. In some embodiments, a controller can be configured for adjusting the regimen so as to achieve a pre-determined pharmacokinetic effect and/or a pre-determined pharmacodynamic effect based on the pharmacodynamic effect. In some embodiments, the controller is configured for effecting a pre-defined regimen that comprises delivering at least two pre-determined vaporized amounts. In some embodiments, the controller is configured for real-time adjustment of various operational settings of the inhaler device and parameters of the pulmonary delivery.

According to some embodiments, the system further includes or may be in communication with a user interface device, which can be used to input information and data into the controller, and/or to display, transmit or otherwise output data and information from the controller. In some embodiments, the user interface comprises an output device for providing information to at least one of the following: the subject, a practitioner, a memory unit and a remote device (a server, a display, a remote monitoring system/device and the like). In some embodiments, the user interface device includes a smartphone device. A smartphone may include a touchscreen, a microphone, a speaker, a GPS receiver, an accelerometer, a thermometer, a light detector and the like.

In some embodiments, the controller is configured for monitoring at least one of the at least one pre-determined pharmacokinetic effect and/or the at least one pre-determined pharmacodynamic effect, based on data received via the user interface device. Accordingly, the controller is configured for adjusting the pre-determined vaporized amount in real-time.

An aspect of some embodiments relates to treating a subject with a low dose of inhaled THC. In some embodiments, the low dose comprises between 0.2-2 mg of THC. In some embodiments, the low dose is between 0.3 mg and 1.5 mg THC, between 0.5-1 mg THC, between 0.6 and 1.5 mg THC, between 0.75-1 mg THC, between 0.2-0.75, between 0.2-0.5 mg THC, and/or other sub ranges. In some embodiments, an actual amount of THC selected from the range of 0.2-2 mg THC is sufficient to reduce one or more treated symptoms (such as pain and/or nausea) without return of the symptom(s) to a pre-inhalation degree for a time period of at least one hour, at least 90 minutes, at least two hours, at least three hours, at least five hours, or intermediate or longer time periods. Optionally, the following low dose is delivered after at least two hours, after 90 minutes, after 110 minutes, after 130 minutes, after 150 minutes or intermediate, longer or shorter time periods. Alternatively, two consecutive low doses are delivered after at least four hours. Optionally, the low dose is delivered through a plurality of delivery events of even lower doses during a certain time period (for example, a plurality of delivery events during a 2 hour time period, with a dose of 0.5 mg THC delivered in each event). Optionally, the total amount delivered in the two hour time period is no more than a preset low dose. Optionally, the total dose is set at 1 mg or 1.5 mg/2 hours, such that the total inhaled amount during any such time period in the aforesaid example does not exceed the total dose.

In some embodiments, a period of time between successive delivery events is selected to be sufficient for the effect of THC to take place. Optionally, the time period is determined by the user. Alternatively, the time period is predetermined by a medical practitioner. In some embodiments, the device is configured to restrict delivery so that a time period of at least 10 minutes, at least 20 minutes, at least 30 minutes or intermediate, longer or shorter time periods exist between successive delivery events. In some embodiments, once a maximal low dose (e.g. 0.2-2 mg THC) is reached and/or when the already inhaled dose is shown to be sufficient to alleviate symptom(s) and/or an undesired effect has reached a maximal tolerated level (as sensed by the user), delivery of the next dose may be postponed to a later time. In some embodiments, a time period between successive delivery events is proportional to the amount of THC inhaled in the successive delivery events.

In some embodiments, the device automatically locks to prevent additional delivery, for example when a maximal dose per time period and/or a maximal low dose is reached. In an example in which the maximal dose is limited to a total of 1 mg THC in a four hour time period, 0.5 mg THC may be delivered at a first delivery event, the device may lock for two hours and then enable another delivery of 0.5 mg THC. Alternatively, after two delivery events of 0.5 mg THC each (with any time interval in between them), the device may lock for 4 hours. In some embodiments, a duration of the lock-out period is determined according to one or more parameters such as the type of source material used (e.g. a *cannabis* strain), the type of active-substance(s) delivered, usage data of the patient, prescription data, safety considerations, and/or others.

In some embodiments, the device is configured to deliver a plurality of low doses in a plurality of delivery events (optionally, each dose is lower than a maximal low dose) with a time interval between delivery events being sufficient for the user to estimate the effect of the THC that was delivered. Optionally, delivery is stopped when the maximal low dose is reached and/or when a sensed effect dictates a stop. In some embodiments, after this time point, no THC is delivered for at least 2 hours, 4 hours, 6 hours or intermediate, longer or shorter time periods. Optionally, the time period is proportionate to the total amount of THC delivered earlier. Optionally, the time period is measured relative to the first delivery event and/or relative to the time point in which the maximal dose was reached and/or relative to the last delivery event, after which sufficient time has passed to sense the effect of THC but no additional THC was delivered.

In some embodiments, one or more maximal amounts of active substance are allocated for predefined time periods, for example 0.5 mg for 2 hours, 0.6 mg for two hours, 0.75 mg for two hours, 1.5 mg for 3.5 hours, 3.5 mg for 10 hours. In some embodiments, two or more such maximal amounts and periods are allocated simultaneously (e.g. no more than 0.2 mg for 2 hours and no more than 0.5 mg for 6 hours). In some embodiments, the device operates according to a "budgetary" delivery profile in which an amount given at a certain time point is selected so that additional delivery can be provided within the predefined time period, without exceeding the maximal amount. Optionally, the amount is reduced at each successive delivery. Additionally or alternatively, the device allows "free" delivery per demand of the patient until the maximal amount defined per the time period is reached.

In some embodiments, upon an attempt of the patient to use the device (e.g. detection of inhalation and/or when the patient turns the device on or otherwise actuates the device) an amount to be provided is automatically calculated based on previous deliveries performed within a selected time period. If no amount may be provided at a given attempt, the device may either communicate this to the patient (e.g. via visible and/or audible signals) or provide an alternative active substance or even a placebo.

In some embodiments, the dose is low enough so that the intensity of the psychoactive effects of THC are not statistically significant compared to placebo, while a therapeutic effect of THC remains sufficient to alleviate symptoms. In some embodiments, the dose is low enough so that psychoactive effects of THC are mild and/or reversible and/or recede rapidly, while a therapeutic effect of THC remains sufficient to alleviate symptoms.

In some embodiments, a total of no more than 0.7 mg, no more than 1 mg, no more than 2.5 mg, no more than 3 mg, no more than 3.5 mg THC, no more than 5 mg, no more than 7.5 mg THC, no more than 8 mg THC, no more than 6 mg THC, no more than 10 mg THC or intermediate, larger or smaller amounts are delivered over a time period of 24 hours. In some embodiments, the maximal amount is delivered during the 24 hour time period in a plurality of delivery events, each providing no more than 2 mg THC, no more than 0.7 mg THC, no more than 0.5 mg THC, no more than 0.2 mg THC or no more than 0.1 mg THC. In some embodiments, over a 24 hour time period, no more than 8 delivery events, no more than 6 delivery events, no more than 5 delivery events, no more than 3 delivery events, no more than 1 delivery event, no more than 10 delivery events or intermediate, larger or smaller number of delivery events are provided, wherein in each delivery event a low dose of between 0.2-2 mg THC is delivered to the patient through inhalation. Optionally, additional delivery events take place but only very small, insignificant amounts of THC are delivered (for example less than 0.2 mg THC, less than 0.1 mg THC per delivery event).

An aspect of some embodiments relates to an inhaler configured for delivering one or more low doses of THC, each dose comprising no more than 2 mg THC, no more than 1 mg THC, no more than 0.75 mg THC, no more than 0.6 mg THC, no more than 0.5 mg THC, no more than 0.2 mg THC or intermediate, larger or smaller amounts of THC. Optionally, the THC is extracted by vaporizing (optionally without burning) a THC-comprising material.

As used herein, a THC-comprising material may mean material comprising THC or THC acid (THCA), which converts to THC upon vaporization. Thus, when THC-comprising material is said herein to comprise THC, this should be taken to mean that it comprises THC and/or THCA. THC-comprising material may comprise or consist of plant material, with or without added substances, including without limitation comprising synthetic and/or extracted THC and/or one or more other cannabinoids. Optionally the THC-comprising material comprises or consists of an inert carrier comprising synthetic and/or extracted THC. In some embodiments, an inert carrier is a carrier that does not react with THC and does not provide vapor in storing and operation conditions up to the end of delivery of THC to a user.

In some embodiments, the inhaler device is configured to control the amount of THC delivered to a subject by at least one of selecting one or more cartridges from a plurality of cartridges, each having a different amount of THC content, and/or controlling one or more parameters of THC extraction, including for example a heating profile applied to THC-comprising material and/or a pattern of airflow to the user and/or through the THC-comprising material.

In some embodiments, the inhaler is configured to limit the amount of THC extracted and/or the amount of THC delivered to a subject, for example using a controller configured to adjust one or more of: heating parameters of the THC-comprising material; the amount of THC-comprising material heated; regulation of airflow to the subject and/or airflow through the THC-comprising material. In some embodiments, the inhaler device is configured to limit the amount of THC by comprising one or more cartridges each packed with THC-comprising material at an amount in which the THC content is about two fold the amount of THC being extracted. Alternatively, the amount of THC in the THC-comprising material is about three times the amount of THC being extracted, about four times the amount being extracted, about 6 times the amount being extracted or intermediate, larger or smaller amounts. Optionally, the THC content of the material is selected in accordance with an extraction efficiency of the inhaler, for example in an inhaler with 60% extraction efficiency, to extract 2 mg THC, a THC content of the material being heated would be about 3.33 mg. In some embodiments, the inhaler comprises only one cartridge comprising material for a single dose only. Optionally, the inhaler is configured re-heat the same cartridge until all THC is extracted. Optionally, the cartridge is manually replaced by a user.

In some embodiments, a low dose of THC refers to a dose exiting the inhaler. In some embodiments, a low dose exiting the inhaler is equivalent to the dose entering the user's mouth and/or entering the user's respiratory tract. In some embodiments, at least 80%, at least 90% at least 95%, at least 99% or intermediate, higher lower percentages of the amount of THC exiting the inhaler (for example through the mouthpiece) is inhaled by the user.

In some embodiments, the specific low dose delivered (e.g. an amount between 0.2-2 mg THC) is selected so as to have one or more pharmacological effects on the user, for example reduce nausea, reduce a level of pain, increase appetite, reduce fatigue and/or other effects. Optionally, the specific low dose is selected in accordance with a sub-indication of the user, for example 0.5 mg THC is prescribed for treating a low level of nausea, 1 mg THC is prescribed for treating an intermediate level of nausea, 1.5 mg THC is prescribed for treating a high level of nausea; for example 0.3 mg THC is prescribed for treating mild pain, 0.7 mg THC is prescribed for treating intermediate pain, 1.7 mg THC is prescribed for treating a pulsating pain, and/or lower, intermediate, or higher doses selected according to a user indication or a sub-indication thereof.

In some embodiments, the inhaler is configured to deliver one or more other pharmacologically active substances sequentially or concomitantly with the THC.

An aspect of some embodiments relates to a system configured to deliver THC to a user. In some embodiments, the system may consist of one or more devices and/or systems and comprise a memory, a decision module, and an inhaler suitable for delivering the THC to the user. In some embodiments, the memory stores one or more scheduled regimens for delivery of THC to the user, each scheduled regimen defining one or more of: a maximal amount of THC to be delivered; a time period within which the maximal amount can be delivered; minimal and/or maximal time intervals between successive deliveries; compositions and/or amounts of other active substances (e.g. cannabinoids) and/or placebos delivered to the user; and/or other regimen related parameters. In some embodiments, the decision module is configured to read and/or receive the scheduled regimens from the memory and to make a decision whether delivery should take place. Optionally, the decision module is configured to make such decision at any given time point. In some embodiments, the inhaler reads and/or receives as input the decision made by the decision module, and delivery is performed accordingly. Optionally, a controller of the inhaler carries out delivery by controlling one or more of: heating of the THC-comprising material, airflow through the inhaler, powering and/or electrical coupling of certain components of the inhaler (e.g. electrodes of the heating element); and/or other.

In some embodiments, the memory and/or decision module are included in the inhaler device, for example as designated circuitry components of the controller. Additionally or alternatively, the memory and/or decision module are external to the inhaler, for example associated with a user interface device such as a smartphone, laptop, and/or any other personal device. Optionally, the memory, decision module and inhaler controller are configured to communicate with one another, for example via wireless communication.

In some embodiments, the decision module comprises or is operably connected to a timer and/or a clock, for determining delivery in accordance with the scheduled regimen. In some embodiments, the decision module starts a timer immediately after a delivery event. Optionally, the decision module places a lock on the delivery, for example for a predefined time period. Optionally, a decision is made in advance (for example a decision to lock the inhaler for a predefined time period) and applied locally. In some cases, the decision module may decide to remove a lock before the predefined time period elapsed.

Certain features and/or functions of a "controller" for example as described in this application may be attributed to the memory and/or decision module as well.

An aspect of some embodiments relates to delivery of active substances at predetermined ratios. Optionally, different ratios are delivered at different times. In some embodiments, a combination of THC and CBD at a predetermined THC:CBD ratio is delivered in a dose. Optionally, a following dose comprises a combination of THC and CBD at a THC:CBD ratio which is at least 10% larger than the ratio of the first dose. Alternatively, the second dose comprises a combination of THC and CBD at a ratio which is at least 10% smaller than the ratio of the first dose. In some embodiments, the first dose is extracted from a *cannabis* strain having a first predetermined THC:CBD ratio, and the second dose is extracted from a *cannabis* strain having a second predetermined THC:CBD ratio, different from the THC:CBD ratio of the first strain. Optionally, a mixture of strains of used. Optionally, one or more extracted, purified and/or synthetic cannabinoids are used and/or added to a dose of *cannabis*, thereby to control or modify a proportion between the substances.

An aspect of some embodiments relates to an inhaler comprising a total amount of active substance (such as THC and/or other cannabinoid) sufficient for treating a patient only for a predefined time period such as a day, a week, a month, or intermediate, longer or shorter time periods. In an example, the inhaler comprises a total of no more than 3 mg, 5 mg, 7 mg, 10 mg, 20 mg, 30 mg, or intermediate, larger or smaller amounts of THC for delivery over a week; in another example, the inhaler comprises no more than 10 mg, 50 mg, 100 mg, 200 mg or intermediate, larger or smaller amounts of THC for delivery over a month. A potential advantage of an inhaler comprising a small amount of active substance which is sufficient only for treating the patient to alleviate symptoms may include reducing a likelihood of abuse, for example since the amount of restricted substance is so small that it is not sufficient to bring one to a high psychoactive state.

FIG. 1 is a schematic diagram of a system comprising an MDI device (also referred to herein as "inhaler device"), a physician interface and/or a patient interface, according to some embodiments of the invention.

In some embodiments, MDI device 901 is configured to communicate with a physician interface 903 and/or with a patient interface 905. In some embodiments, MDI device 901 is configured to receive input from one or both of the interfaces 903 and/or 905. Additionally or alternatively, MDI device 901 is configured to send output to one or both of the interfaces 903 and/or 907.

In some embodiments, communication between the system components is performed via one or more data transfer means such as a USB connection, a cable connection, a wireless connection, and/or any suitable wired and/or wireless communication protocol.

In some embodiments, communication between the system components is performed through one or more communication modules, such as communication module 907 of MDI device 901, communication module 909 of physician interface 903, and/or communication module 911 of patient interface 905.

In some embodiments, MDI device 901 comprises a controller 913, configured, for example, to activate heating of the substance to thereby vaporize the active agent, control the heating profile and/or activation of heat, control a cartridge feed mechanism of the MDI device, read data from a memory 919 of MDI device 901, control power usage, and/or other functions. In some embodiments, controller 913 communicates with a memory 919. Optionally, memory 919 is configured to store prescription data, personal usage data, patient details, personal PD effects obtained from the patient, dose and/or regimen modifications, parameters obtained from the patient in response to a change in a dose and/or regimen, and/or other values or information. In some embodiments, controller 913 activates pulmonary delivery of the active agent according to dose and/or regimen data stored in memory 919. In some embodiments, memory 919 is configured to store usage data and/or feedback data from the patient with respect to a specific dose and/or regimen and/or with respect to a pre-selected (desired) PD profile of the active agent in the patient.

In some embodiments, physician interface 903, comprising, for example, one or more of a controller 915, a memory 921 and/or a communication module 909, is configured on a personal computer (tablet computer, laptop computer, desktop computer, or others), a mobile device such as a smartphone, a handheld device, a wearable device, a wrist device or an integrated eyewear device, a clinic or hospital monitor and/or any other suitable device. Optionally, the physician is provided with remote access to MDI device 901. Additionally or alternatively, physician activates MDI device 901 directly. In some embodiments, the physician pre-programs (pre-calibrates or presets) MDI device 901 with a pre-determined vaporized amount (dose and/or regimen) suitable for an individual patient. In some embodiments, data is sent from physician interface 903 to patient interface 905, for example for instructing the patient or for effecting preset adjustments.

In some embodiments, patient interface 905, comprising, for example, one or more of a controller 917, a memory 923 and/or a communication module 911, is configured on a personal computer (tablet computer, laptop computer, desktop computer, or others), a mobile device such as a smartphone, and/or on MDI device 901 itself.

In some embodiments, patient interface 905 receives an input 929. The input may be received from one or more of the patient, the physician interface, the database server, the MDI device. Examples of various types of inputs may include a dose and/or regimen defined by the physician and received on the physician interface, a current personal PD effect of the patient, inserted by the patient and/or obtained from the patient, personal usage statistics recorded for example on the database server and/or on the memory of the MDI device, an indication of inhalation duration and/or inhalation volume sensed by the MDI device, and/or other types of input.

In some embodiments, patient interface 905 comprises a display 927. Optionally, the display is an interactive display, for example a touch screen of a smartphone, a handheld device, a wearable device, a wrist device or an integrated eyewear device.

In some cases, certain functions such as transferring data to the physician, accessing the database to acquire information such as user/patient instructions, and/or other functions are enabled by patient interface 905, while other function such as modifying the pre-determined vaporized amount (dose) and/or regimen (plurality of doses), viewing protocols of other patients, and/or other functions are not permitted by patient interface 905. Optionally, the physician sets the patient interface access definitions per an individual patient.

In some embodiments, patient interface 905 and/or MDI device 901 are configured to notify the patient every time a pulmonary delivery (an inhalation) is due.

Optionally, the notice is provided automatically based on a scheduled regimen stored in the memory. Additionally or alternatively, the notice is set by the patient. Additionally or alternatively, the notice is issued by the physician.

In some embodiments, one or more of the system components communicates with a database server 925, by receiving input from the database and/or sending out information to the database. In some embodiments, the database comprises individual data of the patient, for example including medical history of the patient, data transmitted by MDI device 901, input data from the physician, input data from the patient, and/or other information. Optionally, the database server is configured to perform calculations on the data. In some embodiments, database server 925 comprises collective data, including, for example, one or more of clinical experiment results, results of other patients, research data, and/or other data. Optionally, database server 925 communicates with a plurality of treatment systems being used by various patients. Data from various interactions between patients and the MDI device is collected in the central database, continuously learning individual usage patterns of patients and recommending dose and/or regimen accordingly. Utilizing the collective user database may improve generating of accurate predictive dose and/or regimen for current and new patients, improving the overall therapeutic success rate of the treatment.

In some embodiments, according to personal feedback data obtained from the patient using MDI device 901 and/or by patient interface 905, the pre-determined vaporized amount (dose and/or regimen) is automatically modified by controller 917 of the patient interface and/or by controller 913 of the MDI device to compensate for inadequate settings or misuse of the MDI device, for example in a situation in which the patient does not use the MDI device when instructed to, and/or use the MDI device is carried out at a timing different than the preset regimen. One or more actions may be taken in response, for example postponing the next dose, increasing or decreasing the next dose (and/or following doses), and/or otherwise altering the regimen.

In some embodiments, a patient using MDI device 901 may wish to schedule their dose and/or regimen in a way in which possible adverse effects least interfere with the patient's daily activities. While certain adverse effects are tolerable in a home setting or at certain time of day, and are an acceptable trade off for symptom relief, these adverse effects may be undesirable when the patient is engaged in activities such as driving, attending a meeting, and/or other activities. Optionally, using patient interface 905 and/or by directly activating MDI device 901, the patient schedules a dose and/or regimen in a manner that least interferes with their planned activities.

Additionally or alternatively, MDI device 901 and/or patient interface 905 are configured to actively impose a certain dose and/or regimen, for example based on input from the patient. In an example, the patient inserts their planned daily activities and timing of those activities, and the dose and/or regimen is automatically modified accordingly. Optionally, the dose and/or regimen is automatically modified to ensure that the patient is in a suitable condition to perform the planned activity, for example ensuring that during driving the level of an adverse effect is relatively low or not perceived.

In some embodiments, the patient may voluntarily modify the dose and/or regimen, for example using patient interface 905. Optionally, the extent of modifications is limited, to prevent a condition in which the patient is at risk, for example preventing overdosing.

In some embodiments, the patient may simply use MDI device 901, even when not specifically instructed to. In such a case, the next dose and/or regimen may be automatically modified in response to the usage. Optionally, the patient is notified about modifications in the dose and/or regimen through patient interface 905. Additionally or alternatively, the physician is notified about such changes, for example through physician interface 903.

Figure 2:
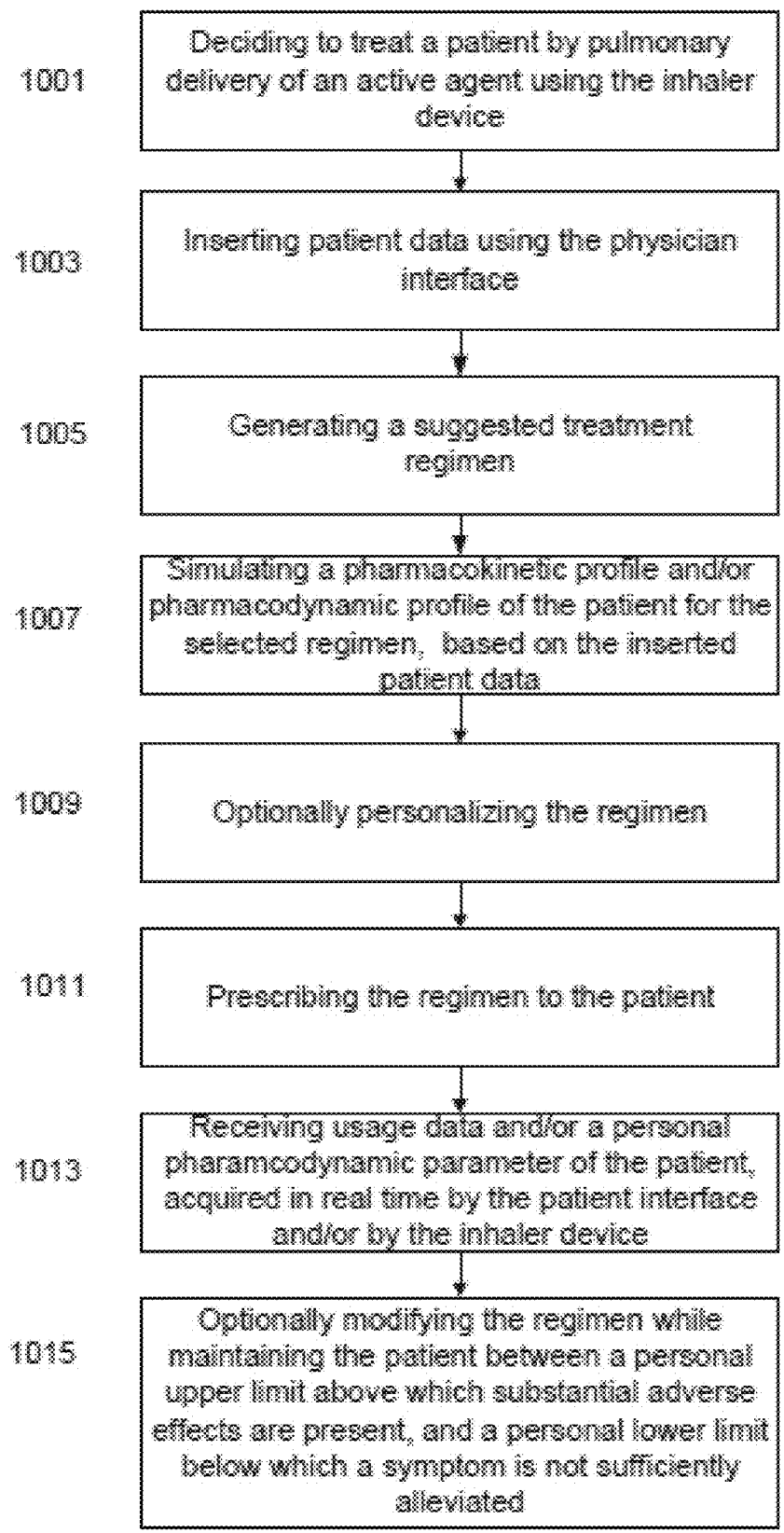
FIG. 2 is a flowchart of a method for prescribing a personalized regimen to a patient, according to some embodiments of the present disclosure.

FIG. 2 is a flowchart of a method for prescribing a regimen to a patient using an MDI device for delivery of at least one active agent, according to some embodiments of the invention.

In some embodiments, a physician may decide to treat a patient by effecting a pulmonary delivery of one or more active agents by an MDI device (1001).

In some embodiments, patient data such as one or more of, for example, PK variables (e.g., age, gender, BMI etc.), pathophysiological status, pharmocogenetic and/or pharmacogenomic variables and/or other parameters are inserted to the system (1003), for example by the physician and/or other clinical personnel. Optionally, the patient's parameters and personal variables are inserted using the physician interface.

In some embodiments, a suggested dose and/or regimen is generated (1005). Optionally, the dose and/or regimen is generated automatically, for example by software of the physician interface. Additionally or alternatively, the dose and/or regimen is planned by the physician. In some embodiments, the dose and/or regimen is generated by matching the inserted patient data to a pre-defined dose and/or regimen using data from a database, or according to personal feedback data, or for example according to a look up table.

In some embodiments, a simulation of an expected PK/PD profile of the patient for the selected dose and/or regimen is produced (1007). In some embodiments, an expected PK/PD profile, including for example therapeutic effects and/or adverse effects is simulated. In some embodiments, by correlating between the pharmacodynamic profile and/or pharmacokinetic profile and the patient's personal data, a therapeutic window is selected. Optionally, the PK/PD profile simulations and/or the pre-selected therapeutic window are graphically displayed to the physician, for example on a display of the physician's interface. When considering the simulations, a physician may decide to modify the dose and/or regimen to better suit (personalized) it to the patient (1009). In some cases, the physician may decide to change proposed dose and/or regimen parameters such as one or more of dose, dosing, regimen or total treatment duration, and/or other treatment parameters.

In some cases, treating includes administering two or more substances, simultaneously or sequentially, to obtain a desired therapeutic effect in the patient. The system, according to some of any of the embodiments of the present disclosure, provides the ability to use the MDI for delivering more than one pharmaceutically active agents (from one or more substances) at any ratio or pre-determined vaporized amounts so as to exhibit a pre-selected PD profile (e.g., maintaining an individual patient within the therapeutic window calculated per the patient). In some embodiments, different doses are selectively administered according to a regimen so as to prevent adverse effects while still alleviating symptoms.

In some embodiments, the selected (and optionally refined) dose and/or regimen is prescribed to the patient (1011).

In some embodiments, as a follow up and over a time period in which the patient is treated (e.g., over several hours, over a day, over a week, over a month, and/or intermediate, longer or shorter periods), the physician receives one or more indications such as indications relating to the patient's general usage of the device, indications relating to dose and/or regimen administered to the patient, substance consumed by the patient, one or more personal PD effects of the patient, for example relating to the presence of adverse effects, such as the psychoactive level and/or indications relating to the symptom intensity such as the pain level, and/or a level of one or more biomarkers and/or other indications (1013). Optionally, one or more indications are provided in real-time. Additionally or alternatively, the indications are provided at the end of a pulmonary delivery of the agent. Additionally or alternatively, the indications are provided on demand of the physician. Additionally or alternatively, the patient decides when to send indications to the physician.

In some embodiments, the indications are transmitted to the physician by the MDI device and/or by the patient interface, automatically and/or in response to an instruction from the physician and/or the patient. Optionally, one or more indications are stored in the database for future reference.

In some embodiments, based on the provided indications, the dose and/or regimen is adjusted or otherwise modified (1015). Optionally, modification is performed in real-time. In some embodiments, a specific dose and/or regimen is modified, optionally in real-time. In some embodiments, the dose and/or regimen is modified while taking into account upper and lower PD effect limits defined individually per the patient. An upper limit may allow dose and/or regimen above which substantial adverse effects are present. A lower limit may allow dose and/or regimen below which a symptom, which was intended to be treated by delivery of the active agent, is not sufficiently alleviated.

FIG. 3 is a flowchart of a method for obtaining feedback data from a patient and modifying/adjusting a dose and/or regimen accordingly, according to some embodiments of the invention.

In some embodiments, a personal PD effect of the patient is obtained (1201).

In some embodiments, the PD effect relates to an adverse effect such as a psychoactive level, a therapeutic effect such as a pain level, and/or a change in any of those levels thereof. The PD effect may include an absolute quantification of the level, and/or a relative quantification of the level, assessed, for example, with respect to a level measured before a delivery of single dose and/or before a delivery of dosing and/or regimen. The PD effect may be obtained before, during and/or after a delivery of single dose and/or before, during and/or after a delivery of dosing and/or regimen and/or before, during and/or after a general time period over which treatment is provided to the patient.

In some embodiments, the PD effect is provided directly by the patient, for example using the patient interface. In some embodiments, the patient can manually adjust a visual representation of the PD effect, based on a personal determination of the level of the PD effect. In an example, the patient may raise or lower a bar on a graph indicating a pain level, for example on a touch screen of a cellular phone and/or any other personal device on which the patient interface is configured.

In some embodiments, patients who are unable to articulate levels of the PD effect may utilize an interactive set of tools to assist them in determining their current level of the PD effect, for example as further described herein.

Additionally or alternatively to a conscious, personally perceived PD effect indicated by the patient, a personal PD effect such as a biomarker is obtained by the patient interface and/or by the system, for example using a sensor. In some embodiments, one or more standard components of a cellular phone and/or personal computer on which the patient interface is configured as acts as a sensor for obtaining the parameter. Some components which may be used as sensors for obtaining PD effects from the patient may include: a touch screen, may be used for example to assess dexterity, eye-hand coordination, and/or a memory and cognition state; a gyroscope, accelerometer, proximity sensor and/or gesture sensor such as IR sensor may be used, for example, to assess motor skills; a camera and/or light source may be used, for example, to detect visual tracking, saccade variance, eye vascular expansion, pupil dilation and/or pulsation; an RGB illumination may be used, for example, to assess environmental perception; a magnetometer and/or GPS may be used, for example, to assess orientation; a speaker and/or microphone may be used, for example, to assess auditory and/or vocal skills; a temperature and/or humidity sensor may be used, for example, to assess a body temperature.

In some embodiments, the MDI device is configured to obtain personal feedback data. In an example, the MDI device comprises a flow sensor and/or a pressure sensor.

Optionally, a breathing related indication of the patient is obtained using the flow and/or pressure sensor. In some embodiments, the sensor is adapted to detect a volume of inhalation. Since a correlation may exist between inhalation volume and a PD effect, such as a pain level, in some embodiments, a flow and/or pressure measurement is initiated to determine a PD effect in the patient.

Once one or more personal PD effects are obtained, the dose and/or regimen may be modified accordingly (1203). In some embodiments, the dose and/or regimen is modified, on one hand, to improve or otherwise change a condition of the patient based on the provided indication, and, on the other hand, to achieve a pre-selected pharmacodynamic profile, such as maintaining the patient within the therapeutic window—between a lower limit of a therapeutic effect that provides symptom relief, and a higher limit of an adverse effect in which the adverse effect level is still tolerable. In some embodiments, the MDI device can be configured such that when below a minimal therapeutic effect, input by the patient may increase the dose and/or adjust the regimen in frequency and/or in quantity. Optionally, the dose and/or regimen is modified to obtain a level above a minimal therapeutic effect. Additionally or alternatively, the dose and/or regimen is modified as much as the maximal level of an adverse effect permits.

Figure 4:
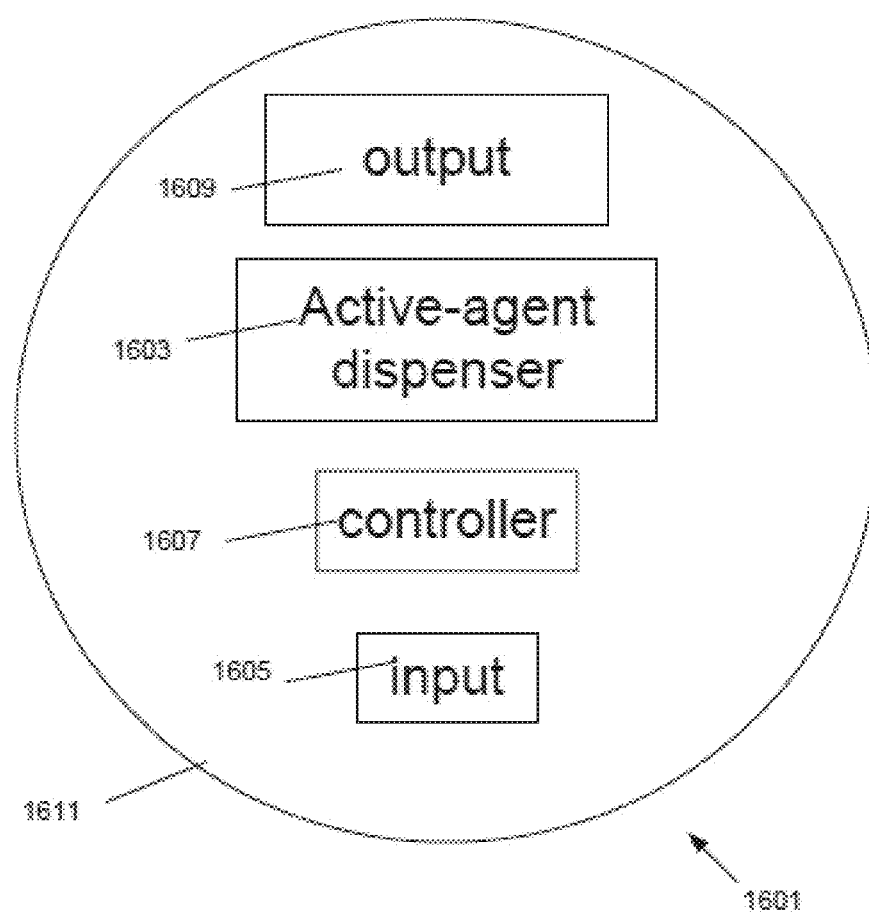
FIG. 4 is a schematic diagram of a metered dose inhaler device configured to provide automated controlled pulmonary delivery of one or more active agents, according to some embodiments of the present disclosure.

FIG. 4 is a schematic diagram of a metered dose inhaler device configured to provide automated controlled pulmonary delivery of one or more active agents, according to some embodiments of the invention. Patent publications WO2016/001923, WO2016/001925, WO2016/001926, WO2016/001921 incorporated herein by reference, describe devices and/or systems that may be used within the framework of some embodiments of the present application.

In some embodiments, device 1601 comprises substance dispenser 1603, e.g., a dispenser for the substance that contains the pharmaceutically active agent and allows the pharmaceutically active agent to be inhaled therefrom. In some embodiments, the substance dispenser comprises, or is in communication with, a source of at least one substance from which the active agent originates, and a mechanism for processing the substance to obtain a deliverable active agent, for example as described hereinabove.

The substance may comprise various forms, such as, for example, a solid bulk, solid particles, a solution or a powder. Optionally, the substance is contained within a cartridge, a capsule, and/or other containers. In some embodiments, the processing mechanism includes one or more of, for example, heating (e.g., for vaporizing), turning to aerosol, causing a chemical reaction, for example by mixing with other materials, releasing substance from a container such as by breaking open a capsule, pressure propellant, mobilizing and/or other types of processing. Alternatively, the active agent is already in a ready to use form and does not require any processing before delivering to the user by heating the substance.

In some embodiments, MDI device 1601 comprises input module 1605. Optionally, input module 1605 is configured to receive data pertaining to a dose and/or a regimen according to which the active agent will be delivered to the patient. Additionally or alternatively, input module 1605 is configured to receive one or more indications from a sensor (not shown in this figure), comprised within device 1601 and/or configured externally to device 1601.

In some embodiments, MDI device 1601 comprises a controller 1607, configured to initiate and/or modify and/or cease the pulmonary delivery of the pharmaceutically active agent. In some embodiments, controller 1607 operates substance dispenser 1603, for example activating heating of the substance by a heating element. In some embodiments, controller 1607 activates delivery of a pre-determined vaporized amount of the agent, such as the dose and/or regimen received as input. In some embodiments, controller 1607 controls the flow of the active agent, for example by activating one or more valves. In some embodiments, the controller is adapted to release the agent based on a current flow rate.

In some embodiments, MDI device 1601 comprises an output 1609. Optionally, output 1609 is configured as a mouthpiece to be engaged by the patient. Alternatively, to a mouthpiece, output 1609 may be configured as a breathing mask, a pacifier-like attachment for infants, and/or other structures suitable for delivering the flow of vapors to the patient.

In some embodiments, components of device 1601 such as the substance dispenser and/or the controller and/or other components are contained within a housing 1611. Optionally, the housing is shaped and sized to be used as a handheld device.

In some embodiments, MDI device 1601 comprises a flow control mechanism.

Optionally, the flow of vapors is controlled using one or more valves. In some embodiments, the flow is selected and/or modified per the individual patient, for example by timing the delivery and allowing flow of the active agent to the patient only during inhalation of the patient, indicated for example by a sensor incorporated in the MDI device. In some embodiments, the device is configured to modify the flow to allow the patient to instinctively identify when to cease inhalation, inhale deeper, and/or otherwise change the breathing rhythm and/or intensity. In an example, a pulse of increased flow volume is delivered by the device to indicate to the patient to cease inhalation.

In some embodiments, the flow is selected and/or modified to reduce an amount of active agent that remains trapped within the outflow tract of the device, and is not delivered to the patient. In some cases, the amount of trapped active agent is reduced to a known, predefined amount by controlling the flow.

In some embodiments, the flow is controlled by controller 1607. Optionally, the flow is controlled according to data received on input module 1605, data acquired by a sensor, and/or other indications.

A potential advantage of a device comprising a flow control mechanism which is operable per an individual patient may include improved accuracy of delivery to the patient, with respect to timing and/or pre-determined vaporized amounts of active agent delivered by the device, improving the performance of the system/MDI device.

Figure 5:
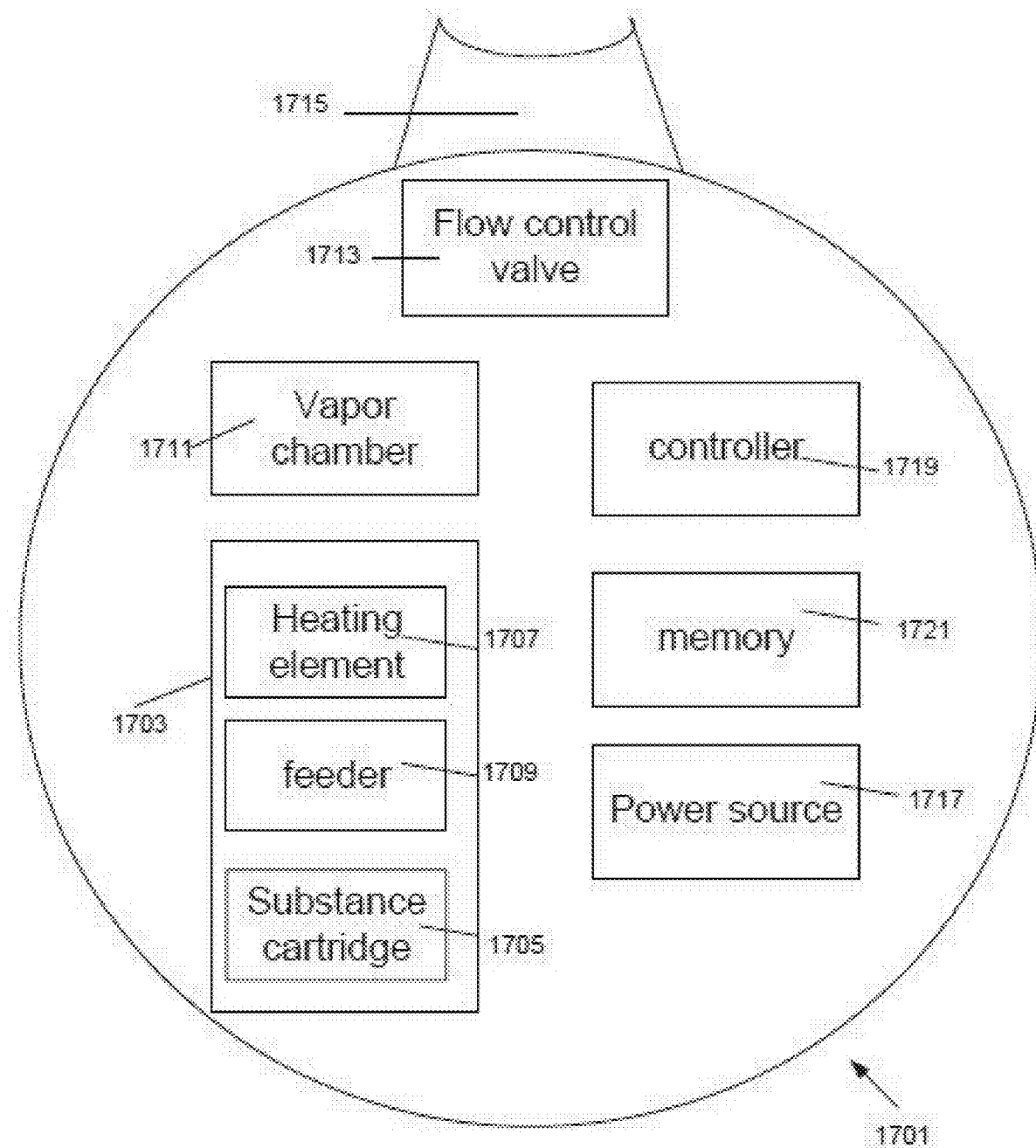
FIG. 5 is a schematic diagram of a configuration of an inhaler device, according to some embodiments of the present disclosure.

FIG. 5 is a schematic diagram of a configuration of an MDI device 1701, according to some embodiments of the invention.

In this configuration, the substance dispenser 1703 comprises a substance cartridge 1705, a heating element 1707, and a feeder 1709 which moves the substance cartridge relative to the heating element 1707, for example to be in contact with or in proximity to the heating element.

In some embodiments, the heating element is configured to provide localized heating, for example by conduction, convection and/or radiation. In some embodiments, a substance is heated sufficiently quickly to a temperature suitable for forming vapors of a vaporizable pharmaceutically active agent contained therein. In some embodiments, the substance is organized as a moving element, which can be selectively and/or locally activated. Optionally, the substance is organized into compacted shapes. Optionally, each shape represents a pre-determined vaporized amount.

In some embodiments, the vapors released from the substance collect within a vapor chamber 1711, from which they travel to the patient through an outflow tract.

Optionally, a valve 1713 is positioned along the tract to control the rate of flow.

In some embodiments, device 1701 comprises a mouthpiece 1715 from which the vapors are delivered to the patient in response to inhalation. Alternatively, mouthpiece 1715 can be attached to other elements, for example, to a mask and/or nasal cannula, optionally with supplemental oxygen, for example, to deliver therapy to debilitated patients. Optionally, mouthpiece is in fluid communication with valve 1713.

In some embodiments, device 1701 comprises a power source 1717, for example a battery, a manually wound spring, and/or a wall socket plug.

In some embodiments, device 1701 comprises a controller 1719, for example as described hereinabove, configured to control one or more of valve 1713, power source 1717, and/or the substance dispenser 1703 as a whole and/or separately control the components of the substance dispenser. In some embodiments, controller 1719 verifies that a substance cartridge is authorized for use.

In some embodiments, controller 1719 is in communication with memory 1721, which can be read by the controller and/or be written in.

Figure 6:
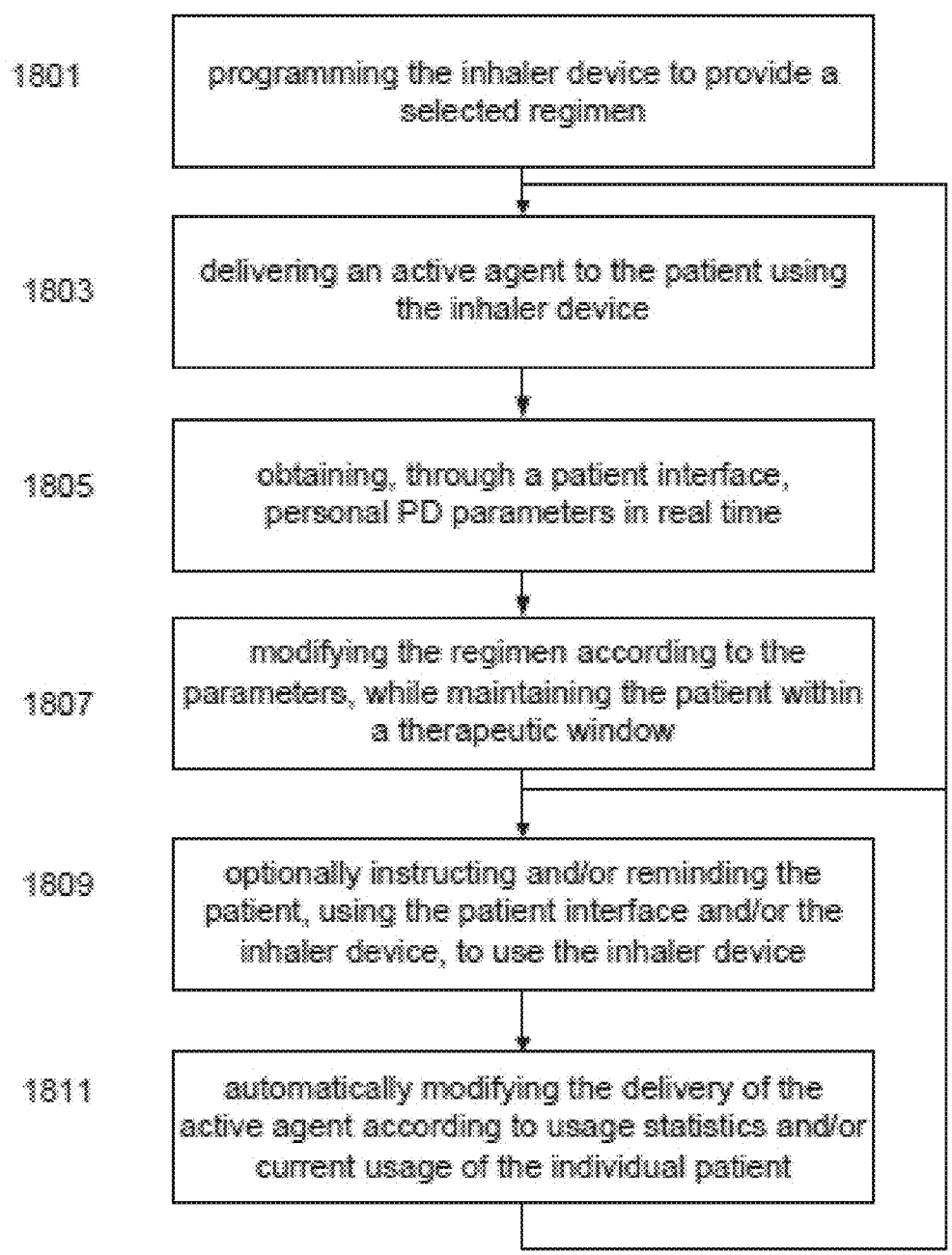
FIG. 6 is a flowchart of a method of treating an individual patient using a system according to FIG. 1, while maintaining the patient within a personalized therapeutic window, according to some embodiments of the present disclosure.

FIG. 6 a flowchart of a method of treating an individual patient using a system according to FIG. 1, while maintaining the patient within a therapeutic window, according to some embodiments of the invention.

In some embodiments, the MDI device is programmed with a pre-determined vaporized amount (dose and/or regimen) (1801). Optionally, the dose and/or regimen is set in the inhaler device by the physician, manually (such as by activating buttons on the device itself) and/or using the physician interface. Additionally or alternatively, the dose and/or regimen is set in the MDI device according to instructions sent from the patient interface.

In some embodiments, the MDI device is optionally configured for selecting at least one pre-determined vaporized amount for an inhalation session, which can include a plurality of inhalations, based on the dose unit's contents, and controlling at least one of heating and airflow in the device to control the pre-determined vaporized amount of an active agent provided to the user. In other words, based on the properties of the substance, which is packed into the dose unit, namely the amount of active agent(s) available therein for vaporization, the device can be configured to vaporize some or all of the available active agent(s) in the substance in a single or a plurality of inhalations, wherein the controllability over the vaporized amount in each inhalation is afforded by control over the heating level and duration, and the airflows output and duration in the device.

In some embodiments, the MDI device is activated to deliver the active agent to the patient (1803). In some embodiments, direct and/or indirect feedback data from the patient is obtained in real-time (1805). Optionally, feedback data is obtained during a pulmonary delivering (an inhalation session). A treatment may typically start with a pulmonary delivery, and end between 5-20 minutes thereafter, for example when the pre-selected pharmacodynamic profile has fully manifested for the active agent and/or at a later time. Additionally or alternatively, feedback data is obtained over a series of pulmonary deliveries, for example over a time period of 1 hour, 3 hours, 5 hours, 9 hours, 12 hours or intermediate, longer or shorter time periods. A protocol may include 5-10 pulmonary deliveries per day, in time intervals ranging between 15-180 minutes between successive pulmonary deliveries.

In some embodiments, the feedback data which is obtained from the patient includes personal PD effects such as therapeutic effects, for example symptom intensity, and/or adverse effects, for example a psychoactive state of the patient.

In some embodiments, the patient interface interacts with the patient to obtain the feedback data. In some embodiments, questions to the patient relating their current state are displayed on a screen, and the patient answers the questions. Such a question may be presented, for example, in the form of a bar indicating a pain level, for example, which the patient raises and/or lowers. Additionally or alternatively, feedback data is obtained by one or more applications, such as games, which the patient interacts with. Optionally, non-invasive biomarkers levels are estimated by analyzing the patient's input when interacting with the user interface. Additionally or alternatively, feedback data from the patient is obtained by measuring various biomarkers using one or more sensors, for example by utilizing components of a smartphone, a handheld device, a wearable device, a wrist device or an integrated eyewear device, to act as non-invasive biomarker sensors. In some embodiments, the personal PD effects are obtained periodically, for example semi-daily, daily, weekly, monthly, per demand such as before a dose and/or a series of doses, before and/or after alterations in dosing and/or regimen, or others.

In some embodiments, in response to the PD effects, a dose and/or regimen is modified (1809). Optionally, the dose and/or regimen is modified to achieve a desired effect, for example reduce pain level of the patient, while maintaining the patient within a therapeutic window. In some embodiments, the dose and/or regimen is iteratively modified by the patient interface. Modifications may take place a plurality of times, for example during, between or after one or more pulmonary deliveries, and/or over a total treatment time period (days, weeks, months, years) over which the patient is treated. The modification is limited by safety cutoffs, such as doses which may put the patient at risk.

In some embodiments, the patient interface and/or the MDI device remind the patient to perform one or more pulmonary deliveries (1811). Such a reminder may be provided as a visual signal (for example light indication), a sound, a vibration, a notification on a portable/handheld device, e.g. smartphone, a handheld device, a wearable device, a wrist device or an integrated eyewear device, or a combination thereof.

In some embodiments, usage data of the patient is recorded and stored in the MDI device memory and/or in the patient interface memory. Optionally, the delivery of the active agent is modified, potentially in real-time, according to usage data. For example, in a case in which the patient missed one or more pulmonary deliveries, the dose and/or regimen may be automatically modified to set a delivery of, for example, an increased amount of active agent in the following one or more pulmonary deliveries. In some embodiments, the record is transmitted to a physician which in turn updates the regimen and/or prescribes drug supply. Optionally, usage is recorded on a cartridge and is read when the cartridge is collected from the user.

Some potential advantages of recording use may include following up on treatment, improving treatment, reducing misuse and/or abuse which in some cases may lead to addiction.

In some embodiments, any one or more of the actions described in 1801-1811 may be repeated. Advantageously, obtaining personal PD effects and/or usage data from the patient repetitively may provide for ongoing adjustment of the dose and/or regimen, providing a flexible, precise and accurate personalized treatment to the patient based on an actual effect of the treatment on the individual patient.

Figure 7:
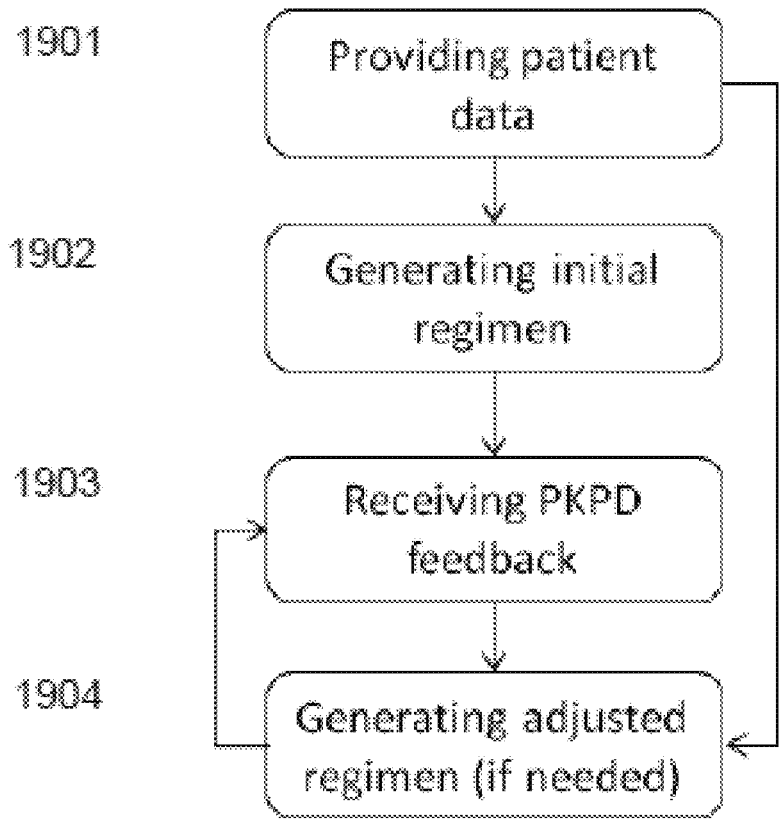
FIG. 7 presents a flowchart of a procedure for determining and administering a personal dosing and/or regimen for treating neurological pain in a human subject.

The following is an example for a procedure for determining and administering a personal dosing and/or regimen for treating a human subject by pulmonary delivery using an inhaler device, according to some embodiments of the present disclosure. The procedure is depicted in flowchart 1900 presented in FIG. 7.

Providing patient data (see, 1901 in FIG. 7) may include information about the patient's properties, including for example one or more of the patient's age, gender, weight, BMI, expected activity, etc., a recommended dosage and/or regimen and/or a syndrome or indication for which treatment is administered. Optionally, providing patient data (1901) also includes PK/PD data from one or more previous uses of an inhaler for the same active agent(s) and possibly also for the same indication. Optionally, providing patient data (1901) includes a correlation or set of correlations between a dose and the PK profile and/or PD profile of the patient over a period of time as recorded in one or more previous deliveries of the same one or more pharmaceutically active substances. Optionally, providing patient data (1901) includes data assembled from PK/PD profiles of a plurality of users or a population to which the user belongs.

Optionally, providing patient data (1901) includes treatment instructions and/or treatment preferences. Some examples for treatment instructions or preferences may include no dose during a given temporal window; allowing more drowsiness generally (e.g., for bedridden patients) or at a given time (e.g., initial treatment and/or during the night and/or when dealing with extreme symptoms); requiring alertness in given timeframe (e.g., when a patient expects to need alertness), and the like. Such instructions may be given a weighted value; for example, a patient may be less adamant on some instructions then others, for example the patient may prefer having more drowsiness in the evening, but may indicate that he must be alert for a test at 10 AM.

The instruction may have a relative effect in the sense that some effects may be tolerated to a certain degree only in order to comply with a given instruction. For example a patient may instruct that he must be alert for driving unless pain is above a certain given value.

Still encompassed by optional providing patient data (1901), treatment instructions may be provided at any time during a period of treatment; for example, before beginning treatment a patient may provide treatment instructions and/or treatment preferences. At any time thereafter, a patient may input additional indications and/or preferences. For example, a patient may, at any time, use a user interface associated with the device to instruct regarding a future (e.g. next) dose (or more than one dose). Such instruction may include that a dose will not be taken in a given window of time, or must be taken before a given time point, etc. Optionally such instruction may include an adjustment of the user's acceptable and/or preferred therapeutic window what constitutes a sufficient therapeutic effect and/or what constitutes a maximal level (tolerable) of an adverse effects.

Optionally, providing patient data (1901) is updated to reflect when a dose was inhaled, the dose amount and/or how the device operated in the inhalation event (e.g., if inhalation was successful or failed due to a device malfunction and/or improper usage). This may be taken as an indication of user status and/or device malfunction and/or amount of active substance inhaled (efficiency factor). Such data may be used to adjust the regiment and/or issue a notification to the user and/or medical practitioner.

Optionally, when a regimen calls for the user to administer a dose, the user may be prompted to do so, visually and/or by sound, via at least one user interface. When prompted, the user may have the option to defer by selecting a "snooze" option and optionally set the next time when he would take the next dose. In response, the device may readjust the regimen (e.g., next dose size and timing) and/or provide a notification to the user that this would not be possible or is likely to have a given adverse effect.

Optionally, if a user misses a time slot allotted for a given dose, one or more of the following may take place: (a) the regimen is adjusted to compensate for the delay; (b) a notification is given to the user (possibly by way of an alarm and/or vibration); (c) a notification is given to a care giver and/or a medical practitioner.

Generating initial dosing and/or regimen (see, 1902 in FIG. 7) may be effected as follows:

Based on recommended dosing and/or regimen (see details below) and patient data (1901), an initial dosing and/or regiment (1902) is proposed. The initial dosing and/or regimen (1902) may include the recommended dosage according to known standards and/or may be adjusted by taking into account data related to the patient's previous treatment(s) using an inhaler and the treatment instructions and/or preferences.

Taking into account the recommended dosing and/or regimen, treatment instructions may include some constraints that are more stringent than others. For example, a maximal allowed dose may not be exceeded regardless of user's preferences, and the device may be configured not to allow overdosing. Similarly, a minimal mandatory dose may be prescribed and should not be avoided regardless of user's preferences, and the device may be configured to issue a non-compliance alert to the user and/or care giver and/or medical staff in such cases. Optionally, the constraints may be imposed in advance (e.g., based on a therapeutic index of the one or more active substances and/or in accordance with a plan plotted or approved by a physician) and/or periodically or on an ongoing basis (for example as a result of specific events encountered by the user's use of the device).

Optionally, generating initial regimen (1902) is effected for a patient when first assigned with an inhaler and a regimen. In such case the patient is required to inhale the first dose or first several doses under supervision (e.g., for a period of 2 hours or more). During this time period the patient's symptoms and PD effects are observed, recorded and measured before the first dose and then occasionally at least for the supervised period. Additionally or alternatively, one or more inhalations are monitored by blood tests to extract some PK effects or a full PK profile. This may include administration of several different doses in order to establish a personalized initial dosing and/or regimen. When PK effects are taken and analyzed, a first correlation (blood concentration over time as a function of the pre-determined vaporized amount/dose) may be recorded. This correlation may remain the same for a given patient as long as no major weight change or changes in kidney and/or liver function occurs. A second correlation, such as a PD effect as a function of blood concentration over time, may be used as it is known for the population at large. Based on the two correlations an individual initial dose/PD correlation over time may be determined per patient. Optionally, a direct correlation is measured and used for a given patient, between a PD effect over time as a function off the pre-determined vaporized amount/dose.

Receiving PKPD feedback (see, 1903 in FIG. 7) is effected to include at least one of several classes of user indications/information, including user semi-controlled (voluntarily or involuntarily) indication and user uncontrolled (involuntarily) indication.

Receiving PKPD feedback (1903) may include receiving user-controlled indication and/or information, wherein the user may provide input regarding the perceived and/or sensed effect and/or a desired range of effect. For example, inputting one or more responses to interrogation via the device's user interface and/or by a practitioner (e.g., grade a degree of pain and/or a degree to a psychoactive effect), while the user has control on the input he provides. A response may include grading on a scale (e.g., a scale of pain from 1 to 10), a Yes/No response (e.g., whether nausea was removed or if food was eaten without vomiting) and/or a temporal description of an effect ("when did you notice that pain began to dissipate?", "how did the pain feel during the time from inhalation to interrogation?" etc.). The interrogation may be periodic (e.g., once a day or every several hours or upon inhalation or as a requirement before inhalation) and may be limited to only a part of the period of treatment. For example, interrogation may cover the initial 6, 12 or 24 hours in order to determine a regimen and then repeated periodically (e.g., once a day or once a week or once a month or upon desire) in order to confirm the regimen and/or readjust it in view of progress.

Receiving PKPD feedback (1903) may include receiving user semi-controlled indication, wherein the user may participate in measuring the user's status; while user compliance is needed for these indications, the user has little or no control on the result. For example, a user may be instructed to attach a sensor to his body that communicates with the device or allow sensing a property (e.g., eye redness). Optionally and alternatively, a user interface may test the user, for example by following pupils and/or instructing the user to perform a task. Examples for tasks may include, without limitation, following a mark on a screen with your eyes; dragging a mark on a screen through a pattern without touching walls; completing mental tasks (such as solving mathematical equations or answering questions); testing memory by games; and testing concentration.

Receiving PKPD feedback (1903) may include receiving user uncontrolled indication, wherein the inhaler or a device associated with the inhaler may sense one or more properties of a user as an indication of the user's status and use that as an indication of one or more effects of the inhaled dose regimen on the user. For example, sensing mouth temperature during inhalation and/or pupil size without prompting the user, each of which may indicate PD effect and thus serve as a PD effect; sensing tremor or a variation in tremor; and sensing heart rate and/or blood pressure, for example by interaction with a sensor worn by the user and/or implanted in the user.

Optionally and alternatively, sensing airflow properties in the device may be used as an indication of the user's status, wherein such air flow properties may include one or more of flow rate and/or the rate of increase in flow rate and or a degree and/or rate of variation in flow during an inhalation event. For example, considering changes from one or more baseline values, which may indicate for example an improvement or a decline in wellbeing (e.g. as manifested by strength and/or pain that may affect the inhalation properties/patterns for the user) and/or concentration or attention.

Generating adjusted regimen (see, 1904 in FIG. 7) is effected if needed, to generate an adjusted dosing and/or regimen. An adjusted dosing and/or regimen may be required when one or more of the following occurs:
1. One or more treated symptoms is not sufficiently alleviated;
2. One or more psychoactive effects exceed a given threshold
3. The therapeutic/adverse effect balance is below a given threshold; and/or
4. A change in circumstances that needs to be taken into account occurs (e.g. breakthrough pain or a missed inhalation event).

It is noted that a given activity of an agent may be regarded as a desired effect or an undesired effect inter alia in different circumstances and for different subjects. For example, an active agent that is analgesic, sedative and/or hallucinogenic it may be that the analgesic property is a therapeutic effect and the hallucinogenic property is an adverse effect. As for sedation, in some circumstances this might be a desired effect of treatment while in others it may be undesired.

Optionally and alternatively, in generating adjusted regimen (1904), the dosing and/or regimen includes a second active agent (or more than two agents) that is co-administered in order to reduce an undesired side effect of the drug.

Figure 8:
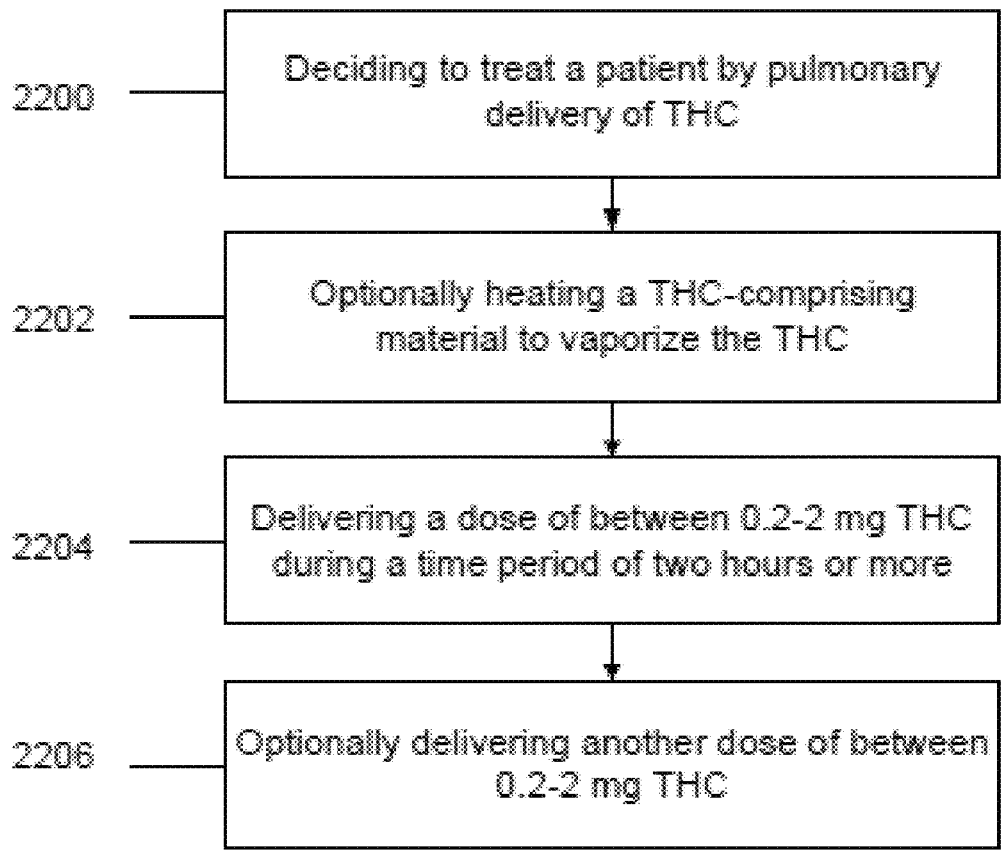
FIG. 8 is a flowchart of a method for treating a patient with a low dose of THC, according to some embodiments of the invention.

FIG. 8 is a flowchart of a method for treating a patient with a low dose of THC, according to some embodiments of the invention.

In some embodiments, a decision is made (e.g. by a physician) to treat a patient by pulmonary delivery of THC (2200).

In some embodiments, *cannabis* and/or another material comprising THC (for example synthetic THC, a THC extract, and/or a pallet of inert material comprising THC) is heated to vaporize the THC, for example using methods and/or devices as described hereinabove. (2202).

In some embodiments, *cannabis* and/or other THC-comprising material is selected to have a certain THC content, for example between 3-25% THC, between 5-50% THC, between 20-70% THC, or intermediate, higher or lower THC content. Optionally *cannabis* having at least 10% THC or at least 20% or even 25% THC is used.

In some embodiments, THC is extracted from THC-comprising material at a selected efficiency. Optionally, the efficiency is fixed for a given inhaler device. Alternatively, the device is configured to control one or more extraction parameters thereby to modify extraction efficiency. Optionally, a device such as the inhaler described hereinabove is controlled to extract THC from *cannabis* at an efficiency of, for example, at least 60%, at least 25%, at least 40%, at least 75% or intermediate, higher or lower efficiencies. In some embodiments, the amount of THC-comprising material is selected according to the extraction efficiency and/or according the THC content in the THC-comprising material, for example for a 60% extraction efficiency the selected amount of *cannabis* would include THC at about twice the amount of THC delivered to the patient. In an example, for extracting a 2 mg THC dose, an amount of *cannabis* comprising about 3.33 mg needs to be heated. In some embodiments, the amount of THC-comprising material is such that it contains THC at an amount that is no more than twofold a maximal amount of THC that is to be delivered to the user from the material or no more than 1.5 times the maximal amount of THC that is to be delivered.

In some embodiments, a dose of between 0.2-2 mg THC is provided to the patient (2204). Optionally, the low dose is delivered within any time period of two hours or more. In some embodiments, the low dose is delivered in a single delivery event. Alternatively, the low dose is delivered over a plurality of delivery events.

In some embodiments, a "single delivery event" refers to an event over which a single low dose is delivered to the patient through inhalation. In some embodiments, a single delivery event refers to one activation of an inhaler device over which the dose is delivered to the patient, comprising, for example, heating of sufficient material to extract the dose and allowing flow of the vaporized THC to the patient. A "single delivery event" may include one inhalation of the patient. Alternatively, a single delivery event may include a plurality of inhalations performed within a time period short enough so as to be considered as a single event. Optionally, each delivery event is coupled with an activation of heating, which is reduced or terminated between delivery events. Optionally, each delivery event includes extracting THC from a separate cartridge or a separate THC-comprising material source.

Optionally, a single delivery event includes only one inhalation, and optionally a single inhalation is shorter than 3 seconds. Since inhalation may vary between patients depending on, for example, a depth of inhalation, puff duration, breath hold time, volume intake and/or other parameters, a single delivery event is generally referred to herein as an event in which a pre-determined dose of THC is delivered to the patient through inhalation, according to some embodiments.

In some embodiments, a single dose is delivered in a single delivery event. Optionally, the single dose is provided from a plurality of sources of THC-comprising material(s). In an example, the single dose is provided by heating a plurality of cartridges, simultaneously and/or in sequence.

In some embodiments the period of time between an inhalation of a first dose portion and an inhalation of a second dose portion is sufficiently short to be regarded as a single delivery event. Optionally, a number of inhalations takes place within 5-30 minutes or within under 15 minutes or even within under 5-10 minutes. Optionally, each inhalation in such "rapid succession" delivers to the user a different amount or a composition. Optionally, two or more of the inhalations provide the same composition and amount. In some embodiments, an inhalation of a second dose portion is performed at such timing that a first dose portion inhaled previously still induces at least one PD effect in the subject. In some embodiments, delivery in rapid succession means that the inhaled dose portions have essentially the same effect as they would have had if inhaled in a single delivery event.

In some embodiments, control over the amount of THC delivered is provided by programming a controller of an inhaler device (for example, but not limited to, an inhaler as described hereinabove) to limit the amount of THC to 2 mg or less by one or more of: controlling heating parameters (e.g. duration, temperature, rate, heating pattern), controlling the amount of *cannabis* and/or other THC-comprising material being heated, regulating airflow (e.g. to the user and/or through the THC comprising material) and/or combinations thereof. Additionally or alternatively, control of the amount of THC delivered is provided by heating a cartridge which is pre-packed with an amount of *cannabis* and/or other THC-comprising material from which 2 mg THC or less can be extracted.

In some embodiments, the cartridge comprises *cannabis* comprising THC at an amount equal to or smaller than two fold or 1.5 fold the amount of THC to be delivered.

Optionally, the cartridge comprises *cannabis* at an amount including no more than 6 mg THC, no more than 8 mg THC, no more than 4 mg THC, no more than 1 mg THC, or intermediate, larger or smaller amounts. Optionally, a single dose cartridge is used to provide THC for more than a single delivery event and/or more than a single inhalation.

In some embodiments, after the low dose is delivered to the patient via one delivery event, THC is not provided again for at least 2 hours. Optionally, the two hour period begins immediately after the last inhalation of the delivery event. Optionally, THC is not provided for at least 3 hours, at least 5 hours, at least 7 hours, or intermediate, longer or shorter time periods. In some embodiments, no more than between 0.2 mg to 2 mg THC is delivered within a two hour time period, optionally at a single delivery event. Optionally, the amount is between 0.1 and 0.75 mg within a two hour time period or between 0.1 mg and 0.5 mg within a two hour time period.

In some embodiments, the next dose, delivered after at least two hours, comprises 2 mg or less THC (2206), or 1 mg or less or 0.5 mg or less.

In some embodiments, no more than 8 delivery events, 6 delivery events, 4 delivery events or intermediate, or lower number of delivery events are provided over a day, wherein in each event 2 mg THC or less are delivered to the patient.

In some embodiments, a total of no more than 10 mg THC, no more than 7.5 mg THC, no more than 6 mg THC, no more than 4 mg THC, no more than 2 mg THC, no more than 1 mg THC or intermediate or smaller amount of THC is delivered over a day. In some embodiments, between 0.5-1 mg THC is delivered 3 or 4 times a day. A time period of a "day" as described herein may refer to waking hours, for example a time period of 10 hours, 11 hours, 12 hours, 14 hours. Alternatively, a "day" as referred to herein may include night hours as well, therefore a time period of 24 hours.

In some embodiments, the amount of THC delivered at a single dose and/or at a plurality of doses and/or over a day is adjusted according to one or more personal parameters such as age, weight, THC sensitivity, severity of symptoms, concurrent medication, personal preferences and/or tolerances. In an example, an inexperienced user may prefer a 0.5 mg dose rather than, for example, a 2 mg dose, since the 0.5 mg dose would have a reduced psychoactive effect on the user than the higher dose. In another example, a child might be prescribed with very low doses, for example between 0.2 mg and 0.5 or 1 mg, while optionally taking into account other parameters relating to the child.

In some embodiments, the actual amount of THC delivered (selected for example from the range of 0.2 mg to 2 mg) is set by the physician and/or by the user, and may vary throughout the day. In an example, the user may decide to inhale smaller amounts (e.g. 0.1 mg, 0.2 mg, 0.5 mg, 0.7 mg) during the day, so that the psychoactive effect will be relatively low and will interfere less with daily activities (e.g. driving), and inhale larger amount(s) (e.g. 1.5 mg, 2 mg) in the evening. Optionally, a physician may set a maximum dosage while a user will have the freedom to inhale less than the prescribed amount, optionally according to his symptom (e.g pain) intensity at that moment and/or according to his need for clarity or aversion to a psychoactive effect.

In some embodiments, THC is delivered concomitantly and/or sequentially with one or more other drugs, including for example one or more cannabinoids. In an example, an inhaler device for example as described herein is configured to deliver a 0.2-2 mg dose of THC, and to deliver one or more other active substances before, during and/or after delivery of the THC.

It has been shown by inventors in experiments performed that an inhaled THC dose of 0.2-2 mg may provide sufficient symptom alleviation for a time period of at least 2 hours, at least 3 hours, at least 4 hours, at least 6 hours or intermediate or longer time periods. In some cases, symptoms such as pain and/or nausea were reduced, for example reduced by 30%, 50%, 70% or intermediate, higher or lower percentages without return of the symptom to a pre-inhalation degree for a time period of at least 2 hours. Other examples of symptoms which may be alleviated by prescribing a low dose regimen may include adverse effects of chemotherapy and/or vomiting and/or weight loss and/or insomnia and/or euphoria and/or drowsiness and/or psychomotor effects and/or cognitive effects, and/or agitation and/or depression.

Cancer patients suffering from advanced symptoms and/or side effects of chemotherapy were treated in accordance with the above described regimen, being delivered a dose of between 0.2-2 mg THC at a single delivery event and waiting at least two hours before the next dose. The patients voluntarily reported their conditions.

In a first case, a 28 year old female cancer patient was admitted to hospital for chemotherapy. She was previously prescribed *cannabis* for pain, vomiting, nausea and weight loss, which she took by smoking cigarettes. Unfortunately, the cigarettes did not alleviate her symptoms sufficiently. In the experiment, the patient was prescribed 3×0.5 mg THC per day, delivered using an inhaler device for example as described hereinabove. The first dose was to be taken 30 minutes before chemotherapy. The patient was allowed to take additional inhalations as needed. In the day of the experiment, after receiving chemotherapy as planned, the patient was eating, was free of nausea and vomiting and had significantly improved mood. The patient inhaled the 3 prescribed doses only, and no other medication was prescribed or taken. Later, the same patient readmitted to hospital for an additional round of chemotherapy. This time she chose to inhale THC in four 0.5 mg doses, a first dose in the morning before chemotherapy, second and third doses taken concomitantly at midday (amounting to a single 1 mg dose) and a fourth dose in the evening. Again, the treatment was shown to be effective.

In a second case, a 50 year old male cancer patient was admitted to the hospital for severe pain and in order to resume treatment that he chose to terminate earlier. He was previously prescribed *cannabis* for pain, cachexia and nausea, in addition to other drugs. Throughout the treatment, he received a continuous morphine drip (400-600 mg) with additional morphine treatment upon need. Before being hospitalized, he had not eaten for a week, suffered from sleep deprivation and was depressed. In the hospital he was provided with an inhaler for example as described hereinabove and during the first day of use he inhaled 0.5 mg THC doses 18 times a day, which included 4 previously prescribed doses of 0.5 mg and many demands for additional pain relief. On the next day he reduced the intake to 1 mg inhalations, 4 times a day, continuing for a period of 8 days. Throughout the treatment, and even on the first day, the patient ate 3 meals per day and exhibited significant mood improvement.

Figure 9:
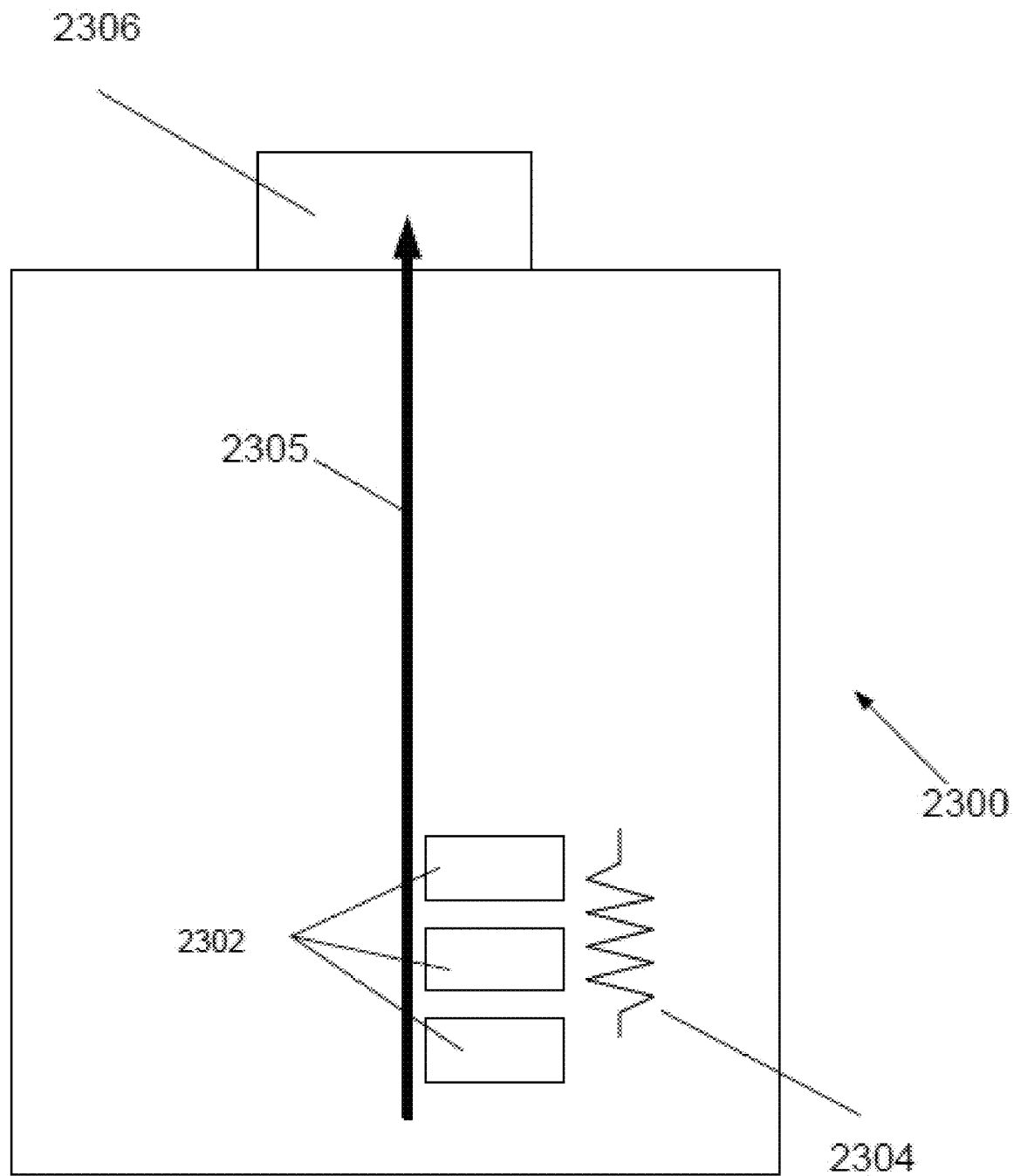
FIG. 9 schematically illustrates an inhaler device configured to deliver one or more doses comprising no more than 2 mg THC each, according to some embodiments of the invention.

FIG. 9 schematically illustrates an inhaler device 2300 configured to deliver one or more doses comprising no more than 2 mg THC each, according to some embodiments of the invention.

In some embodiments, the device comprises one or more cartridges 2302 comprising THC-comprising material.

In some embodiments, the device comprises a heating mechanism 2304 configured to heat the THC-comprising material to vaporize THC. In some embodiments, the extracted THC vapors are delivered to the user via an airflow path 2305 and through mouthpiece 2306.

In some embodiments, the amount of material in a single cartridge 2302 is selected so that the amount of THC extracted from the cartridge and delivered to the user comprises no more 2 mg THC, optionally between 0.2-0.5 mg THC, between 0.3-1.5 mg THC, between 0.5-1.5 mg THC or intermediate, larger or smaller amounts.

In some embodiments, the amount of *cannabis* and/or other THC-comprising material is selected according to the extraction efficiency. In an example of a 60% extraction efficiency, a cartridge may include *cannabis* at an amount of material comprising THC at about two fold the amount of THC that is to be delivered to the user. For example to deliver a 2 mg THC dose to the user, a cartridge comprising about 3.33 mg THC is heated. In some embodiments, the amount of material in each cartridge is selected in accordance with the THC content of the material.

In some embodiments, the amount of THC-comprising material is chosen according to the potency, concentration, and/or volatility of the vaporizing fraction. When *cannabis* granulate is used, for example, the measured amount is optionally 15 mg, or another value in the range of 10-20 mg. Choice of amount optionally depends, for example, on plant variety, growing conditions, and/or assay results of a botanical substance available for packaging. In some embodiments, the measured amount is within the range, for example, of 1-20 mg, 10-40 mg, 25-75 mg, 50-100 mg, or within another range of amounts having the same, intermediate, larger, or smaller bounds. In some embodiments, for example, if the required dosage is too small to fill the substance receiving chamber, a filler substance is optionally added; for example, a portion of an inert (lacking volatile drug activity) botanical substance.

Optionally, the filler is uniformly mixed with the required dosage."

In some embodiments, the device comprises a single cartridge with material sufficient for a single dose of between 0.2-2 mg THC. Alternatively, the device comprises a plurality of cartridges, each comprising material sufficient for a single dose. Optionally, the number of cartridges is sufficient for use over a day. Alternatively, the number of cartridges is sufficient for use over a week. Alternatively, the number of cartridges is sufficient for use over a month and/or other time periods.

Alternatively, each cartridge comprises material sufficient for more than one dose, for example comprising material sufficient for 2 doses, 4 doses, 8 doses or intermediate, larger or smaller number of doses. Optionally, each cartridge comprises less than a single dose and the device is configured to deliver a given dose using a plurality of cartridges via one or more inhalation events.

In an embodiment, the device is configured to re-heat a cartridge comprising a single dose, allowing a user to take the dose in multiple delivery events instead of a single delivery event, until all THC is extracted. Optionally, the device comprises only a single such cartridge.

In some embodiments, the device is pre-packed with THC-comprising material having a total of no more than 4 mg THC (for example for a single delivery event), no more than 15 mg THC (for example for daily use), no more than 105 mg THC (for example for weekly use) and/or intermediate, larger or smaller total amounts of THC.

In some embodiments, a cartridge 2302 comprises one or more active substances other than THC (for example one or more cannabinoids and/or other substances as listed hereinabove). Optionally, a cartridge does not comprise THC and comprises one or more active substances. In some embodiments, device 2300 is configured to deliver the one or more active substances concomitantly and/or sequentially with THC, for example during a single delivery event.

In some embodiments, a magazine comprising a plurality of cartridges is provided, wherein a total amount of THC within each cartridge is no more than 4 mg, no more than 3 mg, no more than 6 mg, no more than 1 mg, no more than 8 mg or intermediate, larger or smaller amounts. Optionally, each of the plurality of cartridges contains the same amount of THC. Alternatively, some of the cartridges comprise different amounts of THC than others.

In some embodiments, a cartridge may include a drug combination (for example material having a certain THC: CBD ratio). Optionally, different cartridges of a magazine comprise different drug combinations, and the device is configured to select a cartridge for use according to its content and a prescribed dosing regimen.

Structural and/or operational aspects of the inhaler device may be as described in one or more of the various embodiments detailed hereinabove.

Figure 10:
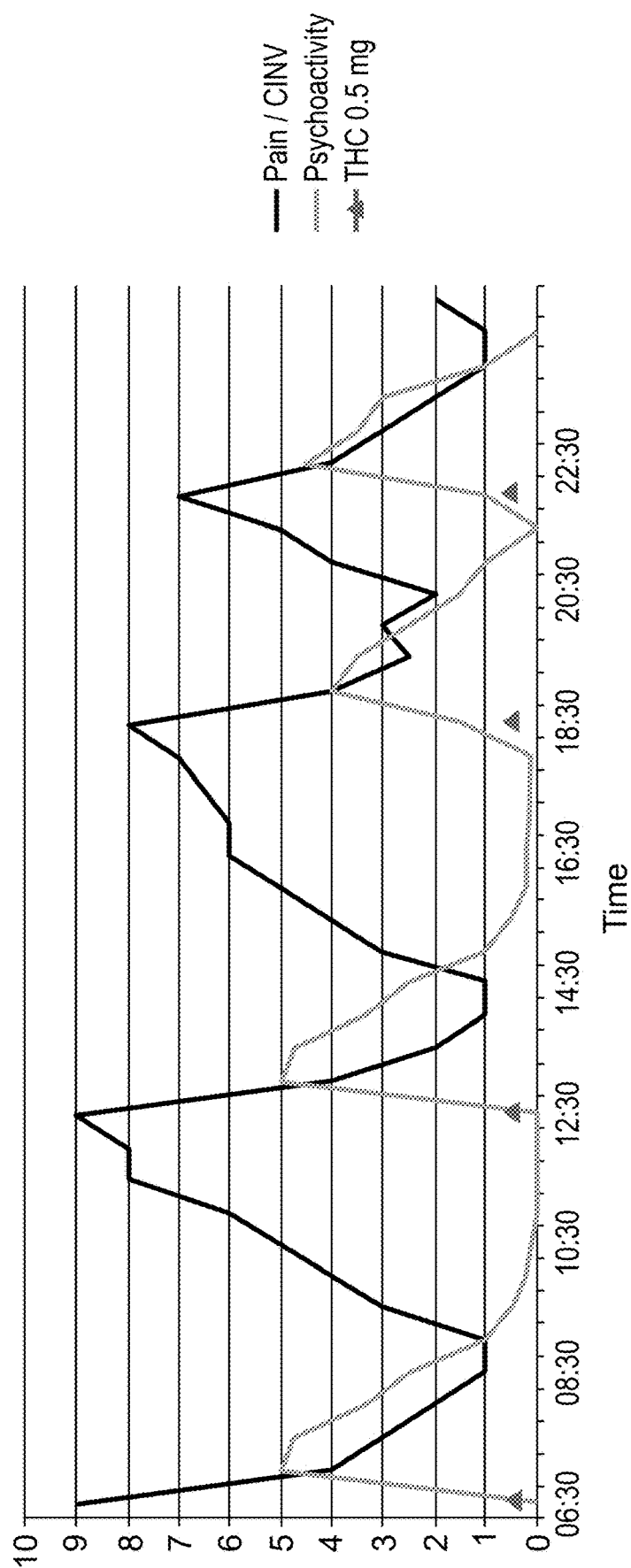
FIG. 10 is a graphical representation of a regimen for the treatment of pain by pulmonary delivery of 0.5 mg THC doses provided in time intervals of at least two hours, according to some embodiments of the invention.

FIG. 10 is a graphical representation of a regimen for the treatment of pain by pulmonary delivery of 0.5 mg THC doses delivered in time intervals of at least two hours, according to some embodiments of the invention.

In this use over a time period of 16 hours, 4 doses of 0.5 mg THC each were provided at time intervals of at least two hours between sequential doses, indicated by the grey triangles. The black line represents the symptom level, in this case pain, and the grey line represents psychoactive effects.

The x-axis represents the time of day, and the y-axis represents an arbitrary scale for indicating symptom severity and level of psychoactivity. The scale represents, based on user reports, a grade of the symptoms and a grade of the psychoactive effects, for example compared to a baseline report collected from the patient before treatment.

As can be seen in the figure, the first dose delivered at 6:30 is effective to dramatically reduce the pain level. A rise in psychoactivity occurs. In the 4 hours that follow the first dose, in which no additional doses or other medication are provided, the psychoactivity level decreases. The pain level begins to rise again at about 2 hours after the dose was delivered.

At 12:30, another dose is inhaled, leading to a rise in psychoactivity and a descent in the pain level. About two hours later the pain level rises again, and another dose is given at 18:30, reducing the pain level and causing a rise in psychoactivity. The last dose is delivered four hours later, at 22:30.

Optionally, before bedtime the maximal dose is increased (e.g. from 0.5 mg to 1 mg; optionally as two or more consecutive inhalations) to allow a longer period of reduced pain intensity.

Figure 11:
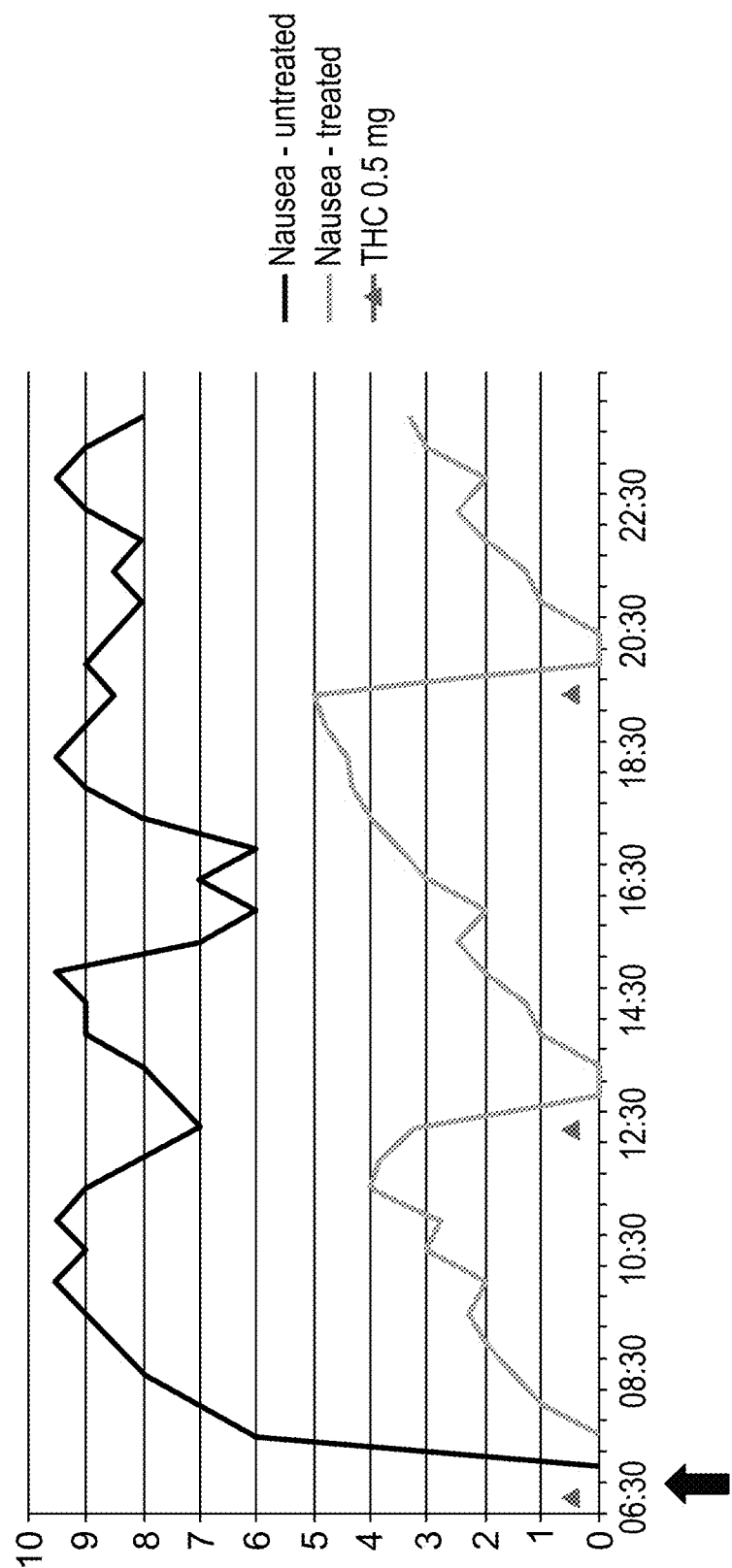
FIG. 11 is a graphical representation of a treatment effect achieved by pulmonary delivery of 0.5 mg THC doses, provided at time intervals of at least two hours, according to some embodiments of the invention.

FIG. 11 is a graphical representation of the treatment effect achieved by pulmonary delivery of 0.5 mg THC doses, delivered at time intervals of at least two hours, according to some embodiments of the invention.

In this example, nausea levels of a patient undergoing chemotherapy are shown, as indicated by the arbitrary Y-axis scale. The black line depicts a typical nausea effect that is often witnessed when no special anti-nausea treatment is provided (optionally other than the conventional prophylactic treatment provided normally intravenously in chemotherapy sessions).

Chemotherapy commenced at 7:00 AM, as indicated by the black arrow. As seen, shortly after chemotherapy begins, nausea reaches a high level. It may remain high when not treated or even with conventional treatment, although the degree of nausea may fluctuate.

The gray line depicts nausea levels under treatment with 0.5 mg doses of THC, delivered in intervals of at least two hours, indicated by the grey triangles. The first dose was given 30 minutes before chemotherapy started, causing a significant delay in the onset of nausea and a significant reduction in the maximum level reached. Two additional doses of 0.5 mg THC each, delivered at 12:30 and at 19:00, sufficed to allow the patient to combat the nausea throughout the day.

It is known that a patient may suffer from nausea even before chemotherapy begins, for example due to anticipation of the side effect and/or because of earlier treatment (since nausea may last days or even weeks post a chemotherapy treatment session). In accordance with the above example, in some embodiments, such as when treating a chemotherapy patient, delivering a first dose of between 0.2-2 mg THC before chemotherapy begins (such as 30 minutes before, 10 minutes before, 45 minutes before or intermediate, longer or shorter time periods) may be advantageous. Optionally, the first dose is delivered as soon as the patient is diagnosed with a need for chemotherapy, optionally followed up with a regimen of 3-4 daily doses of 0.2-2 mg THC at least up to the beginning of chemotherapy, when the regimen may be adjusted.

Figure 12:
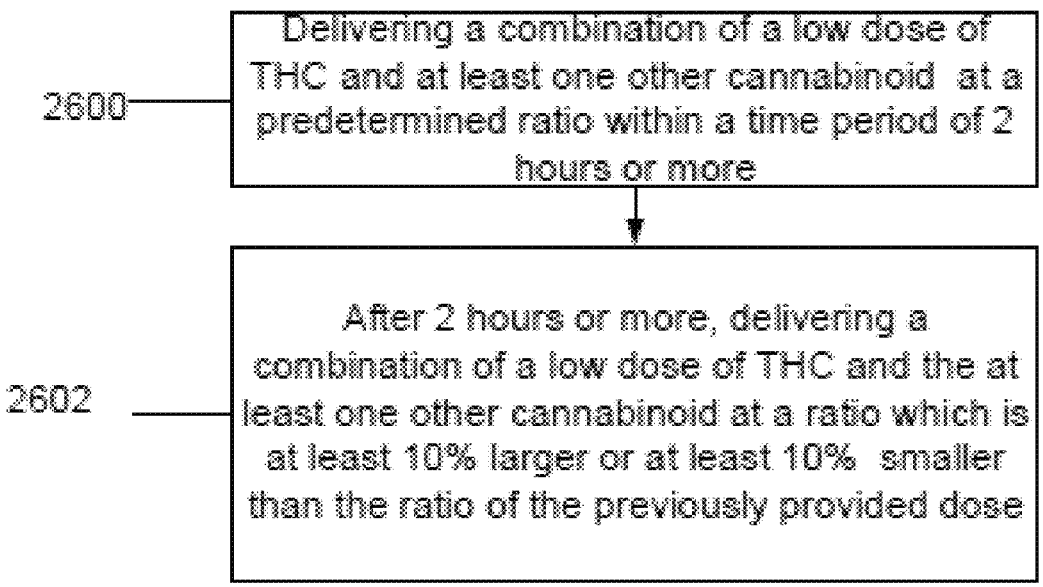
FIG. 12 is a flowchart of a method for treating a patient with a combination of THC and at least one other cannabinoid at a predetermined ratio, according to some embodiments of the invention.

FIG. 12 is a flowchart of a method for treating a patient with a combination of THC and one or more other drugs, for example at least one other cannabinoid at a predetermined ratio, according to some embodiments of the invention.

Optionally, the method is carried out by an inhaler device that is configured to control the dosing regimen in accordance with the method, for example as described hereinabove.

In some embodiments, a combination of two or more active substances, such as THC and at least one other cannabinoid, for example CBD are delivered. In some cases, it may be preferable to inhale different ratios of the active substances at different times. For example, when inhaling an active substance such as THC from *cannabis*, there is an entourage effect wherein many different compounds are inhaled simultaneously and thus yield a combined effect. In some embodiments, by selecting a specific active substance combination and/or ratios, a regimen may be selected to reduce the amount of one or more of the active substances' intake (in any inhalation and/or in total during a period of time) and/or improve treatment results (e.g. by increasing a desired effect and/or decreasing an undesired one).

In an example, CBD, a non-psychoactive cannabinoid, known for enhancing the therapeutic effects of THC is achieved in combination with THC. CBD has been shown to counteract psychotic symptoms and cognitive impairment associated with *cannabis* use as well as with THC administration. Medicinally, CBD has antipsychotic properties and has been shown to relieve anxiety, pain, muscle spasms, inflammation nausea, vomiting, convulsions and to decrease the risk for developing schizophrenia. A potential advantage of using a combination of THC and CBD may include achieving extended symptom relief with reduced psycho activity. In nature, THC and CBD are both prevalent in *cannabis* and are normally inhaled simultaneously during *cannabis* usage. However, many plants already exist having different cannabinoid ratios, and in addition essentially any combination may be produced by mixing plants and/or adding or using separately extracted, purified and/or synthetic compounds.

In some embodiments, a combination of THC and at least one other cannabinoid such as CBD and/or $\Delta^9$-tetrahydrocannabivarin (THCV) and/or any other cannabinoid that is antagonist or reverse agonist to receptor $CB_1$ extracted from plant material or provided as a solid/synthetic form (such as Marinol/Nabilone and CBD) comprising a predetermined THC:CBD ratio is delivered (2600). In some embodiments, the amount of THC per dose is between 0.2-2 mg. In some embodiments, the combination is extracted from a specific strain of *cannabis* having a predetermined THC:CBD ratio, for example taking into account also the effect of growing conditions. Additionally or alternatively, a plurality of *cannabis* strains are mixed together. Additionally or alternatively, one or more active compounds are added to *cannabis*. Additionally or alternatively, a selection of two or more drugs are mixed together. In some embodiments, different drug sources are used.

Optionally, an inhaler device for example as described herein comprises a plurality of cartridges, each including a different drug. Alternatively, a cartridge may include mixed drugs. Optionally, a device may have a plurality of cartridges, each having a different drug composition, ranging potentially from a single drug per some cartridge to any combination or ratio of two or more drugs in other cartridges.

In some embodiments, the device is configured to automatically select a ratio of active substances delivered. Optionally, the selection is made based on input received by the device, for example based on feedback from the patient and/or based on a scheduled regimen received by the device. Selection of a ratio may be carried out by one or more of: a controller, a decision module, and/or memory components.

Examples of commercially available strains varying in their THC:CBD contents include:

Bedrocan® is considered a *sativa* type *cannabis* strain. Its THC-level is standardized at 22%, with a CBD-level below 1%.

Bedrobinol® is also considered a *sativa*. Its THC-level can be considered medium strength, standardized at 13.5%, with a CBD-level below 1%.

Bediol® has a lower to medium THC-level, standardized at 6.5%, and a medium level of the non-psycho-active Cannabidiol (CBD), standardized at 8%. Bediol is also a *sativa* type.

Bedica® is considered an indica variety. It also has medium amounts of THC, around 14%, with less than 1% CBD.

Bedrolite® is a non-psychoactive strain that contains approximately 9% CBD and 0.4% THC.

In some embodiments, the following dose is delivered after at least two hours have passed from inhalation of the first dose (2602). Optionally, at least 3 hours, at least 4 hours, at least 6 hours or intermediate, longer or shorter time periods pass before the next dose is provided. In some embodiments, the next dose provided comprises a different THC:CBD ratio (2602). Optionally, the THC:CBD ratio of the following dose is larger than the THC:CBD ratio of the first dose, for example being at least 10% larger, at least 25% larger, at least 75% larger or intermediate, higher or lower percentages larger. Alternatively, the THC:CBD ratio is smaller than the THC:CBD ratio of the first dose, for example being at least 10% smaller, at least 25% smaller, at least 75% smaller or intermediate, higher or lower percentages smaller.

In some embodiments, the ratio includes a cannabinoid that is undetectable, for example having a very low amount.

In some embodiments, two or more consecutive doses are delivered 15-30 minutes of each other, until either the maximum allowed low dose of at least one of the active substances is reached (e.g. 0.2-2 mg THC) or until the user feels sufficient symptom relief and/or until reaching a maximal tolerated side effect. In some embodiments, the following dose is delivered after at least a period of time proportionate to the amount delivered (e.g. at least 4 hours for a total of 1 mg THC) passed from inhalation of the consecutive doses. Optionally, at least 6 hours, at least 8 hours, at least 10 hours or intermediate, longer or shorter time periods pass before the next dose is delivered.

A daily treatment regimen in which combined THC and CBD doses are provided may include: providing morning and evening doses from a *cannabis* strain having a relatively large THC:CBD ratio, while inhalations during the day may be provided from *cannabis* stain having a smaller THC:CBD ratio. Referring to the above mentioned *cannabis* strains, it may be beneficial for the patient to inhale the relatively high THC Bedrocan® in the morning, with two doses of Bediol® during the day and then in the evening again Bedrocan®. Thus, the patient may feel drowsy and calm before going to bed and also the relatively strong effect of THC in the morning after a long night without treatment, while during the day, more clarity and less psychotomimetic effects may be preferred, and THC may thus be better augmented with a higher ratio of CBD. Optionally, when THC:CBD ratio is relatively small, a lower dose of THC may suffice as compared to a high ratio THC:CBD strain or drug combination.

Figure 13:
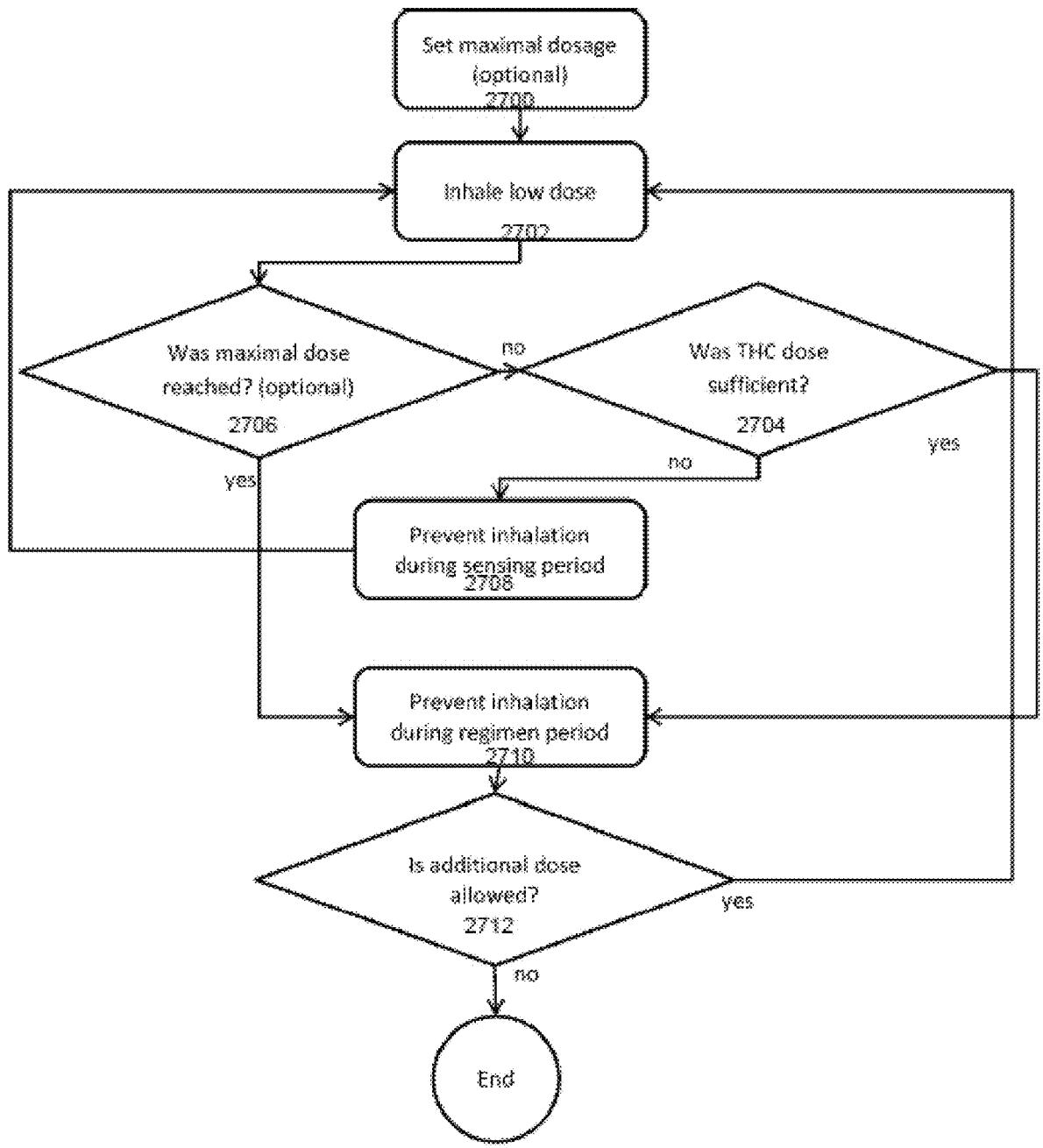
FIG. 13 is a flowchart of a method for delivering one or more low doses of THC, according to some embodiments of the invention.

FIG. 13 is a flowchart of a method for delivering one or more low doses of THC, according to some embodiments of the invention.

In some embodiments, a maximal dosage is set 2700. Optionally, the maximal dosage is set per a predetermined regimen period, for example 2 mg THC in a two hour interval; 3 mg in a four hour time interval; 6 mg THC in a day; 0.5 mg in an hour and/or other maximal dosage within any predetermined regimen period.

Once a first low dose is delivered (2702), if the maximal dosage was reached, additional delivery is prevented for the predetermined regimen period (2710). If the maximal dosage was not reached, but the first delivered dose was sufficient (for example sufficient to alleviate one or more symptoms of the user such as pain, nausea and/or other symptoms), additional delivery is prevented for the predetermined regimen period (2710). Alternatively, if the first delivered was not sufficient, additional delivery is prevented for a sensing period (2708). Optionally, the sensing period includes a time period sufficient for one or more effects of the inhaled THC to take place, for example between 5-30 minutes, between 10-50 minutes, between 1-15 minutes, between 10-25 minutes, or intermediate, longer or shorter time periods. Optionally, the effects include reducing a level of a symptom, for example as sensed and reported by the user, by at least 20%, at least 50%, at least 70% or intermediate, higher or lower percentages.

Optionally, at the end of sensing period, another delivery may take place (2702).

In some embodiments, at the end of the regimen period, additional delivery may take place, if allowed (2712) (for example if the user did not exceed a daily maximal dose and/or other maximal set dose).

Figure 14:
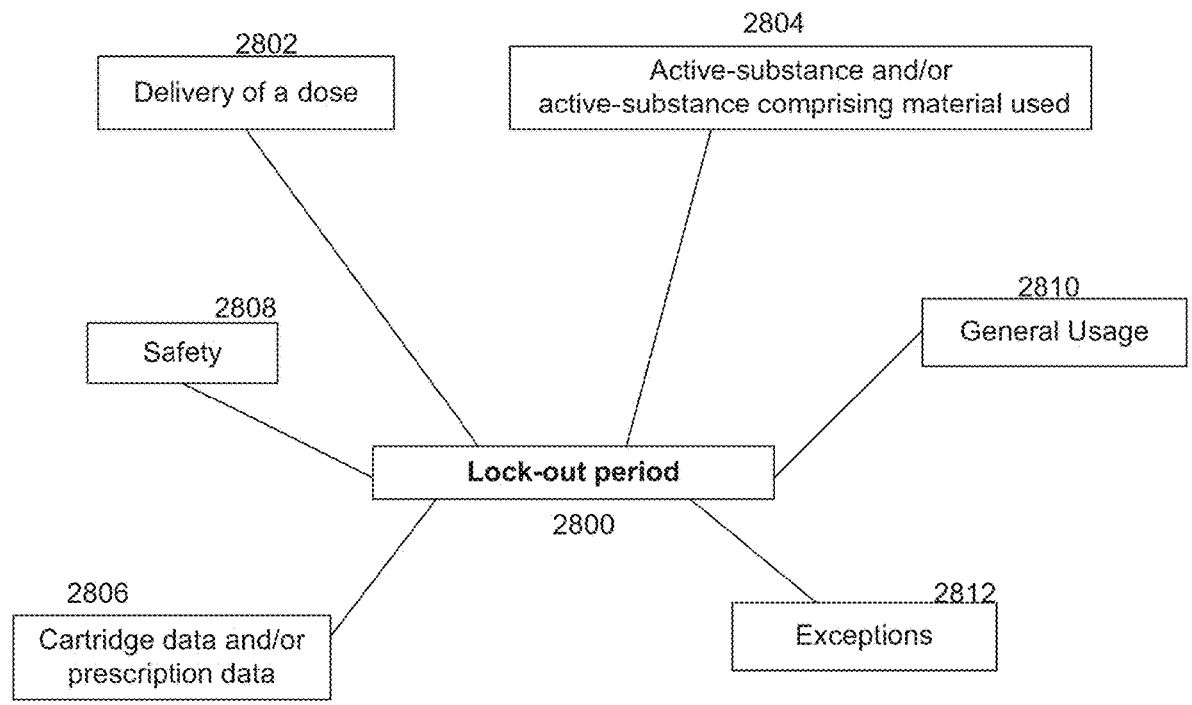
FIG. 14 is a schematic diagram of factors associated with setting of a lock-out time period of an inhaler device, according to some embodiments of the invention.

FIG. 14 schematically describes various factors affecting a timing and/or duration of a lock-out period 2800 set in an inhaler device, according to some embodiments.

In some embodiments, the inhaler device is configured to lock for a time period throughout which additional delivery is prevented. The "lock-out" time period may extend for example between 1.5 hours and 12 hours, or between 2 and 6 hours, or between 2 and 4 hours, such as 2.5 hours, 5 hours, 7 hours, 10 hours or intermediate, longer or shorter time periods.

In some embodiments, the lock out time period is set according to delivery of a dose to the patient (2802). The "lock-out" time period may range between, for example, 2 hours from delivery of a first dose, 3 hours from delivery of a dose (e.g. a first dose), 7 hours from delivery of a dose, 10 hours from delivery of a dose or intermediate, longer or shorter time periods.

In some embodiments, the lock-out time period is set according to the active substance composition provided and/or according to the active-substance comprising material used (2804). For example, the lock out period is set according to the amount of active substance delivered. In another example, the lock-out time period is set according to at least one property of the source material used, including for example one or more of: the type of source material used, a *cannabis* strain from which the THC and/or other active substances are extracted, the THC content of the source material, the composition of active substances provided along with THC from the source material, and any medical instruction relating for example to other active substances used by the patient. In another example, the lock-out time period is set according to a ratio of cannabinoids provided and/or according to the order in which different cannabinoids are provided.

In some embodiments, the source material is provided in a cartridge and the lock-out time period is set according to cartridge data (e.g. data pertaining to the source material) and/or prescription data (2806). Optionally, the device controller is configured to control timing of delivery and/or lock-out periods according to data automatically read from the cartridge and/or data received or sensed as input.

In some embodiments, the device is locked as a safety measure (2808). Optionally, the device is locked to prevent or reduce the hazard of overdosing. Additionally or alternatively, the device is locked to prevent or reduce the hazard of unauthorized use, for example by a non-patient. A potential advantage of a device configured for locking for predetermined or selected periods of time may include ensuring or improving the probability of safe use for patients that are at a higher risk for misuse, for example children, elderly, mentally impaired patients and the like.

In some embodiments, a timing of locking and/or a duration of a lock-out period are associated with general usage (2810). In some embodiments the controller is programmed to set heating of one or more cartridges at predetermined times, optionally regardless of whether inhalation took place. Optionally, a notification is provided before and/or during heating.

In some embodiments, the device is programmed with different time schedules of delivery and lock-out, for example a first schedule for weekdays and a second schedule for weekends or holidays; a first schedule for daily use and a second schedule for night use, and others. Optionally, the device automatically switches between different schedules. Additionally or alternatively, switching is performed by manual control.

In some embodiments, the device is configured for automatically selecting a cartridge for use according to a predefined lock-out period. For example, a lock-out period can be defined for night hours and the controller will automatically select a cartridge comprising a suitable source material (e.g. a certain *cannabis* strain), a certain composition of active substances etc. according to the lock out period that was set.

In some embodiments, in exceptional and/or emergency situations (2812), the device is configured to allow limited delivery even during a lock-out period. Examples of exceptional and/or emergency situations may include: breakthrough pain or other increase in a treated symptom (e.g. nausea) and/or an indication that a symptom to be treated or prevented is sensed by the patient (e.g. an aura indicating the onset of a migraine), and/or occasional insufficiency of a provided amount of THC (due for example to some circumstance of the user or to malfunction of the device or a defect of the cartridge) and/or before or after a scheduled event which may require enhanced effect (e.g. pre-operation, chemotherapy, etc.) Optionally, exceptional delivery is remotely authorized, for example by a physician. In an example, a control center and/or a physician remotely instruct lock release. Additionally or alternatively, the device is programmed with predefined limitations for usage that is not according to the regimen, for example allowing no more than one additional maximal dose every 12 hours or the like.

Figure 15:
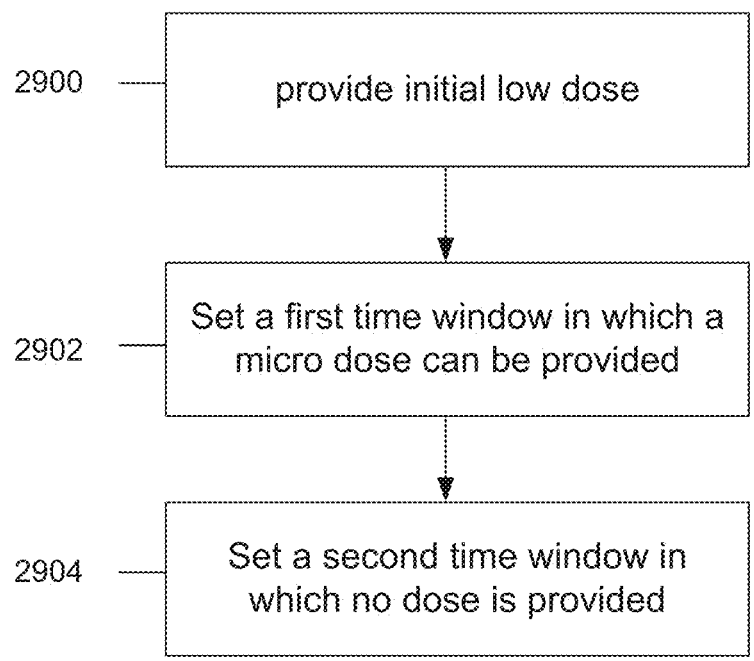
FIG. 15 is a flowchart of a delivery scheme of at least one active substance via an inhaler device, according to some embodiments of the invention.

FIG. 15 is a flowchart of a delivery scheme of at least one active substance via an inhaler device, according to some embodiments.

In some embodiments, an initial low dose is provided to the patient (2900). Optionally, the initial dose includes THC at an amount of 0.1 mg, 0.5 mg, 0.6 mg, 0.75 mg, 1 mg, 1.5 mg, 2 mg or intermediate, larger or smaller amounts.

In some embodiments, the initial low dose is determined according to previous treatment provided to the patient and whether the patient has previously experienced the effects of the provided active substance. Optionally, the initial low dose is set based on the patient's tolerability levels. For example, in the case of an experienced patient, an initial low dose of 0.5 mg is set, while for a non-experienced patient an initial low dose of 0.1 mg may suffice.

In some embodiments, the device receives input from the patient whether the initial low dose was sufficient. Additionally or alternatively, the device (i.e. the controller) decides whether the initial low dose was sufficient, for example by referring to recorded usage data and/or feedback acquired from the patient).

In some embodiments, following delivery of the initial low dose, the device allows for a first time window in which another micro dose can be provided (2902). Optionally, the first time window is set for up to 10 minutes following delivery of the initial dose, up to 30 minutes, up to 1 hour, up to 2 hours or intermediate, shorter or longer time periods following delivery of the initial dose. Optionally, the micro dose includes an amount of active smaller than the initial dose that was provided, for example including 0.05 mg, 0.1 mg, 0.15 mg, 0.2 mg of THC or intermediate, smaller or larger amounts of THC.

In some embodiments, during the first time window, a maximal amount of active substance is set and the device limits delivery of amounts larger than the maximal set amount. The maximal amount may be defined as the additional amount delivered during the first time window, or, alternatively, as the total amount delivered (i.e. including the initial dose and the additional micro dose delivered during the first time window).

In some embodiments, a second time window is set throughout which no dose is provided (2904). In some embodiments, during the second time window, the device locks and prohibits use. Alternatively, a placebo drug may be provided during a lock-out time period.

In some embodiments, the second time window is set according to the time in which the initial dose was delivered, for example preventing delivery for at least two hours, at least 5 hours, at least 10 hours or intermediate, longer or shorter time periods from the delivery of the initial dose. Alternatively, the second time window is set according to a time in which the dose was augmented by delivery of the micro dose.

In some embodiments, during the first time window, the patient is allowed to take a plurality of doses (up to a maximal amount allowed amount) until a symptom is sufficiently alleviated. Optionally, a duration of the second time window is longer than the first time window, yet is short enough to prevent the patient from returning to their pre-treatment condition.

In some embodiments, the device controller determines whether or not to enable delivery by referring to previous deliveries made within the last hours or days, for example previous deliveries made in the last two hours, the last 5 hours, the last 10 hours or intermediate, longer or shorter time periods. Optionally, the decision is made upon an attempt of the patient to inhale and/or by the patient turning the device on and/or any other patient instruction received by the device, indicating that the patient is interested in taking another dose. In some embodiments, the controller sets an amount to be delivered by taking into account previous amounts provided within a defined time period from a time point in which the patient attempts use.

Figure 16:
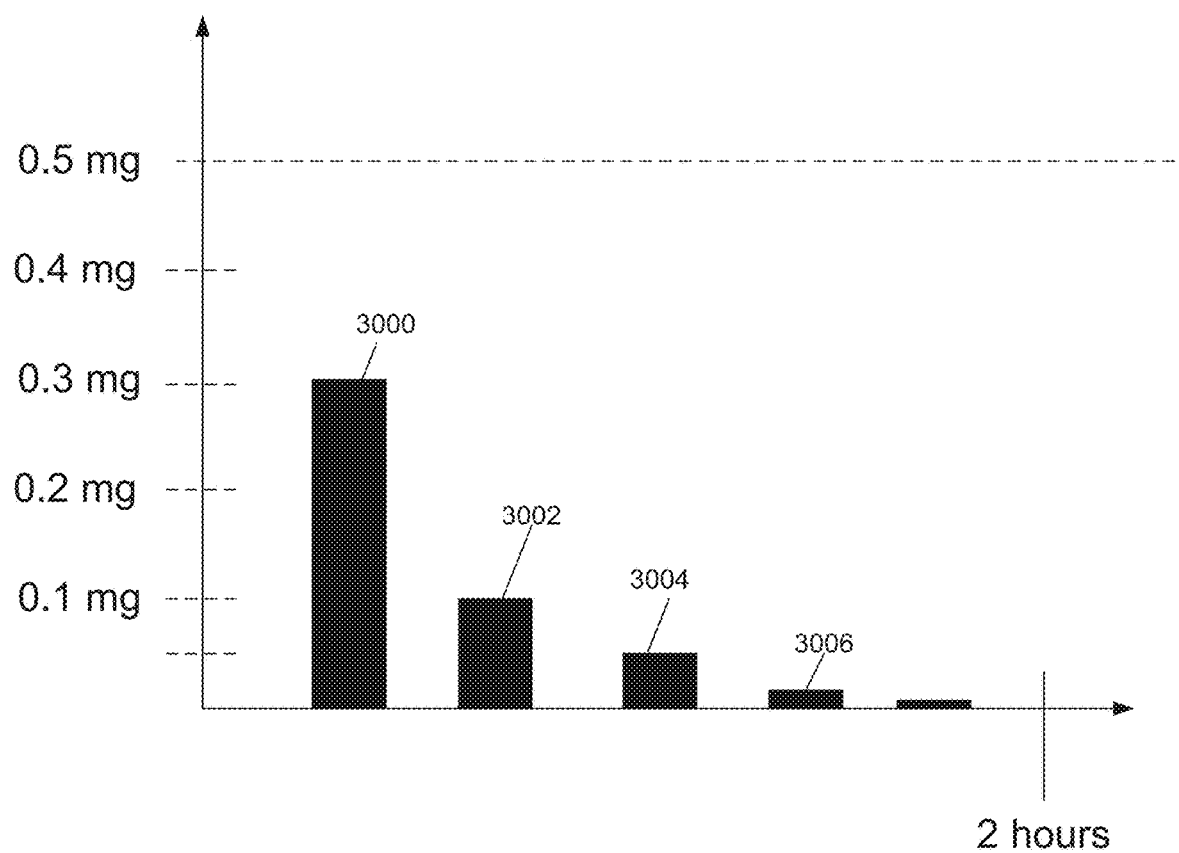
FIG. 16 is a graph of a delivery scheme of at least one active substance via an inhaler device, according to some embodiments of the invention.

FIG. 16 is a graph of a delivery scheme of at least one active substance via an inhaler device, according to some embodiments.

In some embodiments, a maximal amount of active substance is allocated for a predefined time period. In the example shown herein, a total of 0.5 mg is allocated for a 2 hour time period.

In some embodiments, delivery is limited according to a budgetary profile. Optionally, the device is configured to limit an amount delivered at each use session performed within the predefined time period so as to "save some for later". A cumulative scheme is presented in this example: an initial low dose 3000 of 0.3 mg is provided, followed by a plurality of micro doses summing up to a total of 0.5 mg delivered within a time period of 2 hours. The micro doses may include, for example, descending amounts which together with the initial low dose converge towards the maximal amount (e.g. 0.5 mg). For example, micro dose 3002 includes 0.1 mg; micro dose 3004 includes 0.05 mg; micro dose 3006 includes 0.02 mg and so forth. Optionally, doses provided towards the end of the time period include extremely small amounts, e.g. 0.01 mg.

An alternative delivery profile may include a "free manner" delivery in which any amount can be taken within the predefined time period, as long as the total amount delivered does not exceed the maximal amount. Optionally, the patient sets the specific amounts provided within the predefined time period, and the device limits use when the patient surpasses the maximal amount.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10 μm" is intended to mean "about 10 μm".

As used herein, numerical ranges preceded by the term "about" should not be considered to be limited to the recited range. Rather, numerical ranges preceded by the term "about" should be understood to include a range accepted by those skilled in the art for any given element in microcapsules or formulations according to the present disclosure.

The term "such as" should be taken to mean "for example" without any further limitation.

The term "about" as used herein means within an acceptable error range for a particular value as determined by one of ordinary skill in the art, which will depend in part on how the value is measured or determined, i.e., the limitations of the measurement system. For example, "about" can mean a range of up to 10%, more preferably up to 5%, and still more preferably up to 1% of a given value. Where particular values are described in the application and claims, unless otherwise stated, the meaning of the term "about" is within an acceptable error range for the particular value.

The terms "comprises", "comprising", "includes", "including", "having" and their conjugates mean "including but not limited to".

The term "consisting of" means "including and limited to".

The term "consisting essentially of" means that the composition, method or microcapsules may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present disclosure as delineated hereinabove and as claimed in the claims section below find experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

What is claimed is:

1. A system for delivering to a subject at least one pre-determined amount of THC, the system comprising:
a memory which stores a scheduled regimen for delivery of THC to said subject, said scheduled regimen administered over a total treatment period of a plurality of days, said scheduled regimen defining the delivery of a plurality of doses under the condition that a maximal amount of THC to be delivered in each of said plurality of doses is 2 mg or less, and a time period within which said amount of 2 mg or less is delivered is 2 hours or longer;
a decision module comprising circuitry configured to decide, according to said scheduled regimen, if a delivery should take place; and
an inhaler device for delivering said THC to said subject to thereby reduce at least one treated symptom without return of the symptom to a pre-inhalation degree for said time period of two hours or longer, said inhaler device comprising a controller which carries out delivery of said THC based on the decision made by said circuitry of said decision module; and wherein said inhaler device is configured to lock for predefined periods of time which are set according to said scheduled regimen, preventing additional delivery such that said amount of 2 mg or less delivered over 2 hours or longer is not surpassed.

2. The system according to claim 1, wherein said system is configured to deliver a total of no more than 10 mg THC over a 24 hour time period.

3. The system according to claim 1, wherein one or both of said memory and said decision module are included within at least one selected from the group consisting of:
   a. said inhaler device; and
   b. said controller.

4. The system according to claim 1, wherein one or both of said memory and said decision module are associated with or included in a smartphone.

5. The system according to claim 1, wherein said inhaler comprises a heating mechanism for heating a quantity of THC-comprising material to deliver THC from said quantity of THC-comprising material to said subject.

6. The system according to claim 1, wherein said controller carries out delivery of less than said maximal amount by controlling at least one selected from the group consisting of:
   a. heating parameters;
   b. an amount of THC-comprising material being heated;
   c. regulation of airflow;
   d. heating of a quantity of THC-comprising material having a THC content of between 2 times to 35 times the amount of THC being extracted;
   e. any combination thereof.

7. The system according to claim 5, wherein said inhaler is configured to heat said quantity of THC-comprising material at least once.

8. The system according to claim 5, wherein said THC-comprising material comprises one or more additional active substances.

9. The system according to claim 1, wherein said decision module is configured to perform at least one member selected from the group consisting of:
   a. prevent delivery for a time period long enough for at least one effect induced by said THC on said subject to take place;
   b. receive input regarding a THC-comprising material from which said THC is delivered, and, according to said input, to adjust said time period;
   c. adjust said time period according to one or more of: an amount or concentration of THC in said THC-comprising material; a strain of said THC-comprising material and additional active substances included in the THC-comprising material;
   d. analyze previous amounts delivered within any defined time period to determine whether an additional amount can be provided at a current or future time point; and
   e. any combination thereof.

10. The system according to claim 1, comprising at least two quantities of THC-comprising material differing from each other in at least one property selected from a group consisting of: a concentration of THC in the quantity, a strain of the THC-comprising material, additional active substances included in the THC-comprising material, the mass of the quantity of THC-comprising material and the total amount of THC in the quantity of THC-comprising material, and wherein said decision module is configured to select which cartridge to use according to a time period defined for each of said cartridges according to said at least one property.

11. The system according to claim 1, wherein in predefined exceptions said decision module is configured to allow delivery exceeding at least one of said maximal amount and said time period.

12. The system according to claim 11 wherein delivery under said predefined exceptions is limited according to one or more of:
   no more than two exceptional deliveries allowed within a 24 hour period;
   no more than two exceptional deliveries allowed within a 12 hour period;
   any exceptional delivery allowing no more than two folds said maximal amount of THC; and
   the total amount of THC delivered over a 24 hour period amounts to no more than 10 mg.

13. The system according to claim 11, wherein following an exceptional delivery said decision module returns to operate according to said scheduled regimen for a time period of at least 2 hours.

14. A method of controlling a THC dispensing device, comprising:
   dispensing THC according to a scheduled regimen administered over a total treatment period of a plurality of days, said dispensing comprising delivering a plurality of doses from said dispensing device under the condition that a maximal amount of THC to be delivered in each of said plurality of doses is
   1 mg or less, and a time period within which said amount of 1 mg or less is delivered is 2 hours or longer.

15. The method according to claim 14, wherein each of said plurality of doses is delivered over a single delivery event in which a single inhalation of a user from said THC dispensing device is performed.

16. The method according to claim 14, wherein a total of no more than 10 mg THC are dispensed over a 24 hour time period.

17. The system according to claim 1, wherein said decision module is operably connected to at least one of a timer and a clock for determining delivery in accordance with said scheduled regimen.

18. The system according to claim 1, wherein said inhaler device comprises a total amount of THC sufficient for treating a patient only for a predefined total treatment period selected from: at least a day, at least a week, at least a month.

19. The system according to claim 18, wherein said total amount of THC is 30 mg or less to be delivered over a predefined total treatment period of at least a week.

20. The system according to claim 19, wherein said total amount of THC is 10 mg or less to be delivered over a predefined total treatment period of at least a week.

21. The system according to claim 2, wherein said system is configured to deliver a total of no more than 3.5 mg THC over a 24 hour time period.

22. The system according to claim 1, wherein each of the deliveries of THC to said subject throughout said treatment period is made under that condition that a maximal amount of THC to be delivered is 1 mg or less, and a time period within which said amount of 1 mg or less is delivered is 2 hours or longer.

23. A system for delivering to a subject at least one pre-determined amount of THC, the system comprising: a memory which stores a scheduled regimen for delivery of THC to said subject over a period of at least a week, said scheduled regimen being pre-programmed so that an amount of THC delivered is sufficient to alleviate symptoms without causing a significant psychoactive effect; said scheduled regimen defining the delivery of a plurality of doses under the condition that a maximal amount of THC to be delivered in each of said plurality of doses is 1 mg or less, and a time period within which said amount of 1 mg or less is delivered is 2 hours or longer; a decision module comprising circuitry configured to decide, according to said scheduled regimen, if a delivery should take place; and an inhaler device for delivering said THC to said subject according to said scheduled regimen.

24. The system of claim 1, wherein said maximal amount of THC to be delivered in each of said plurality of doses is between 0.5 mg to 1 mg.

25. The system of claim 1, wherein a time interval between successive doses is at least two hours.

26. The system of claim 1, wherein said predetermined periods of time enable undesired effects of said THC to be minimized, and desired effects of said THC to reach at least a minimal acceptable level.

* * * * *